United States Patent
Wilmen et al.

(10) Patent No.: US 10,221,247 B2
(45) Date of Patent: *Mar. 5, 2019

(54) ANTIBODIES CAPABLE OF BINDING TO THE COAGULATION FACTOR XIA AND USES THEREOF

(71) Applicant: BAYER PHARMA AKTIENGESELLSCHAFT, Berlin (DE)

(72) Inventors: Andreas Wilmen, Köln (DE); Julia Straßburger, Wuppertal (DE); Frank Dittmer, Düsseldorf (DE); Michael Strerath, Düsseldorf (DE); Anja Buchmüller, Essen (DE); Joanna Grudzinska-Goebel, Berlin (DE); Ricarda Finnern, Aachen (DE); Martina Schäfer, Berlin (DE); Christoph Gerdes, Köln (DE); Hannah Jörißen, Heiligenhaus (DE); Asako Itakura, Portland, OR (US); Philberta Y. Leung, San Francisco, CA (US); Erik Tucker, Portland, OR (US)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,731

(22) Filed: Aug. 30, 2017

(65) Prior Publication Data

US 2018/0112009 A1   Apr. 26, 2018

Related U.S. Application Data

(62) Division of application No. 14/400,281, filed as application No. PCT/EP2013/059618 on May 8, 2013, now Pat. No. 9,783,614.

(60) Provisional application No. 61/817,675, filed on Apr. 30, 2013.

(30) Foreign Application Priority Data

May 10, 2012 (EP) .................. 12167438
Aug. 24, 2012 (EP) .................. 12181697
Jan. 7, 2013 (EP) .................. 13150361

(51) Int. Cl.
*C07K 16/36* (2006.01)
*A61K 39/00* (2006.01)

(52) U.S. Cl.
CPC ........ *C07K 16/36* (2013.01); *A61K 2039/505* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,231,938 A | 11/1980 | Monaghan et al. | |
| 4,399,216 A | 8/1983 | Axel et al. | |
| 4,444,784 A | 4/1984 | Hoffman et al. | |
| 4,510,245 A | 4/1985 | Cousens et al. | |
| 4,634,665 A | 1/1987 | Axel et al. | |
| 4,657,760 A | 4/1987 | Kung et al. | |
| 4,816,567 A | 3/1989 | Cabilly et al. | |
| 4,968,615 A | 11/1990 | Koszinowski et al. | |
| 5,168,062 A | 12/1992 | Stinski et al. | |
| 5,179,017 A | 1/1993 | Axel et al. | |
| 5,206,344 A | 4/1993 | Katre et al. | |
| 5,225,212 A | 7/1993 | Martin et al. | |
| 5,273,995 A | 12/1993 | Roth | |
| 5,354,772 A | 10/1994 | Kathawala | |
| 5,863,930 A | 1/1999 | Dressel et al. | |
| 5,877,289 A | 3/1999 | Thorpe et al. | |
| 6,989,250 B2 | 1/2006 | Soderlind et al. | |
| 8,236,316 B2 | 8/2012 | Gruber et al. | |
| 9,783,614 B2 * | 10/2017 | Wilmen ................. | C07K 16/36 |
| 2006/0057140 A1 | 3/2006 | Feuerstein | |
| 2006/0073535 A1 | 4/2006 | Greenfield et al. | |
| 2008/0138837 A1 | 6/2008 | Greenfield et al. | |
| 2010/0183625 A1 | 7/2010 | Sternlicht | |
| 2015/0099298 A1 | 4/2015 | Wilmen et al. | |

FOREIGN PATENT DOCUMENTS

| WO | 1998/016223 | 4/1998 |
|---|---|---|
| WO | 1998/16507 | 4/1998 |
| WO | 1998/23619 | 4/1998 |
| WO | 2000/006567 | 2/2000 |
| WO | 2000/06568 | 2/2000 |
| WO | 2000/06569 | 2/2000 |
| WO | 2000/07626 | 2/2000 |

(Continued)

OTHER PUBLICATIONS

Janeway et al., Immunobiology, 3rd ed., Current Biology, 1997, pp. 3:1-3:11.*
Rudikoff et al., Proc Natl Acad Sci USA. Mar. 1982;79(6):1979-83.*
Allen et al. "Interchain disulfide bonding in human IgG2 antibodies probed by site-directed mutagenesis" Biochem.48:3755-3766 (2009).
An et al. "IgG2m4, an engineered antibody isotype with reduced Fc function" mAbs 1:572-579 (2009).
Ausubel et al. *Short Protocols in Molecular Biology*, $3^{rd}$ Ed., pp. 10-1 thru 10-86 (1995).

(Continued)

*Primary Examiner* — Michael Szperka
(74) *Attorney, Agent, or Firm* — Nixon & Vanderhye P.C.

(57) ABSTRACT

The present invention relates to antibodies capable of binding to the coagulation Factor XI and/or its activated form factor XIa and methods of use thereof, particularly methods of use as agents inhibiting platelet aggregation and by this inhibits thrombus formation.

12 Claims, 24 Drawing Sheets

Specification includes a Sequence Listing.

(56) References Cited

FOREIGN PATENT DOCUMENTS

| WO | 2000/21954 | 4/2000 | | |
|---|---|---|---|---|
| WO | 2000/066582 | 11/2000 | | |
| WO | 2001/017998 | 3/2001 | | |
| WO | 2001/19355 | 3/2001 | | |
| WO | 2001/019776 | 3/2001 | | |
| WO | 2001/019778 | 3/2001 | | |
| WO | 2001/019780 | 3/2001 | | |
| WO | 2003/013423 | 2/2003 | | |
| WO | 2006/055176 | 5/2006 | | |
| WO | 2007/045366 | 4/2007 | | |
| WO | 2007/045367 | 4/2007 | | |
| WO | 2007/045369 | 4/2007 | | |
| WO | 2007/045370 | 4/2007 | | |
| WO | 2007/045433 | 4/2007 | | |
| WO | 2008/022295 | 2/2008 | | |
| WO | 2008/133857 | 11/2008 | | |
| WO | 2009/046274 | 4/2009 | | |
| WO | 2009/067660 | 5/2009 | | |
| WO | WO-2009067660 A2 * | 5/2009 | ............ | C07K 16/36 |
| WO | 2009/154461 | 12/2009 | | |
| WO | 2010/065275 | 6/2010 | | |
| WO | 2010/080623 | 7/2010 | | |
| WO | WO-2010080623 A2 * | 7/2010 | ............ | C07K 16/36 |
| WO | 2011/149921 | 12/2011 | | |
| WO | 2011/161099 | 12/2011 | | |
| WO | 2012/004258 | 1/2012 | | |
| WO | 2012/028647 | 3/2012 | | |
| WO | 2012/143510 | 10/2012 | | |
| WO | 2012/152629 | 11/2012 | | |
| WO | 2013/030138 | 3/2013 | | |
| WO | 2013/030288 | 3/2013 | | |

OTHER PUBLICATIONS

Baglia et al. "A binding site for thrombin in the Apple 1 domain of factor XI" J. Biol. Chem. 271:3652-3658 (1996).
Baglia "Functional domains in the heavy-chain region of factor XI: A high molecular weight kininogen-binding site and a substrate-binding site for factor IX" Blood 74:244-251 (1989).
Briggs et al. *CCP4 Newsletter on Protein Crystallography* No. 38, 60 pages (2000).
Capella "Generalized verrucosis: More emphasis on systemic retinoids" J. Am. Acad. Dermatol. 67:1074 (2012).
Carlsson et al. "n-CoDeR concept: Unique types of therapy" Exp. Rev. Mol. Diagn. 1:102-108 (2001).
Chothia et al. "Canonical structures for the hypervariable regions of immunoglobulins" J. Mol. Biol. 196:901-917 (1987).
Davie et al. "Waterfall sequence for intrinsic blood clotting" Science 145:1310-1312 (1964).
Davie et al. "The coagulation cascade: Initiation, maintenance, and regulation" Biochem. 43:10363-10370 (1991).
De La Cadena et al. "Naturally occurring human antibodies against two distinct functional domains in the heavy chain of FXI/FXIa" Blood 72:1748-1754 (1988).
Douglas et al. "Vitamin C for preventing and treating the common cold" Cochrane Database Syst. Rev. Issue 4, Art. No. CD000980.p2, 47 pages (2004).
Du Pasquier et al. "Chapter 7: Evolution of the immune system" *Fundamental Immunology* 2$^{nd}$ Ed., pp. 139-165 (1989).
Emsley et al. "Features and development of Coot" Acta Cryst. D 66:486-501 (2010).
Evans "Scaling and assessment of data quality" Acta Cryst. D62:72-82 (2005).
Fujikawa et al. "Amino acid sequence of human factor XI, a blood coagulation factor with four tandem repeats that are highly homologous with plasma prekallikrein" Biochem. 25:2417-2424 (1986).
Gailani et al. "Factor XI activation in a revised model of blood coagulation" Science 253:909-912 (1991).
Gruber et al. "Relative antithrombotic and antihemostatic effects of protein C activator versus low-molecular-weight heparin in primates" Blood 109:3733-3740 (2007).
Gruber et al. "Antithrombotic factor XI antibody inhibition of the intrinsic pathway" Blood 98:42a, abstract at 43rd Annual Meeting of the American Society of Hematology (2001).
Gruber et al. "Factor XI-dependence of surface- and tissue factor-initiated thrombus propagation in primates" Blood 102:953-955 (2003).
Hanson et al. "Antithrombotic effects of thrombin-induced activation of endogenous protein C in primates" J. Clin. Invest. 92:2003-2012 (1993).
Hezareh et al. "Effector function activities of a panel of mutants of a broadly neutralizing antibody against human immunodeficiency virus type 1" J. Virol. 75:12161-12168 (2001).
Hoet et al. "Generation of high-affinity human antibodies by combining donor-derived and synthetic complementarity-determining-region diversity" Nat. Biotech. 23:344-348 (2005).
Hoffman et al. "Rethinking the coagulation cascade" Curr. Hematol. Rep. 4:391-396 (2005).
Janeway *Immunobiology: The Immune System in Health and Disease* 3$^{rd}$ Ed., pp. 3:1-3:11 (1997).
Janeway "Chapter 8: Immunogenicity and antigen structure" *Fundamental Immunology*, p. 242 (1993).
Johne et al. "Platelets promote coagulation factor XII-mediated proteolytic cascade systems in plasma" Biol. Chem. 387:173-178 (2006).
Johnson et al. "Kabat database and its applications: 30 years after the first variability plot" Nucl. Acids Res. 28:214-218 (2000).
Kabsch "XDS" Acta Cryst. D 66:125-132 (2010).
Kaufman et al. "Amplification and expression of sequences cotransfected with a modular dihydrofolate reductase complementary DNA Gene" J. Mol. Biol. 159:601-621 (1982).
Knappik et al. "Fully synthetic human combinatorial antibody libraries (HuCAL) based on modular consensus frameworks and CDRs randomized with trinucleotides" J. Mol. Biol. 296:57-86 (2000).
Kohler et al. "Continuous cultures of fused cells secreting antibody of predefined specificity" Nature 256:495-497 (1975).
Kravtsov et al. "Factor XI contributes to thrombin generation in the absence of factor XII" Blood 114:452-458 (2009).
Krebs et al. "High-throughput generation and engineering of recombinant human antibodies" J. Immunol. Meth. 254:67-84 (2001).
Labrijn et al. "When binding is enough: Nonactivating antibody formats" Curr. Opin. Immunol. 20:479-485 (2008).
Lisman et al. "Factor XI binding to platelets: Glycoprotein Ibα has an accomplice" Arterioscler. Thromb. Vasc. Biol. 29:1409-1410 (2009).
Long et al. "BALBES: A molecular-replacement pipeline" Acta Cryst. D 64:125-132 (2008).
MacFarlane "An enzyme cascade in the blood. Clotting mechanism and its function as a biochemical amplifier" Nature 202:498-499 (1964).
Meijers et al. "Feedback controversy stops here" Blood 114:235 (2009).
Meijers et al. "High levels of coagulation factor XI as a risk factor for venous thrombosis" New Engl. J. Med. 342:696-701(2000).
Murshudov "Refinement of macromolecular structures by the maximum-likelihood method" Acta Cryst. D 53:240-255 (1997).
Nishikado "Murine monoclonal antibodies to human factor XI" Thromb. Res. 42:225-234 (1986).
Payne et al. "Combined therapy with clopidogrel and aspirin significantly increases the bleeding time through a synergistic antiplatelet action" J. Vascular Surg. 35:1204-1209 (2002).
Percy et al. "Probing protein interactions with hydrogen/deuterium exchange and mass spectrometry—A review" Anal. Chimica Acta 721:7-21 (2012).
Portolano et al. "Lack of promiscuity in autoantigen-specific H and L chain combinations as revealed by human H and L chain "Roulette" J. Immunol. 150:880-887 (1993).
Plückthun "Chapter 11: Antibodies from *Escherichia coli*" *The Pharmacology of Monoclonal Antibodies*, Rosenberg et al., Eds. 113, pp. 269-315 (1994).
Riva et al. "Loco-regional radioimmunotherapy of high-grade malignant gliomas using specific monoclonal antibodies labeled with 90Y: A phase I study" Clin. Cancer Res. 5:3275s-3280s (1999).

(56) References Cited

OTHER PUBLICATIONS

Rosen "The factor of factor XI deficiency in thyroid neoplasia" Surgery 100:1062-1067 (1986).
Rudikoff et al. "Single amino acid substitution altering antigen-binding specificity" Proc. Natl. Acad. Sci. USA 79:1979-1983 (1982).
Salomon et al "Reduced incidence of ischemic stroke in patients with severe factor XI deficiency" Blood 111:4113-4117 (2008).
Salomon et al. "Patients with severe factor XI deficiency have a reduced incidence of deep vein thrombosis" Thromb. Haemost. 105:269-273 (2011).
Sambrook et al. *Molecular Cloning: A Laboratory Manual*, 2$^{nd}$ Ed., 2:10.1-10.70 (1989).
Sambrook et al. *Molecular Cloning: A Laboratory Manual*, 2$^{nd}$ Ed., 2:8.1-8.86 (1989).
Sambrook et al. *Molecular Cloning: A Laboratory Manual*, 2$^{nd}$ Ed., 1:1.1-1.110 (1989).
Sambrook et al. *Molecular Cloning: A Laboratory Manual*, 2$^{nd}$ Ed., 1:4.1-4.54 (1989).
Sambrook et al. *Molecular Cloning: A Laboratory Manual*, 2$^{nd}$ Ed., 1:6.1-6.62 (1989).
Sambrook et al. *Molecular Cloning: A Laboratory Manual*, 2$^{nd}$ Ed., 2:9.1-9.62 (1989).
Sasahara "Chapter 1: New therapeutic agents in thrombosis" *New Therapeutic Agents for Thrombosis and Thrombolysis*, 2$^{nd}$ Ed. p. 879 (2005).
Sazinskya et al. "Aglycosylated immunoglobulin G1 variants productively engage activating Fc receptors" Proc. Natl. Acad. Sci. USA 105:20167-20172 (2008).
Schuurman et al. "Normal human immunoglobulin G4 is bispecific: It has two different antigen-combining sites" Immunol. 97:693-698 (1999).
Simmons et al. "Expression of full-length immunoglobulins in *Escherichia coli*: Rapid and efficient production of aglycosylaled antibodies" J. Immunol. Meth. 263:133-147 (2002).
Sinha et al. "Functional characterization of human blood coagulation factor Xia using hybridoma antibodies" J. Biol. Chem. 260:10714-10719 (1985).
Smith et al. "The prolonged bleeding time in hemophilia A: Comparison of two measuring technics and clinical associations" AJCP 83:211-215 (1985).
SRI "Generalized verrucosis: a review of the associated diseases evaluation, and treatments" J. Am. Acad. Dermatol. 66:292-311 (2012).
Sun "Identification of a factor IX binding site on the third apple domain of activated factor XI" J. Biol. Chem. 271:29023-29028 (1996).
Sun et al. "Identification of amino acids in the factor XI apple 3 domain required for activation of factor IX" J. Biol. Chem. 274:36373-36378 (1999).
Tucker "Inhibition of factor XI decreases thrombin production and prevents vascular occlusion in experimental thrombosis in primates" Blood 110:235A (2007).
Tucker "Prevention of vascular graft occlusion and thrombus-associated thrombin generation by inhibition of factor XI" Blood 113:936-944 (2009).
Tucker "Survival advantage of coagulation factor XI-Deficient mice during peritoneal sepsis" J. Infect. Dis. 198:271-274 (2008).
Ulku et al. "Cis-1,1'-Dimethyl-3,3'-diphenyl-2,2'-biimidazolidinylidene" Acta Cryst. C 53:240-241 (1997).
Urlaub et al. "Isolation of Chinese hamster cell mutants deficient in dihydrofolate reductase activity" Proc. Natl. Acad. Sci. USA 77:4216-4220(1980).
White-Adams "Identification of coagulation factor XI as a ligand for platelet apolipoprotein E receptor 2 (ApoER2)" Arterioschler Thromb. Vasc. Biol. 29:1602-1607 (2009).
Yamada "Development of antibody against epitope of lipoprotein(a) modified by oxidation" Circulation 102:1639-1644 (2000).
Yamashita "Factor XI contributes to thrombus propagation on injured neointima of the rabbit iliac artery" J. Thromb. Haemostasis 4:1496-1501 (2006).
Zapata et al. "Engineering linear F(ab')2 fragments for efficient production in *Escherichia coli* and enhanced antiproliferative activity" Protein Eng. 8:1057-1062 (1995).
International Search Report; PCT/EP2013/059618, dated Sep. 24, 2013.
International Search Report for PCT/US2008/084336, four pages, dated May 4, 2009.
Int'l Preliminary Report on Patentability for PCT/US2008/084336, six pages, dated May 25, 2010.
Written Opinion of the ISA for PCT/US2008/084336, five pages, dated May 21, 2010.

* cited by examiner

SEQUENCE LISTING

```
<160> NUMBER OF SEQ ID NOS: 184

<210> SEQ ID NO 1
<211> LENGTH: 321
<212> TYPE: DNA
<213> ORGANISM: Homo sapiens

<400> SEQUENCE: 1
gatattcaga tgacccagag cccgagcagc ctgagcgcga gcgtgggcga tcgcgtgacc      60
attacctgcc aggcgagcca ggatattagc aactatctga actggtatca gcagaaaccg     120
ggcaaagcgc cgaaactgct gatttatgat gcgagcaacc tggaaaccgg cgtgccgagc     180
cgctttagcg gcagcggcag cggcaccgat tttacctta ccattagcag cctgcagccg      240
gaagatattg cgacctatta ttgccagcag gcgaacagct tccggtgac ctttggcggc      300 ggcaccaaag tggaaattaa a                                               321

<210> SEQ ID NO 2
<211> LENGTH: 360
<212> TYPE: DNA
<213> ORGANISM: Homo sapiens

<400> SEQUENCE: 2
gaagtgcagc tgctggaaag cggcggcggc ctggtgcagc cggcggcag cctgcgcctg       60 agctgcgcgg cgagcggctt tacctttagc cagtatggca tggattgggt cgccaggcg      120 ccgggcaaag gcctggaatg ggtgagcggc attggcccga gcggcggcag caccgtgtat     180
gcggatagcg tgaaaggccg ctttaccatt agccgcgata cagcaaaaa cacctgtat      240 ctgcagatga acagcctgcg cgcggaagat accgcggtgt attattgcac ccgcgcggc      300 ccgtattatt attatggcat ggatgtgtgg ggccagggca ccaccgtgac cgtgagcagc     360

<210> SEQ ID NO 3
<211> LENGTH: 30
<212> TYPE: DNA
<213> ORGANISM: Homo sapiens

<400> SEQUENCE: 3
ggctttacct ttagccagta tggcatggat                                       30

<210> SEQ ID NO 4
<211> LENGTH: 30
<212> TYPE: DNA
<213> ORGANISM: Homo sapiens

<400> SEQUENCE: 4
```

```
ggcattggcc cgagcggcgg cagcaccgtg                                        30

<210> SEQ ID NO 5
<211> LENGTH: 39
<212> TYPE: DNA
<213> ORGANISM: Homo sapiens

<400> SEQUENCE: 5
acccgcggcg gcccgtatta ttattatggc atggatgtg                              39

<210> SEQ ID NO 6
<211> LENGTH: 33
<212> TYPE: DNA
<213> ORGANISM: Homo sapiens

<400> SEQUENCE: 6
caggcgagcc aggatattag caactatctg aac                                    33

<210> SEQ ID NO 7
<211> LENGTH: 21
<212> TYPE: DNA
<213> ORGANISM: Homo sapiens

<400> SEQUENCE: 7
gatgcgagca acctggaaac c                                                 21

<210> SEQ ID NO 8
<211> LENGTH: 21
<212> TYPE: DNA
<213> ORGANISM: Homo sapiens

<400> SEQUENCE: 8
cagcaggcga acagctttcc g                                                 21

<210> SEQ ID NO 9
<211> LENGTH: 321
<212> TYPE: DNA
<213> ORGANISM: Homo sapiens

<400> SEQUENCE: 9
gatattcaga tgacccagag cccgagcagc ctgagcgcga gcgtgggcga tcgcgtgacc       60
attacctgcc aggcgagcca ggatattagc aactatctga actggtatca gcagaaaccg      120
ggcaaagcgc cgaaactgct gatttatgat gcgagcaacc tggaaaccgg cgtgccgagc      180
cgctttagcg gcagcggcag cggcaccgat tttacctttta ccattagcag cctgcagccg      240
gaagatattg cgacctatta ttgccagcag gcggatagct ttccggtgac ctttggcggc      300
ggcaccaaag tggaaattaa a                                                321

<210> SEQ ID NO 10
<211> LENGTH: 21
<212> TYPE: DNA
<213> ORGANISM: Homo sapiens

<400> SEQUENCE: 10
cagcaggcgg atagctttcc g                                                 21

<210> SEQ ID NO 11
<211> LENGTH: 321
<212> TYPE: DNA
<213> ORGANISM: Homo sapiens

<400> SEQUENCE: 11
```

```
gatattcaga tgacccagag cccgagcagc gtgagcgcga gcgtgggcga tcgcgtgacc    60
attacctgcc gcgcgagcca gggcattagc agctggctgg cgtggtatca gcagcgcccg   120
ggcaaagcgc cgaaactgct gatttatgat gcgagcaccc tgcagagcgg cgtgccgagc   180
cgctttagcg gcagcggcag cggcaccgat tttaccctga ccattaacag cctgcagccg   240
gaaaactttg cgacctatta ttgccagcag gcggatagct ttccgattgc gtttggccag   300
ggcacccgcc tggaaattaa a                                              321

<210> SEQ ID NO 12
<211> LENGTH: 354
<212> TYPE: DNA
<213> ORGANISM: Homo sapiens

<400> SEQUENCE: 12
gaagtgcagc tgctggaaag cggcggcggc ctggtgcagc cgggcggcag cctgcgcctg    60
agctgcgcgg cgagcggctt tacctttagc gattatgaaa tggcgtgggt cgcccaggcg   120
ccgggcaaag gcctggaatg ggtgagcagc attgtgccga gcggcggctg gaccctgtat   180
gcggatagcg tgaaaggccg ctttaccatt agccgcgata acagcaaaaa caccctgtat   240
ctgcagatga acagcctgcg cgcggaagat accgcggtgt attattgcgc gacctggggc   300
gatagctggg gctttgattt ttggggccag ggcacccctgg tgaccgtgag cagc        354

<210> SEQ ID NO 13
<211> LENGTH: 30
<212> TYPE: DNA
<213> ORGANISM: Homo sapiens

<400> SEQUENCE: 13
ggctttacct ttagcgatta tgaaatggcg                                     30

<210> SEQ ID NO 14
<211> LENGTH: 30
<212> TYPE: DNA
<213> ORGANISM: Homo sapiens

<400> SEQUENCE: 14
agcattgtgc cgagcggcgg ctggaccctg                                     30

<210> SEQ ID NO 15
<211> LENGTH: 33
<212> TYPE: DNA
<213> ORGANISM: Homo sapiens

<400> SEQUENCE: 15
gcgacctggg gcgatagctg gggctttgat ttt                                 33

<210> SEQ ID NO 16
<211> LENGTH: 33
<212> TYPE: DNA
<213> ORGANISM: Homo sapiens

<400> SEQUENCE: 16
cgcgcgagcc agggcattag cagctggctg gcg                                 33

<210> SEQ ID NO 17
<211> LENGTH: 21
<212> TYPE: DNA
<213> ORGANISM: Homo sapiens
```

<400> SEQUENCE: 17
gatgcgagca ccctgcagag c                                          21

<210> SEQ ID NO 18
<211> LENGTH: 33
<212> TYPE: DNA
<213> ORGANISM: Homo sapiens

<400> SEQUENCE: 18
cagcaggcgg atagctttcc gattgcgttt ggc                             33

<210> SEQ ID NO 19
<211> LENGTH: 107
<212> TYPE: PRT
<213> ORGANISM: Homo sapiens

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 20
<211> LENGTH: 120
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Tyr Gly Met Asp Val Trp Gly Gln
            100                 105                 110

Gly Thr Thr Val Thr Val Ser Ser
        115                 120

<210> SEQ ID NO 21
<211> LENGTH: 10
<212> TYPE: PRT

<213> ORGANISM: Homo sapiens

<400> SEQUENCE: 21

Gly Phe Thr Phe Ser Gln Tyr Gly Met Asp
1               5                   10

<210> SEQ ID NO 22
<211> LENGTH: 10
<212> TYPE: PRT
<213> ORGANISM: Homo sapiens

<400> SEQUENCE: 22

Gly Ile Gly Pro Ser Gly Gly Ser Thr Val
1               5                   10

<210> SEQ ID NO 23
<211> LENGTH: 13
<212> TYPE: PRT
<213> ORGANISM: Homo sapiens

<400> SEQUENCE: 23

Thr Arg Gly Gly Pro Tyr Tyr Tyr Tyr Gly Met Asp Val
1               5                   10

<210> SEQ ID NO 24
<211> LENGTH: 11
<212> TYPE: PRT
<213> ORGANISM: Homo sapiens

<400> SEQUENCE: 24

Gln Ala Ser Gln Asp Ile Ser Asn Tyr Leu Asn
1               5                   10

<210> SEQ ID NO 25
<211> LENGTH: 7
<212> TYPE: PRT
<213> ORGANISM: Homo sapiens

<400> SEQUENCE: 25

Asp Ala Ser Asn Leu Glu Thr
1               5

<210> SEQ ID NO 26
<211> LENGTH: 7
<212> TYPE: PRT
<213> ORGANISM: Homo sapiens

<400> SEQUENCE: 26

Gln Gln Ala Asn Ser Phe Pro
1               5

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Ser Phe Pro Val
                    85                  90                  95

Thr Phe Gly Gly Gly Thr Lys Val Glu Ile Lys
                100                 105

<210> SEQ ID NO 28
<211> LENGTH: 7
<212> TYPE: PRT
<213> ORGANISM: Homo sapiens

<400> SEQUENCE: 28

Gln Gln Ala Asp Ser Phe Pro
1               5

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asn Phe Ala Thr Tyr Tyr Cys Gln Gln Ala Asp Ser Phe Pro Ile
                85                  90                  95

Ala Phe Gly Gln Gly Thr Arg Leu Glu Ile Lys
                100                 105

<210> SEQ ID NO 30
<211> LENGTH: 118
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Trp Gly Asp Ser Trp Gly Phe Asp Phe Trp Gly Gln Gly Thr

```
                    100                 105                 110
Leu Val Thr Val Ser Ser
        115

<210> SEQ ID NO 31
<211> LENGTH: 10
<212> TYPE: PRT
<213> ORGANISM: Homo sapiens

<400> SEQUENCE: 31

Gly Phe Thr Phe Ser Asp Tyr Glu Met Ala
1               5                   10

<210> SEQ ID NO 32
<211> LENGTH: 10
<212> TYPE: PRT
<213> ORGANISM: Homo sapiens

<400> SEQUENCE: 32

Ser Ile Val Pro Ser Gly Gly Trp Thr Leu
1               5                   10

<210> SEQ ID NO 33
<211> LENGTH: 11
<212> TYPE: PRT
<213> ORGANISM: Homo sapiens

<400> SEQUENCE: 33

Ala Thr Trp Gly Asp Ser Trp Gly Phe Asp Phe
1               5                   10

<210> SEQ ID NO 34
<211> LENGTH: 11
<212> TYPE: PRT
<213> ORGANISM: Homo sapiens

<400> SEQUENCE: 34

Arg Ala Ser Gln Gly Ile Ser Ser Trp Leu Ala
1               5                   10

<210> SEQ ID NO 35
<211> LENGTH: 7
<212> TYPE: PRT
<213> ORGANISM: Homo sapiens

<400> SEQUENCE: 35

Asp Ala Ser Thr Leu Gln Ser
1               5

<210> SEQ ID NO 36
<211> LENGTH: 11
<212> TYPE: PRT
<213> ORGANISM: Homo sapiens

<400> SEQUENCE: 36

Gln Gln Ala Asp Ser Phe Pro Ile Ala Phe Gly
1               5                   10

<210> SEQ ID NO 37
<211> LENGTH: 372
<212> TYPE: DNA
<213> ORGANISM: Homo sapiens

<400> SEQUENCE: 37
```

```
gaagtgcagc tgctggaaag cggcggcggc ctggtgcagc cgggcggcag cctgcgcctg    60
agctgcgcgg cgagcggctt tacctttagc cgctatatta tgcattgggt gcgccaggcg    120
ccgggcaaag gcctggaatg ggtgagcagc attagcccga gcggcggcct gaccagctat    180
gcggatagcg tgaaaggccg ctttaccatt agccgcgata acagcaaaaa caccctgtat    240
ctgcagatga acagcctgcg cgcggaagat accgcggtgt attattgcgc gcgcgaattt    300
gaaaacgcgt atcattatta ttattatggc atggatgtgt ggggccaggg caccaccgtg    360
accgtgagca gc                                                        372
```

<210> SEQ ID NO 38
<211> LENGTH: 321
<212> TYPE: DNA
<213> ORGANISM: Homo sapiens

<400> SEQUENCE: 38

```
gatattcaga tgacccagag cccgagcagc ctgagcgcga gcgtgggcga tcgcgtgacc    60
attacctgcc gcgcgagcgg cgatattggc aacgcgctgg cctggtatca gcagaaaccg    120
ggcaaagcgc cgcgcctgct gattagcgat gcgagcaccc tgcagagcgg cgtgccgctg    180
cgctttagcg gcagcggcag cggcaccgaa tttaccctga ccattagcag cctgcagccg    240
gaagattttg cgacctatta ttgcctgcag ggctataact atccgcgcac ctttggccag    300
ggcaccaaac tggaaattcg c                                              321
```

<210> SEQ ID NO 39
<211> LENGTH: 372
<212> TYPE: DNA
<213> ORGANISM: Homo sapiens

<400> SEQUENCE: 39

```
gaagtgcagc tgctggaaag cggcggcggc ctggtgcagc cgggcggcag cctgcgcctg    60
agctgcgcgg cgagcggctt tacctttagc tggtatccga tgcagtgggt gcgccaggcg    120
ccgggcaaag gcctggaatg ggtgagcggc attagcagca gcggcggcgg cacctattat    180
gcggatagcg tgaaaggccg ctttaccatt agccgcgata acagcaaaaa caccctgtat    240
ctgcagatga acagcctgcg cgcggaagat accgcggtgt attattgcgc gcgcgattgg    300
ggctatagca actatgtgat ggatctgggc ctggattatt ggggccaggg cacccctggtg   360 accgtgagca gc                                                        372
```

<210> SEQ ID NO 40
<211> LENGTH: 321
<212> TYPE: DNA
<213> ORGANISM: Homo sapiens

<400> SEQUENCE: 40

```
gatattcaga tgacccagag cccggcgacc ctgagcctga gcgcgggcga acgcgcgacc    60
ctgagctgcc gcgcgagcca gaccgtgagc agcagcctgg cgtggtatca gcataaaccg    120
ggccaggcgc cgcgcctgct gatttatgaa accagcaacc gcgcgaccgg cattccggcg    180
cgctttagcg gcagcggcag cggcaccgat tttaccctga ccattagcag cctggaaccg    240
gaagattttg cggtgtatta ttgccagcat cgcagcaact ggccgccgac ctttggcccg    300
ggcaccaaag tggatattaa a                                              321
```

<210> SEQ ID NO 41
<211> LENGTH: 372

```
<212> TYPE: DNA
<213> ORGANISM: Homo sapiens

<400> SEQUENCE: 41
gaagtgcagc tgctggaaag cggcggcggc ctggtgcagc cgggcggcag cctgcgcctg      60
agctgcgcgg cgagcggctt tacctttagc acctatagca tgggctgggt gcgccaggcg     120
ccgggcaaag gcctggaatg ggtgagcagc attagcccga gcggcggcga taccgattat     180
gcggatagcg tgaaaggccg ctttaccatt agccgcgata acagcaaaaa cacccctgtat    240
ctgcagatga acagcctgcg cgcggaagat accgcggtgt attattgcgc gcgcgaacgc     300
accatggtgc gcgatccgcg ctattatggc atggatgtgt ggggccaggg caccaccgtg     360
accgtgagca gc                                                         372

<210> SEQ ID NO 42
<211> LENGTH: 321
<212> TYPE: DNA
<213> ORGANISM: Homo sapiens

<400> SEQUENCE: 42
gatattcaga tgacccagag cccggcgacc ctgagcctga gcccgggcga acgcgcgacc      60
ctgagctgcc gcgcgagcca gagcgtgagc agctatctgg cgtggtatca gcagcgcctg     120
ggccagagcc cgcgcctgct gatttatgat gcgagcagcc gcgcgaccgg cattccggcg     180
cgctttagcg gcagcggcag cggcaccgat tttaccctga ccattagcag cctgcagccg     240
gaagattttg cgacctatta ttgccagcag agctatagca acctggtgac ctttggccag     300
ggcacccgcc tggaaattaa a                                               321

<210> SEQ ID NO 43
<211> LENGTH: 372
<212> TYPE: DNA
<213> ORGANISM: Homo sapiens

<400> SEQUENCE: 43
gaagtgcagc tgctggaaag cggcggcggc ctggtgcagc cgggcggcag cctgcgcctg      60
agctgcgcgg cgagcggctt tacctttagc ctgtattata tgaaatgggt gcgccaggcg     120
ccgggcaaag gcctggaatg ggtgagcagc attagcccga gcggcggctt taccagctat     180
gcggatagcg tgaaaggccg ctttaccatt agccgcgata acagcaaaaa cacccctgtat    240
ctgcagatga acagcctgcg cgcggaagat accgcggtgt attattgcgc gcgcgaattt     300
gaaaacgcgt atcattatta ttattatggc atggatgtgt ggggccaggg caccaccgtg     360
accgtgagca gc                                                         372

<210> SEQ ID NO 44
<211> LENGTH: 321
<212> TYPE: DNA
<213> ORGANISM: Homo sapiens

<400> SEQUENCE: 44
gatattcaga tgacccagag cccgagcagc gtgagcgcga gcgtgggcga tcgcgtgacc      60
attacctgcc gcgcgagcca ggatattaac atttggctgg cgtggtatca gcagaaaccg     120
ggcaaagcgc cgaaactgct gattagcgcg gcgagcaccg tgcagagcgg cgtgccgagc     180
cgctttagcg gcagcggcag cggcaccgat tttaccctga ccattaacac cctgcagccg     240
gatgattttg cgacctatta ttgccagcag gcggcgagct ttccgctgac ctttggcggc     300
```

```
ggcaccaaag tggaaatgaa a                                              321
```

<210> SEQ ID NO 45
<211> LENGTH: 372
<212> TYPE: DNA
<213> ORGANISM: Homo sapiens

<400> SEQUENCE: 45

```
gaagtgcagc tgctggaaag cggcggcggc ctggtgcagc cgggcggcag cctgcgcctg    60
agctgcgcgg cgagcggctt tacctttagc acctatagca tgggctgggt gcgccaggcg   120
ccgggcaaag gcctggaatg ggtgagcagc attagcccga gcggcggcga taccgattat   180
gcggatagcg tgaaaggccg ctttaccatt agccgcgata acagcaaaaa caccctgtat   240
ctgcagatga acagcctgcg cgcggaagat accgcggtgt attattgcgc gcgcgaacgc   300
accatggtgc gcgatccgcg ctattatggc atggatgtgt ggggccaggg caccaccgtg   360
accgtgagca gc                                                       372
```

<210> SEQ ID NO 46
<211> LENGTH: 321
<212> TYPE: DNA
<213> ORGANISM: Homo sapiens

<400> SEQUENCE: 46

```
gatattcaga tgacccagag cccggcgacc ctgagcctga gcccgggcga acgcgcgacc    60
ctgagctgcc gcgcgagcca gagcgtgagc agctatctgg cgtggtatca gcagcgcctg   120
ggccagagcc cgcgcctgct gatttatgat gcgagcagcc gcgcgaccgg cattccggcg   180
cgctttagcg gcagcggcag cggcaccgat tttaccctga ccattagcag cctgcagccg   240
aaagattttg cgacctatta ttgccagcag agctatagca acctggtgac ctttggccag   300
ggcacccgcc tggaaattaa a                                             321
```

<210> SEQ ID NO 47
<211> LENGTH: 372
<212> TYPE: DNA
<213> ORGANISM: Homo sapiens

<400> SEQUENCE: 47

```
gaagtgcagc tgctggaaag cggcggcggc ctggtgcagc cgggcggcag cctgcgcctg    60
agctgcgcgg cgagcggctt tacctttagc tggtatccga tgcagtgggt gcgccaggcg   120
ccgggcaaag gcctggaatg ggtgagcggc attagcagca gcggcggcgg cacctattat   180
gcggatagcg tgaaaggccg ctttaccatt agccgcgata acagcaaaaa caccctgtat   240
ctgcagatga acagcctgcg cgcggaagat accgcggtgt attattgcgc gcgcgattgg   300
ggctatagca actatgtgat ggatctgggc ctggattatt ggggccaggg caccctggtg   360
accgtgagca gc                                                       372
```

<210> SEQ ID NO 48
<211> LENGTH: 321
<212> TYPE: DNA
<213> ORGANISM: Homo sapiens

<400> SEQUENCE: 48

```
gatattcaga tgacccagag cccggcgacc ctgagcctga gcgcgggcga acgcgcgacc    60
ctgagctgcc gcgcgagcca gaccgtgagc agcagcctgg cgtggtatca gcataaaccg   120
ggccaggcgc cgcgcctgct gatttatgaa accagcaacc gcgcgaccgg cattccggcg   180
```

-continued

```
cgctttagcg gcagcggcag cggcaccgat tttaccctga ccattagcag cctggaaccg    240
gaagattttg cggtgtatta ttgccagcat cgcagcaact ggccgccgac ctttggcccg    300
ggcaccaaag tggatattaa a                                              321
```

<210> SEQ ID NO 49
<211> LENGTH: 372
<212> TYPE: DNA
<213> ORGANISM: Homo sapiens

<400> SEQUENCE: 49

```
gaagtgcagc tgctggaaag cggcggcggc ctggtgcagc cgggcggcag cctgcgcctg     60
agctgcgcgg cgagcggctt tacctttagc tggtatccga tgcagtgggt gcgccaggcg    120
ccgggcaaag gcctggaatg ggtgagcggc attagcagca gcggcggcgg cacctattat    180
gcggatagcg tgaaaggccg ctttaccatt agccgcgata acagcaaaaa caccctgtat    240
ctgcagatga acagcctgcg cgcggaagat accgcggtgt attattgcgc gcgcgattgg    300
ggctatagca actatgtgat ggatctgggc ctggattatt ggggccaggg caccctggtg    360
accgtgagca gc                                                        372
```

<210> SEQ ID NO 50
<211> LENGTH: 321
<212> TYPE: DNA
<213> ORGANISM: Homo sapiens

<400> SEQUENCE: 50

```
gatattcaga tgacccagag cccggcgacc ctgagcctga gcgcgggcga acgcgcgacc     60
ctgagctgcc gcgcgagcca gaccgtgagc agcagcctgg cgtggtatca gcataaaccg    120
ggccaggcgc cgcgcctgct gatttatgaa accagcaacc gcgcgaccgg cattccggcg    180
cgctttagcg gcagcggcag cggcaccgat tttaccctga ccattagcag cctggaaccg    240
gaagattttg cggtgtatta ttgccagcat cgcagcaact ggccgccgac ctttggcccg    300
ggcaccaaag tggatattaa a                                              321
```

<210> SEQ ID NO 51
<211> LENGTH: 372
<212> TYPE: DNA
<213> ORGANISM: Homo sapiens

<400> SEQUENCE: 51

```
gaagtgcagc tgctggaaag cggcggcggc ctggtgcagc cgggcggcag cctgcgcctg     60
agctgcgcgg cgagcggctt tacctttagc acctatagca tgggctgggt gcgccaggcg    120
ccgggcaaag gcctggaatg ggtgagcagc attagcccga gcggcggcga taccgattat    180
gcggatagcg tgaaaggccg ctttaccatt agccgcgata acagcaaaaa caccctgtat    240
ctgcagatga acagcctgcg cgcggaagat accgcggtgt attattgcgc gcgcgaacgc    300
accatggtgc gcgatccgcg ctattatggc atggatgtgt ggggccaggg caccaccgtg    360
accgtgagca gc                                                        372
```

<210> SEQ ID NO 52
<211> LENGTH: 321
<212> TYPE: DNA
<213> ORGANISM: Homo sapiens

<400> SEQUENCE: 52

```
gatattcaga tgacccagag cccggcgacc ctgagcctga gcccgggcga acgcgcgacc    60
ctgagctgcc gcgcgagcca gagcgtgagc agctatctgg cgtggtatca gcagcgcctg   120
ggccagagcc cgcgcctgct gatttatgat gcgagcagcc gcgcgaccgg cattccggcg   180
cgctttagcg gcagcggcag cggcaccgat tttaccctga ccattagcag cctgcagccg   240
gaagattttg cgacctatta ttgccagcag agctatagca acctggtgac ctttggccag   300
ggcacccgcc tggaaattaa a                                             321

<210> SEQ ID NO 53
<211> LENGTH: 378
<212> TYPE: DNA
<213> ORGANISM: Homo sapiens

<400> SEQUENCE: 53
gaagtgcagc tgctggaaag cggcggcggc ctggtgcagc cgggcggcag cctgcgcctg    60
agctgcgcgg cgagcggctt tacctttagc aactatatga tgacctgggt gcgccaggcg   120
ccgggcaaag gcctggaatg ggtgagcggc atttatccga gcggcggctt tacccagtat   180
gcggatagcg tgaaaggccg ctttaccatt agccgcgata acagcaaaaa cacccctgtat   240 ctgcagatga acagcctgcg cgcggaagat accgcgacct attattgcgc gcgcgatgcg   300
agcgatgtgt ggctgcgctt tcgcggcggc ggcgcgtttg atatttgggg ccagggcacc   360
atggtgaccg tgagcagc                                                 378

<210> SEQ ID NO 54
<211> LENGTH: 321
<212> TYPE: DNA
<213> ORGANISM: Homo sapiens

<400> SEQUENCE: 54
gatattcaga tgacccagag cccgaccagc ctgagcgcga gcgtgggcga tcgcgtggcg    60
attacctgcc gcgcgagcca gagcattgat acctatctga actggtatca gcagaaaccg   120
ggcaaagcgc cgaaactgct gatttatgat gcgagcaacc tggaaaccgg cgtgccgagc   180
cgctttagcg gcagcggcag cggcaccgat tttacccttta ccattagcag cctgcagccg   240
gaagatattg cgacctatta ttgccagcag tttgatgatc tgccgctgac ctttggcccg   300
ggcacccgcg tggatattaa a                                             321

<210> SEQ ID NO 55
<211> LENGTH: 372
<212> TYPE: DNA
<213> ORGANISM: Homo sapiens

<400> SEQUENCE: 55
gaagtgcagc tgctggaaag cggcggcggc ctggtgcagc cgggcggcag cctgcgcctg    60
agctgcgcgg cgagcggctt tacctttagc cgctatatta tgcattgggt gcgccaggcg   120
ccgggcaaag gcctggaatg ggtgagcagc attagcccga gcggcggcct gaccagctat   180
gcggatagcg tgaaaggccg ctttaccatt agccgcgata acagcaaaaa cacccctgtat   240 ctgcagatga acagcctgcg cgcggaagat accgcggtgt attattgcgc gcgcgaattt   300
gaaaacgcgt atcattatta ttattatggc atggatgtgt ggggccaggg caccaccgtg   360
accgtgagca gc                                                       372

<210> SEQ ID NO 56
<211> LENGTH: 321
```

<212> TYPE: DNA
<213> ORGANISM: Homo sapiens

<400> SEQUENCE: 56

```
gatattcaga tgacccagag cccgagcagc ctgagcgcga gcgtgggcga tcgcgtgacc      60
attacctgcc gcgcgagcgg cgatattggc aacgcgctgg gctggtatca gcagaaaccg     120
ggcaaagcgc cgcgcctgct gattagcgat gcgagcaccc tgcagagcgg cgtgccgctg     180
cgctttagcg gcagcggcag cggcaccgaa tttacccctga ccattagcag cctgcagccg    240
gaagattttg cgacctatta ttgcctgcag ggctataact atccgcgcac ctttggccag     300
ggcaccaaac tggaaattcg c                                              321
```

<210> SEQ ID NO 57
<211> LENGTH: 372
<212> TYPE: DNA
<213> ORGANISM: Homo sapiens

<400> SEQUENCE: 57

```
gaagtgcagc tgctggaaag cggcggcggc ctggtgcagc cgggcggcag cctgcgcctg      60
agctgcgcgg cgagcggctt tacctttagc cgctatatta tgcattgggt gcgccaggcg     120
ccgggcaaag gcctggaatg ggtgagcagc attagcccga gcggcggcct gaccagctat     180
gcggatagcg tgaaaggccg ctttaccatt agccgcgata cagcaaaaaa caccctgtat     240
ctgcagatga acagcctgcg cgcggaagat accgcggtgt attattgcgc gcgcgaattt     300
gaaaacgcgt atcattatta ttattatggc atggatgtgt ggggccaggg caccaccgtg     360
accgtgagca gc                                                        372
```

<210> SEQ ID NO 58
<211> LENGTH: 321
<212> TYPE: DNA
<213> ORGANISM: Homo sapiens

<400> SEQUENCE: 58

```
gatattcaga tgacccagag cccgagcagc ctgagcgcga gcgtgggcga tcgcgtgacc      60
attacctgcc gcgcgagcgg cgatattggc aacgcgctgg gctggtatca gcagaaaccg     120
ggcaaagcgc cgcgcctgct gattagcgat gcgagcaccc tgcagagcgg cgtgccgctg     180
cgctttagcg gcagcggcag cggcaccgaa tttacccctga ccattagcag cctgcagccg    240
gaagattttg cgacctatta ttgcctgcag ggctataact atccgcgcac ctttggccag     300
ggcaccaaac tggaaattcg c                                              321
```

<210> SEQ ID NO 59
<211> LENGTH: 378
<212> TYPE: DNA
<213> ORGANISM: Homo sapiens

<400> SEQUENCE: 59

```
gaagtgcagc tgctggaaag cggcggcggc ctggtgcagc cgggcggcag cctgcgcctg      60
agctgcgcgg cgagcggctt tacctttagc gaatatggca tgatttgggt gcgccaggcg     120
ccgggcaaag gcctggaatg ggtgagcttt attagcccga gcggcggcac cacctttttat   180
gcggatagcg tgaaaggccg ctttaccatt agccgcgata actttaaaaa caccctgtat     240
ctgcagatga acagcctgcg cgcggaagat accgcggtgt attattgcgc gcgcggcggc    300
ggcaactgga accatcgccg cgcgctgaac gatgcgtttg atatttgggg ccagggcacc    360
```

```
atggtgaccg tgagcagc                                                    378
```

<210> SEQ ID NO 60
<211> LENGTH: 321
<212> TYPE: DNA
<213> ORGANISM: Homo sapiens

<400> SEQUENCE: 60

```
gatattcaga tgacccagag cccgagcagc ctgagcgcga gcgtgggcga tcgcattacc      60
attacctgcc gcgcgagcca ggcgattcgc gatgattttg ctggtatca gcagaaaccg      120
ggcaaagcgc cgaaactgct gatttatgcg gcgagcagcc tgcagagcgg cgtgccgagc     180
cgctttagcg gcagcggcag cggcaccgat tttaccctga ccattagcag cctgcagccg     240
gaagattttg cgacctatta ttgccagcag agctatagca ccccgctgac ctttggcggc     300
ggcaccaaag tggaaattaa a                                              321
```

<210> SEQ ID NO 61
<211> LENGTH: 372
<212> TYPE: DNA
<213> ORGANISM: Homo sapiens

<400> SEQUENCE: 61

```
gaagtgcagc tgctggaaag cggcggcggc ctggtgcagc cgggcggcag cctgcgcctg      60
agctgcgcgg cgagcggctt tacctttagc acctatagca tgggctgggt gcgccaggcg     120
ccgggcaaag gcctggaatg ggtgagcagc attagcccga gcggcggcga taccgattat     180
gcggatagcg tgaaaggccg ctttaccatt agccgcgata acagcaaaaa caccctgtat     240
ctgcagatga acagcctgcg cgcggaagat accgcggtgt attattgcgc gcgcgaacgc     300
accatggtgc gcgatccgcg ctattatggc atggatgtgt ggggccaggg caccaccgtg     360
accgtgagca gc                                                         372
```

<210> SEQ ID NO 62
<211> LENGTH: 321
<212> TYPE: DNA
<213> ORGANISM: Homo sapiens

<400> SEQUENCE: 62

```
gatattcaga tgacccagag cccggcgacc ctgagcctga gcccgggcga acgcgcgacc      60
ctgagctgcc gcgcgagcca gagcgtgagc agctatctgg cgtggtatca gcagcgcctg     120
ggccagagcc cgcgcctgct gatttatgat gcgagcagcc gcgcgaccgg cattccggcg     180
cgctttagcg gcagcggcag cggcaccgat tttaccctga ccattagcag cctgcagccg     240
gaagattttg cgacctatta ttgccagcag agctatagca acctggtgac ctttggccag     300
ggcacccgcc tggaaattaa a                                              321
```

<210> SEQ ID NO 63
<211> LENGTH: 360
<212> TYPE: DNA
<213> ORGANISM: Homo sapiens

<400> SEQUENCE: 63

```
gaagtgcagc tgctggaaag cggcggcggc ctggtgcagc cgggcggcag cctgcgcctg      60
agctgcgcgg cgagcggctt tacctttagc cagtatggca tggattgggt gcgccaggcg     120
ccgggcaaag gcctggaatg ggtgagcggc attggcccga gcggcggcag caccgtgtat     180
gcggatagcg tgaaaggccg ctttaccatt agccgcgata acagcaaaaa caccctgtat     240
```
ctgcagatga acagcctgcg cgcggaagat accgcggtgt attattgcac ccgcggcggc    300
ccgtattatt attggggcat ggatgtgtgg ggccagggca ccaccgtgac cgtgagcagc    360

<210> SEQ ID NO 64
<211> LENGTH: 321
<212> TYPE: DNA
<213> ORGANISM: Homo sapiens

<400> SEQUENCE: 64
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacccttta ccattagcag cctgcagccg    240
gaagatattg cgacctatta ttgccagcag gcgaacagct ttccggtgac ctttggcggc    300
ggcaccaaag tggaaattaa a                                              321

<210> SEQ ID NO 65
<211> LENGTH: 360
<212> TYPE: DNA
<213> ORGANISM: Homo sapiens

<400> SEQUENCE: 65
gaagtgcagc tgctggaaag cggcggcggc ctggtgcagc cgggcggcag cctgcgcctg     60
agctgcgcgg cgagcggctt tacctttagc cagtatggca tggattgggt gcgccaggcg    120
ccgggcaaag gcctggaatg ggtgagcggc attggcccga gcggcggcag caccgtgtat    180
gcggatagcg tgaaaggccg ctttaccatt agccgcgata acagcaaaaa caccctgtat    240
ctgcagatga acagcctgcg cgcggaagat accgcggtgt attattgcac ccgcggcggc    300
ccgtattatt attatggcat ggatgtgtgg ggccagggca ccaccgtgac cgtgagcagc    360

<210> SEQ ID NO 66
<211> LENGTH: 321
<212> TYPE: DNA
<213> ORGANISM: Homo sapiens

<400> SEQUENCE: 66
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacccttta ccattagcag cctgcagccg    240
gaagatattg cgacctatta ttgccagcag gcggataacc tgccggtgac ctttggcggc    300
ggcaccaaag tggaaattaa a                                              321

<210> SEQ ID NO 67
<211> LENGTH: 360
<212> TYPE: DNA
<213> ORGANISM: Homo sapiens

<400> SEQUENCE: 67
gaagtgcagc tgctggaaag cggcggcggc ctggtgcagc cgggcggcag cctgcgcctg     60
agctgcgcgg cgagcggctt tacctttagc cagtatggca tggattgggt gcgccaggcg    120
ccgggcaaag gcctggaatg ggtgagcggc attggcccga gcggcggcag caccgtgtat    180

```
gcggatagcg tgaaaggccg ctttaccatt agccgcgata acagcaaaaa cacctgtat    240 ctgcagatga acagcctgcg cgcggaagat accgcggtgt attattgcac ccgcggcggc    300
ccgtattggt attatggcat ggatgtgtgg ggccagggca ccaccgtgac cgtgagcagc    360
```

<210> SEQ ID NO 68
<211> LENGTH: 321
<212> TYPE: DNA
<213> ORGANISM: Homo sapiens

<400> SEQUENCE: 68

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttaccttta ccattagcag cctgcagccg    240
gaagatattg cgacctatta ttgccagcag gcgaacagct ttccggtgac ctttggcggc    300
ggcaccaaag tggaaattaa a                                               321
```

<210> SEQ ID NO 69
<211> LENGTH: 360
<212> TYPE: DNA
<213> ORGANISM: Homo sapiens

<400> SEQUENCE: 69

```
gaagtgcagc tgctggaaag cggcggcggc ctggtgcagc cgggcggcag cctgcgcctg    60
agctgcgcgg cgagcggctt tacctttagc cagtatggca tggattgggt cgcccaggcg    120
ccgggcaaag gcctggaatg ggtgagcggc attggcccga gcggcggcag caccgtgtat    180
gcggatagcg tgaaaggccg ctttaccatt agccgcgata acagcaaaaa cacctgtat    240 ctgcagatga acagcctgcg cgcggaagat accgcggtgt attattgcac ccgcggcggc    300
ccgtattata gctatggcat ggatgtgtgg ggccagggca ccaccgtgac cgtgagcagc    360
```

<210> SEQ ID NO 70
<211> LENGTH: 321
<212> TYPE: DNA
<213> ORGANISM: Homo sapiens

<400> SEQUENCE: 70

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttaccttta ccattagcag cctgcagccg    240
gaagatattg cgacctatta ttgccagcag gcgaacagct ttccggtgac ctttggcggc    300
ggcaccaaag tggaaattaa a                                               321
```

<210> SEQ ID NO 71
<211> LENGTH: 360
<212> TYPE: DNA
<213> ORGANISM: Homo sapiens

<400> SEQUENCE: 71

```
gaagtgcagc tgctggaaag cggcggcggc ctggtgcagc cgggcggcag cctgcgcctg    60
agctgcgcgg cgagcggctt tacctttagc cagtatggca tggattgggt cgcccaggcg    120
ccgggcaaag gcctggaatg ggtgagcggc attggcccga gcggcggcag caccgtgtat    180
```

```
gcggatagcg tgaaaggccg ctttaccatt agccgcgata acagcaaaaa caccctgtat    240
ctgcagatga acagcctgcg cgcggaagat accgcggtgt attattgcac ccgcggcggc    300
ccgtattatt attatggcat ggatgtgtgg ggccagggca ccaccgtgac cgtgagcagc    360
```

<210> SEQ ID NO 72
<211> LENGTH: 321
<212> TYPE: DNA
<213> ORGANISM: Homo sapiens

<400> SEQUENCE: 72

```
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacctta ccattagcag cctgcagccg    240
gaagatattg cgacctatta ttgccagcag gcgaacaacc tgccggtgac ctttggcggc    300
ggcaccaaag tggaaattaa a                                              321
```

<210> SEQ ID NO 73
<211> LENGTH: 360
<212> TYPE: DNA
<213> ORGANISM: Homo sapiens

<400> SEQUENCE: 73

```
gaagtgcagc tgctggaaag cggcggcggc ctggtgcagc cgggcggcag cctgcgcctg     60
agctgcgcgg cgagcggctt tacctttagc cagtatggca tggattgggt gcgccaggcg    120
ccgggcaaag cctgaatg gtgagcggc attggcccga gcggcggcag caccgtgtat    180
gcggatagcg tgaaaggccg ctttaccatt agccgcgata acagcaaaaa caccctgtat    240
ctgcagatga acagcctgcg cgcggaagat accgcggtgt attattgcac ccgcggcggc    300
ggctattatt attatggcat ggatgtgtgg ggccagggca ccaccgtgac cgtgagcagc    360
```

<210> SEQ ID NO 74
<211> LENGTH: 321
<212> TYPE: DNA
<213> ORGANISM: Homo sapiens

<400> SEQUENCE: 74

```
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacctta ccattagcag cctgcagccg    240
gaagatattg cgacctatta ttgccagcag gcgaacagct ttccggtgac ctttggcggc    300
ggcaccaaag tggaaattaa a                                              321
```

<210> SEQ ID NO 75
<211> LENGTH: 360
<212> TYPE: DNA
<213> ORGANISM: Homo sapiens

<400> SEQUENCE: 75

```
gaagtgcagc tgctggaaag cggcggcggc ctggtgcagc cgggcggcag cctgcgcctg     60
agctgcgcgg cgagcggctt tacctttagc cagtatggca tggattgggt gcgccaggcg    120
```

```
ccgggcaaag gcctggaatg ggtgagcggc attggcccga gcggcggcag caccgtgtat    180
gcggatagcg tgaaaggccg ctttaccatt agccgcgata acagcaaaaa cacccctgtat   240 ctgcagatga acagcctgcg cgcggaagat accgcggtgt attattgcac ccgcggcggc    300
ccgtattatc gctatggcat ggatgtgtgg ggccagggca ccaccgtgac cgtgagcagc    360
```

<210> SEQ ID NO 76
<211> LENGTH: 321
<212> TYPE: DNA
<213> ORGANISM: Homo sapiens

<400> SEQUENCE: 76

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacccttta ccattagcag cctgcagccg   240
gaagatattg cgacctatta ttgccagcag gcgaacagct tccggtgac ctttggcggc     300 ggcaccaaag tggaaattaa a                                              321
```

<210> SEQ ID NO 77
<211> LENGTH: 360
<212> TYPE: DNA
<213> ORGANISM: Homo sapiens

<400> SEQUENCE: 77

```
gaagtgcagc tgctggaaag cggcggcggc ctggtgcagc cgggcggcag cctgcgcctg    60
agctgcgcgg cgagcggctt tacctttagc cagtatggca tggattgggt cgccaggcg    120 ccgggcaaag gcctggaatg ggtgagcggc attggcccga gcggcggcag caccgtgtat    180
gcggatagcg tgaaaggccg ctttaccatt agccgcgata acagcaaaaa cacccctgtat   240 ctgcagatga acagcctgcg cgcggaagat accgcggtgt attattgcac ccgcggcggc    300
ccgtattatt ggtatggcat ggatgtgtgg ggccagggca ccaccgtgac cgtgagcagc    360
```

<210> SEQ ID NO 78
<211> LENGTH: 321
<212> TYPE: DNA
<213> ORGANISM: Homo sapiens

<400> SEQUENCE: 78

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttaccttta ccattagcag cctgcagccg    240
gaagatattg cgacctatta ttgccagcag gcgaacagct tccggtgac ctttggcggc     300 ggcaccaaag tggaaattaa a                                              321
```

<210> SEQ ID NO 79
<211> LENGTH: 360
<212> TYPE: DNA
<213> ORGANISM: Homo sapiens

<400> SEQUENCE: 79

```
gaagtgcagc tgctggaaag cggcggcggc ctggtgcagc cgggcggcag cctgcgcctg    60
agctgcgcgg cgagcggctt tacctttagc cagtatggca tggattgggt cgccaggcg    120
```

```
ccgggcaaag gcctggaatg ggtgagcggc attggcccga gcggcggcag caccgtgtat    180
gcggatagcg tgaaaggccg ctttaccatt agccgcgata acagcaaaaa cacccthtat    240
```
(note: line 240 as shown)

<br/>

```
ccgggcaaag gcctggaatg ggtgagcggc attggcccga gcggcggcag caccgtgtat    180
gcggatagcg tgaaaggccg ctttaccatt agccgcgata acagcaaaaa cacccthtat    240
ctgcagatga acagcctgcg cgcggaagat accgcggtgt attattgcac ccgcggcggc    300
ccgtattata actatggcat ggatgtgtgg ggccagggca ccaccgtgac cgtgagcagc    360
```

<210> SEQ ID NO 80
<211> LENGTH: 321
<212> TYPE: DNA
<213> ORGANISM: Homo sapiens

<400> SEQUENCE: 80

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacccttta ccattagcag cctgcagccg    240
gaagatattg cgacctatta ttgccagcag gcgaacagct ttccggtgac ctttggcggc    300
ggcaccaaag tggaaattaa a                                              321
```

<210> SEQ ID NO 81
<211> LENGTH: 360
<212> TYPE: DNA
<213> ORGANISM: Homo sapiens

<400> SEQUENCE: 81

```
gaagtgcagc tgctggaaag cggcggcggc ctggtgcagc cgggcggcag cctgcgcctg    60
agctgcgcgg cgagcggctt tacctttagc cagtatggca tggattgggt gcgccaggcg    120
ccgggcaaag gcctggaatg ggtgagcggc attggcccga gcggcggcag caccgtgtat    180
gcggatagcg tgaaaggccg ctttaccatt agccgcgata acagcaaaaa cacccthtat    240
ctgcagatga acagcctgcg cgcggaagat accgcggtgt attattgcac ccgcggcggc    300
ccgtattatt atcagggcat ggatgtgtgg ggccagggca ccaccgtgac cgtgagcagc    360
```

<210> SEQ ID NO 82
<211> LENGTH: 321
<212> TYPE: DNA
<213> ORGANISM: Homo sapiens

<400> SEQUENCE: 82

```
gatattcaga tgacccagag cccgagcagc ctgagcgcga gcgtgggcga tcgcgtgacc    60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacccttta ccattagcag cctgcagccg    240
gaagatattg cgacctatta ttgccagcag gcgaacagct ttccggtgac ctttggcggc    300
ggcaccaaag tggaaattaa a                                              321
```

<210> SEQ ID NO 83
<211> LENGTH: 360
<212> TYPE: DNA
<213> ORGANISM: Homo sapiens

<400> SEQUENCE: 83

```
gaagtgcagc tgctggaaag cggcggcggc ctggtgcagc cgggcggcag cctgcgcctg    60
```

```
agctgcgcgg cgagcggctt tacctttagc cagtatggca tggattgggt gcgccaggcg    120
ccgggcaaag gcctggaatg ggtgagcggc attggcccga gcggcggcag caccgtgtat    180
gcggatagcg tgaaaggccg ctttaccatt agccgcgata acagcaaaaa caccctgtat    240
ctgcagatga acagcctgcg cgcggaagat accgcggtgt attattgcac ccgcggcggc    300
ccgtattatt ataaaggcat ggatgtgtgg ggccagggca ccaccgtgac cgtgagcagc    360
```

<210> SEQ ID NO 84
<211> LENGTH: 321
<212> TYPE: DNA
<213> ORGANISM: Homo sapiens

<400> SEQUENCE: 84

```
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacctttta ccattagcag cctgcagccg    240
gaagatattg cgacctatta ttgccagcag gcgaacagct ttccggtgac ctttggcggc    300
ggcaccaaag tggaaattaa a                                               321
```

<210> SEQ ID NO 85
<211> LENGTH: 360
<212> TYPE: DNA
<213> ORGANISM: Homo sapiens

<400> SEQUENCE: 85

```
gaagtgcagc tgctggaaag cggcggcggc ctggtgcagc cgggcggcag cctgcgcctg     60
agctgcgcgg cgagcggctt tacctttagc cagtatggca tggattgggt gcgccaggcg    120
ccgggcaaag gcctggaatg ggtgagcggc attggcccga gcggcggcag caccgtgtat    180
gcggatagcg tgaaaggccg ctttaccatt agccgcgata acagcaaaaa caccctgtat    240
ctgcagatga acagcctgcg cgcggaagat accgcggtgt attattgcac ccgcggcggc    300
ccgtattatt atgtgggcat ggatgtgtgg ggccagggca ccaccgtgac cgtgagcagc    360
```

<210> SEQ ID NO 86
<211> LENGTH: 321
<212> TYPE: DNA
<213> ORGANISM: Homo sapiens

<400> SEQUENCE: 86

```
gatattcaga tgacccagag cccgagcagc ctgagcgcga gcgtgggcga tcgcgtgacc     60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttaccttta ccattagcag cctgcagccg    240
gaagatattg cgacctatta ttgccagcag gcgaacagct ttccggtgac ctttggcggc    300
ggcaccaaag tggaaattaa a                                               321
```

<210> SEQ ID NO 87
<211> LENGTH: 360
<212> TYPE: DNA
<213> ORGANISM: Homo sapiens

<400> SEQUENCE: 87

```
gaagtgcagc tgctggaaag cggcggcggc ctggtgcagc cgggcggcag cctgcgcctg     60
```

```
agctgcgcgg cgagcggctt tacctttagc cagtatggca tggattgggt gcgccaggcg     120
ccgggcaaag gcctggaatg ggtgagcggc attggcccga gcgcggcag caccgtgtat      180 gcggatagcg tgaaaggccg ctttaccatt agccgcgata acagcaaaaa cacccctgtat    240 ctgcagatga acagcctgcg cgcggaagat accgcggtgt attattgcac ccgcggcggc    300
ccgtattatg cgtatggcat ggatgtgtgg ggccagggca ccaccgtgac cgtgagcagc     360
```

<210> SEQ ID NO 88
<211> LENGTH: 321
<212> TYPE: DNA
<213> ORGANISM: Homo sapiens

<400> SEQUENCE: 88

```
gatattcaga tgacccagag cccgagcagc ctgagcgcga gcgtgggcga tcgcgtgacc      60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacctttta ccattagcag cctgcagccg    240
gaagatattg cgacctatta ttgccagcag gcgaacagct tccggtgac ctttggcggc     300 ggcaccaaag tggaaattaa a                                               321
```

<210> SEQ ID NO 89
<211> LENGTH: 360
<212> TYPE: DNA
<213> ORGANISM: Homo sapiens

<400> SEQUENCE: 89

```
gaagtgcagc tgctggaaag cggcggcggc ctggtgcagc cgggcggcag cctgcgcctg      60
agctgcgcgg cgagcggctt tacctttagc acctattgga tgacctgggt gcgccaggcg    120
ccgggcaaag gcctggaatg ggtgagcagc atttggagca gcggcggctg gacccctgtat   180 gcggatagcg tgaaaggccg ctttaccatt agccgcgata acagcaaaaa cacccctgtat    240 ctgcagatga acagcctgcg cgcggaagat accgcggtgt attattgcgc gcgcgaagtg    300
ggcgcggcgg gctttgcgtt tgatatttgg ggccagggca ccatggtgac cgtgagcagc    360
```

<210> SEQ ID NO 90
<211> LENGTH: 321
<212> TYPE: DNA
<213> ORGANISM: Homo sapiens

<400> SEQUENCE: 90

```
gatattcaga tgacccagag cccgagcagc ctgagcgcga gcgtgggcga tcgcgtgacc      60
attacctgcc aggcgagcca ggatattagc aactatctga actggtatca gcagaaaccg    120
ggcaaagcgc cgaaactgct gatttatgat gcgagcaacc tggaaaccgg cgtgccgagc    180
cgctttagcg gcagcggcag cggcaccgat tttacctttta ccattagcag cctgcagccg    240
gaagatattg cgacctatta ttgccagcag agcagcagca cccccgctgac ctttggcggc    300 ggcaccaaaa tggaaattaa a                                               321
```

<210> SEQ ID NO 91
<211> LENGTH: 366
<212> TYPE: DNA
<213> ORGANISM: Homo sapiens

<400> SEQUENCE: 91

```
gaagtgcagc tgctggaaag cggcggcggc ctggtgcagc cgggcggcag cctgcgcctg    60
agctgcgcgg cgagcggctt tacctttagc acctatgaaa tgaactgggt gcgccaggcg   120
ccgggcaaag gcctggaatg ggtgagctgg attggcccga gcggcggctt tacctttat   180 gcggatagcg tgaaaggccg ctttaccatt agccgcgata acagcaaaaa caccctgtat   240
ctgcagatga acagcctgcg cgcggaagat accgcggtgt attattgcgc gaaagataaa   300
gcggtggcgg catgggcga agcgtttgat atttggggcc agggcaccat ggtgaccgtg   360
agcagc                                                              366
```

<210> SEQ ID NO 92  
<211> LENGTH: 321  
<212> TYPE: DNA  
<213> ORGANISM: Homo sapiens
<400> SEQUENCE: 92

```
gatattcaga tgacccagag cccgagcagc ctgagcgcga gcgtgggcga tcgcgtgacc    60
attacctgcc aggcgagcca ggatattagc atttatctga actggtatca gcagaaaccg   120
ggcaaagcgc cgaaactgct gatttatgat gcgagcaacg tggaaaccgg cgtgccgagc   180
cgctttagcg gcagcggcag cggcaccgat tttacctttta ccattagcag cctgcagccg   240
gaagatattg cgacctatta ttgccagcag tttataacc tgccgctgac ctttggcggc   300
ggcaccaaag tggaaattaa a                                             321
```

<210> SEQ ID NO 93  
<211> LENGTH: 354  
<212> TYPE: DNA  
<213> ORGANISM: Homo sapiens
<400> SEQUENCE: 93

```
gaagtgcagc tgctggaaag cggcggcggc ctggtgcagc cgggcggcag cctgcgcctg    60
agctgcgcgg cgagcggctt tacctttagc gattatgaaa tggcgtgggt gcgccaggcg   120
ccgggcaaag gcctggaatg ggtgagcagc attgtgccga gcggcggctg accctgtat    180 gcggatagcg tgaaaggccg ctttaccatt agccgcgata acagcaaaaa caccctgtat   240
ctgcagatga acagcctgcg cgcggaagat accgcggtgt attattgcgc gacctggggc   300
gatagctggg gctttgatt ttggggccag ggcacctgg tgaccgtgag cagc           354
```

<210> SEQ ID NO 94  
<211> LENGTH: 321  
<212> TYPE: DNA  
<213> ORGANISM: Homo sapiens
<400> SEQUENCE: 94

```
gatattcaga tgacccagag cccgagcagc gtgagcgcga gcgtgggcga tcgcgtgacc    60
attacctgcc gcgcgagcca gggcattagc agctggctgg cgtggtatca gcagcgcccg   120
ggcaaagcgc cgaaactgct gatttatgat gcgagcaccc tgcagagcgg cgtgccgagc   180
cgctttagcg gcagcggcag cggcaccgat tttaccctga ccattaacag cctgcagccg   240
gaaaactttg cgacctatta ttgccagcag gcggatagct ttccgattgc gtttggccag   300
ggcacccgcc tggaaattaa a                                             321
```

<210> SEQ ID NO 95  
<211> LENGTH: 375  
<212> TYPE: DNA  
<213> ORGANISM: Homo sapiens

<400> SEQUENCE: 95

```
gaagtgcagc tgctggaaag cggcggcggc ctggtgcagc cgggcggcag cctgcgcctg    60
agctgcgcgg cgagcggctt tacctttagc ccgtatgata tgtattgggt gcgccaggcg   120
ccgggcaaag gcctggaatg ggtgagctat atttggagca gcggcggcat tacccagtat   180
gcggatagcg tgaaaggccg ctttaccatt agccgcgata acagcaaaaa caccctgtat   240
ctgcagatga acagcctgcg cgcggaagat accgcggtgt attattgcgc gcgccatgcg   300
agctattatg atagcagcgg ccgcccggat gcgtttgata tttggggcca gggcaccatg   360
gtgaccgtga gcagc                                                    375
```

<210> SEQ ID NO 96
<211> LENGTH: 321
<212> TYPE: DNA
<213> ORGANISM: Homo sapiens

<400> SEQUENCE: 96

```
gatattcaga tgacccagag cccgagcagc ctgagcgcga gcgtgggcga tcgcgtgacc    60
attacctgcc gcgcgagcca gagcattagc agctatgtga actggtatca gcagaaaccg   120
ggcaaagcgc cgaacctgct gatttatgcg gcgagcagcc tggaaagcgg cgtgccgagc   180
cgctttagcg gcagcggcag cggcaccgat tttaccctga ccattagcag cctgcagccg   240
gaagattttg cgacctatta ttgccagcag agctatagca ccccgtatac ctttggccag   300
ggcaccaaac tggatattaa a                                             321
```

<210> SEQ ID NO 97
<211> LENGTH: 375
<212> TYPE: DNA
<213> ORGANISM: Homo sapiens

<400> SEQUENCE: 97

```
gaagtgcagc tgctggaaag cggcggcggc ctggtgcagc cgggcggcag cctgcgcctg    60
agctgcgcgg cgagcggctt tacctttagc cattatagca tgcagtgggt gcgccaggcg   120
ccgggcaaag gcctggaatg ggtgagcagc attagcccga gcggcggcta taccatgtat   180
gcggatagcg tgaaaggccg ctttaccatt agccgcgata acagcaaaaa caccctgtat   240
ctgcagatga acagcctgcg cgcggaagat accgcgatgt attattgcgc gcgcgaaaaa   300
gcgagcgatc tgagcggcac ctatagcgaa gcgctggatt attggggcca gggcaccctg   360
gtgaccgtga gcagc                                                    375
```

<210> SEQ ID NO 98
<211> LENGTH: 324
<212> TYPE: DNA
<213> ORGANISM: Homo sapiens

<400> SEQUENCE: 98

```
gatattcaga tgacccagag cccgagcagc ctgagcgcga gcgtgggcga tcgcgtgacc    60
attacctgcc aggcgagcca ggatattgat tattatctga actggtatca gcagcagccg   120
ggcaaagcgc cgcagctgct gatttatgat gcgagcaacc tggaaaccgg cgtgccgagc   180
cgctttagcg gcagcggcag cggcaccgat tttacccttta ccattagcag cctgcatccg   240
gaagattttg cgacctatta ttgccagcag tatcataccc tgccgccgct gacctttggc   300
ggcggcacca aagtggatat taaa                                          324
```

<210> SEQ ID NO 99
<211> LENGTH: 363
<212> TYPE: DNA
<213> ORGANISM: Homo sapiens

<400> SEQUENCE: 99
gaagtgcagc tgctggaaag cggcggcggc ctggtgcagc cgggcggcag cctgcgcctg      60
agctgcgcgg cgagcggctt tacctttagc ccgtattgga tgcattgggt gcgccaggcg     120
ccgggcaaag gcctggaatg ggtgagcagc atttatagca gcggcggctg gaccgattat     180
gcggatagcg tgaaaggccg ctttaccatt agccgcgata acagcaaaaa caccctgtat     240
ctgcagatga acagcctgcg cgcggaagat accgcggtgt attattgcgc gcgcgaaggc     300
gtggcgggca ccaacgatgc gtttgatatt tggggccagg gcaccatggt gaccgtgagc     360
agc                                                                  363

<210> SEQ ID NO 100
<211> LENGTH: 324
<212> TYPE: DNA
<213> ORGANISM: Homo sapiens

<400> SEQUENCE: 100
gatattcaga tgacccagag cccgctgagc ctgagcgcga gcgtgggcga tcgcgtgacc      60
attacctgcc gcgcgagcca gagcattagc agctatctga actggtatca gcagaaaccg     120
ggcaaagcgc cgaaactgct gatttatgcg gcgagcagcc tgcagagcgg cgtgccgagc     180
cgctttagcg gcagcggcag cggcaccgat tttaccctga ccattagcag cctgcagccg     240
gaagattttg cgacctatta ttgccagcag agctatagca ccccgccgtg gacctttggc     300
cagggcacca aagtggaaat taaa                                           324

<210> SEQ ID NO 101
<211> LENGTH: 354
<212> TYPE: DNA
<213> ORGANISM: Homo sapiens

<400> SEQUENCE: 101
gaagtgcagc tgctggaaag cggcggcggc ctggtgcagc cgggcggcag cctgcgcctg      60
agctgcgcgg cgagcggctt tacctttagc gattatgaaa tggcgtgggt gcgccaggcg     120
ccgggcaaag gcctggaatg ggtgagcagc attgtgccga gcggcggctg gacccgtgtat    180 gcggatagcg tgaaaggccg ctttaccatt agccgcgata acagcaaaaa caccctgtat     240
ctgcagatga acagcctgcg cgcggaagat accgcggtgt attattgcgc gacctggggc     300
gatagctggg gctttgattt ttggggccag ggcacccctgg tgaccgtgag cagc          354

<210> SEQ ID NO 102
<211> LENGTH: 321
<212> TYPE: DNA
<213> ORGANISM: Homo sapiens

<400> SEQUENCE: 102
gatattcaga tgacccagag cccgagcagc gtgagcgcga gcgtgggcga tcgcgtgacc      60
attacctgcc gcgcgagcca gggcattagc agctggctgg cgtggtatca gcagaaaccg     120
ggcaaagcgc cgaaactgct gatttatgat gcgagcaccc tgcagagcgg cgtgccgagc     180
cgctttagcg gcagcggcag cggcaccgat tttaccctga ccattaacag cctgcagccg     240
gaaaactttg cgacctatta ttgccagcag gcggatagct ttccgattgc gtttggccag     300

```
ggcacccgcc tggaaattaa a                                              321
```

<210> SEQ ID NO 103
<211> LENGTH: 354
<212> TYPE: DNA
<213> ORGANISM: Homo sapiens

<400> SEQUENCE: 103

```
gaagtgcagc tgctggaaag cggcggcggc ctggtgcagc cgggcggcag cctgcgcctg    60
agctgcgcgg cgagcggctt tacctttagc gattatgaaa tggcgtgggt gcgccaggcg   120
ccgggcaaag gcctggaatg ggtgagcagc attgtgccga gcggcggctg gaccctgtat   180
gcggatagcg tgaaaggccg ctttaccatt agccgcgata cagcaaaaa caccctgtat   240
ctgcagatga acagcctgcg cgcggaagat accgcggtgt attattgcgc gacctggggc   300
gatagctggg gctttgattt ttggggccag ggcaccctgg tgaccgtgag cagc         354
```

<210> SEQ ID NO 104
<211> LENGTH: 321
<212> TYPE: DNA
<213> ORGANISM: Homo sapiens

<400> SEQUENCE: 104

```
gatattcaga tgacccagag cccgagcagc gtgagcgcga gcgtgggcga tcgcgtgacc    60
attacctgcc gcgcgagcca gggcattagc agctggctgg cgtggtatca gcagcgcccg   120
ggcaaagcgc cgaaactgct gatttatgat gcgagcagcc tgcagagcgg cgtgccgagc   180
cgctttagcg gcagcggcag cggcaccgat tttaccctga ccattaacag cctgcagccg   240
gaaaactttg cgacctatta ttgccagcag gcggatagct ttccgattgc gtttggccag   300
ggcacccgcc tggaaattaa a                                              321
```

<210> SEQ ID NO 105
<211> LENGTH: 354
<212> TYPE: DNA
<213> ORGANISM: Homo sapiens

<400> SEQUENCE: 105

```
gaagtgcagc tgctggaaag cggcggcggc ctggtgcagc cgggcggcag cctgcgcctg    60
agctgcgcgg cgagcggctt tacctttagc gattatgaaa tggcgtgggt gcgccaggcg   120
ccgggcaaag gcctggaatg ggtgagcagc attgtgccga gcggcggctg gaccctgtat   180
gcggatagcg tgaaaggccg ctttaccatt agccgcgata cagcaaaaa caccctgtat   240
ctgcagatga acagcctgcg cgcggaagat accgcggtgt attattgcgc gacctggggc   300
gatagctggg gctttgattt ttggggccag ggcaccctgg tgaccgtgag cagc         354
```

<210> SEQ ID NO 106
<211> LENGTH: 321
<212> TYPE: DNA
<213> ORGANISM: Homo sapiens

<400> SEQUENCE: 106

```
gatattcaga tgacccagag cccgagcagc gtgagcgcga gcgtgggcga tcgcgtgacc    60
attacctgcc gcgcgagcca gggcattagc agctggctgg cgtggtatca gcagcgcccg   120
ggcaaagcgc cgaaactgct gatttatgat gcgagcaccc tgcagagcgg cgtgccgagc   180
cgctttagcg gcagcggcag cggcaccgat tttaccctga ccattaacag cctgcagccg   240
```

```
gaagattttg cgacctatta ttgccagcag gcggatagct ttccgattgc gtttggccag    300
ggcacccgcc tggaaattaa a                                              321

<210> SEQ ID NO 107
<211> LENGTH: 354
<212> TYPE: DNA
<213> ORGANISM: Homo sapiens

<400> SEQUENCE: 107
gaagtgcagc tgctggaaag cggcggcggc ctggtgcagc cgggcggcag cctgcgcctg     60
agctgcgcgg cgagcggctt tacctttagc gattatgaaa tggcgtgggt gcgccaggcg    120
ccgggcaaag gcctggaatg ggtgagcagc attgtgccga gcggcggctg gaccctgtat    180
gcggatagcg tgaaaggccg ctttaccatt agccgcgata acagcaaaaa caccctgtat    240
ctgcagatga acagcctgcg cgcggaagat accgcggtgt attattgcgc gacctggggc    300
gatagctggg gctttgattt ttggggccag ggcaccctgg tgaccgtgag cagc          354

<210> SEQ ID NO 108
<211> LENGTH: 321
<212> TYPE: DNA
<213> ORGANISM: Homo sapiens

<400> SEQUENCE: 108
gatattcaga tgacccagag cccgagcagc gtgagcgcga gcgtgggcga tcgcgtgacc     60
attacctgcc gcgcgagcca gggcattagc agctggctgg cgtggtatca gcagcgcccg    120
ggcaaagcgc cgaaactgct gatttatgat gcgagcaccc tgcagagcgg cgtgccgagc    180
cgctttagcg gcagcggcag cggcaccgat tttaccctga ccattaacag cctgcagccg    240
gaaaactttg cgacctatta ttgccagcag gcggatagct ttccgattac ctttggccag    300
ggcacccgcc tggaaattaa a                                              321

<210> SEQ ID NO 109
<211> LENGTH: 354
<212> TYPE: DNA
<213> ORGANISM: Homo sapiens

<400> SEQUENCE: 109
gaagtgcagc tgctggaaag cggcggcggc ctggtgcagc cgggcggcag cctgcgcctg     60
agctgcgcgg cgagcggctt tacctttagc gattatgaaa tggcgtgggt gcgccaggcg    120
ccgggcaaag gcctggaatg ggtgagcagc attgtgccga gcggcggctg gaccctgtat    180
gcggatagcg tgaaaggccg ctttaccatt agccgcgata acagcaaaaa caccctgtat    240
ctgcagatga acagcctgcg cgcggaagat accgcggtgt attattgcgc gacctggggc    300
gatagctggg gctttgattt ttggggccag ggcaccctgg tgaccgtgag cagc          354

<210> SEQ ID NO 110
<211> LENGTH: 321
<212> TYPE: DNA
<213> ORGANISM: Homo sapiens

<400> SEQUENCE: 110
gatattcaga tgacccagag cccgagcagc gtgagcgcga gcgtgggcga tcgcgtgacc     60
attacctgcc gcgcgagcca gggcattagc agctggctgg cgtggtatca gcagaaaccg    120
ggcaaagcgc cgaaactgct gatttatgat gcgagcaccc tgcagagcgg cgtgccgagc    180
cgctttagcg gcagcggcag cggcaccgat tttaccctga ccattaacag cctgcagccg    240
```

```
gaagattttg cgacctatta ttgccagcag gcggatagct ttccgattgc gtttggccag    300
ggcacccgcc tggaaattaa a                                              321
```

<210> SEQ ID NO 111
<211> LENGTH: 124
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ile Met His Trp Val Arg Gln Ala Pro Gly Lys Gly Leu Glu Trp Val
        35                  40                  45

Ser Ser Ile Ser Pro Ser Gly Gly Leu Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Glu Asn Ala Tyr His Tyr Tyr Tyr Gly Met Asp
            100                 105                 110

Val Trp Gly Gln Gly Thr Thr Val Thr Val Ser Ser
        115                 120

<210> SEQ ID NO 112
<211> LENGTH: 107
<212> TYPE: PRT
<213> ORGANISM: Homo sapiens

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asp Ile Gly Asn Ala
            20                  25                  30

Leu Gly Trp Tyr Gln Gln Lys Pro Gly Lys Ala Pro Arg Leu Leu Ile
        35                  40                  45

Ser Asp Ala Ser Thr Leu Gln Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Gly Tyr Asn Tyr Pro Arg
                85                  90                  95

Thr Phe Gly Gln Gly Thr Lys Leu Glu Ile Arg
            100                 105

<210> SEQ ID NO 113
<211> LENGTH: 124
<212> TYPE: PRT
<213> ORGANISM: Homo sapiens

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

```
Pro Met Gln Trp Val Arg Gln Ala Pro Gly Lys Gly Leu Glu Trp Val
            35                  40                  45

Ser Gly Ile Ser Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Tyr Ser Asn Tyr Val Met Asp Leu Gly Leu Asp
            100                 105                 110

Tyr Trp Gly Gln Gly Thr Leu Val Thr Val Ser Ser
            115                 120
```

<210> SEQ ID NO 114
<211> LENGTH: 107
<212> TYPE: PRT
<213> ORGANISM: Homo sapiens

<400> SEQUENCE: 114

```
Asp Ile Gln Met Thr Gln Ser Pro Ala Thr Leu Ser Leu Ser Ala Gly
1               5                   10                  15

Glu Arg Ala Thr Leu Ser Cys Arg Ala Ser Gln Thr Val Ser Ser Ser
            20                  25                  30

Leu Ala Trp Tyr Gln His Lys Pro Gly Gln Ala Pro Arg Leu Leu Ile
            35                  40                  45

Tyr Glu Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Pro Gly Thr Lys Val Asp Ile Lys
            100                 105
```

<210> SEQ ID NO 115
<211> LENGTH: 124
<212> TYPE: PRT
<213> ORGANISM: Homo sapiens

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Gly Trp Val Arg Gln Ala Pro Gly Lys Gly Leu Glu Trp Val
            35                  40                  45

Ser Ser Ile Ser Pro Ser Gly Gly Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Met Val Arg Asp Pro Arg Tyr Tyr Gly Met Asp
            100                 105                 110

Val Trp Gly Gln Gly Thr Thr Val Thr Val Ser Ser
            115                 120
```

<210> SEQ ID NO 116
<211> LENGTH: 107
<212> TYPE: PRT
<213> ORGANISM: Homo sapiens

<400> SEQUENCE: 116

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Leu Gly Gln Ser Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Leu Val
                85                  90                  95

Thr Phe Gly Gln Gly Thr Arg Leu Glu Ile Lys
            100                 105

<210> SEQ ID NO 117
<211> LENGTH: 124
<212> TYPE: PRT
<213> ORGANISM: Homo sapiens

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Tyr Met Lys Trp Val Arg Gln Ala Pro Gly Lys Gly Leu Glu Trp Val
        35                  40                  45

Ser Ser Ile Ser Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Glu Asn Ala Tyr His Tyr Tyr Tyr Gly Met Asp
            100                 105                 110

Val Trp Gly Gln Gly Thr Thr Val Thr Val Ser Ser
        115                 120

<210> SEQ ID NO 118
<211> LENGTH: 107
<212> TYPE: PRT
<213> ORGANISM: Homo sapiens

<400> SEQUENCE: 118

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Asn Ile Trp
            20                  25                  30

Leu Ala Trp Tyr Gln Gln Lys Pro Gly Lys Ala Pro Lys Leu Leu Ile
        35                  40                  45

```
Ser Ala Ala Ser Thr Val Gln Ser Gly Val Pro Ser Arg Phe Ser Gly
         50                  55                  60

Ser Gly Ser Gly Thr Asp Phe Thr Leu Thr Ile Asn Thr Leu Gln Pro
 65              70                  75                      80

Asp Asp Phe Ala Thr Tyr Tyr Cys Gln Gln Ala Ala Ser Phe Pro Leu
                 85                  90                  95

Thr Phe Gly Gly Gly Thr Lys Val Glu Met Lys
            100                 105
```

<210> SEQ ID NO 119
<211> LENGTH: 124
<212> TYPE: PRT
<213> ORGANISM: Homo sapiens

<400> SEQUENCE: 119

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ser Met Gly Trp Val Arg Gln Ala Pro Gly Lys Gly Leu Glu Trp Val
         35                  40                  45

Ser Ser Ile Ser Pro Ser Gly Gly Asp Thr Asp Tyr Ala Asp Ser Val
 50                  55                  60

Lys Gly Arg Phe Thr Ile Ser Arg Asp Asn Ser Lys Asn Thr Leu Tyr
 65              70                  75                      80

Leu Gln Met Asn Ser Leu Arg Ala Glu Asp Thr Ala Val Tyr Tyr Cys
                 85                  90                  95

Ala Arg Glu Arg Thr Met Val Arg Asp Pro Arg Tyr Tyr Gly Met Asp
            100                 105                 110

Val Trp Gly Gln Gly Thr Thr Val Thr Val Ser Ser
            115                 120
```

<210> SEQ ID NO 120
<211> LENGTH: 107
<212> TYPE: PRT
<213> ORGANISM: Homo sapiens

<400> SEQUENCE: 120

```
Asp Ile Gln Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Arg Leu Gly Gln Ser Pro Arg Leu Leu Ile
         35                  40                  45

Tyr Asp Ala Ser Arg Ala Thr Gly Ile Pro Ala Arg Phe Ser Gly
 50                  55                  60

Ser Gly Ser Gly Thr Asp Phe Thr Leu Thr Ile Ser Ser Leu Gln Pro
 65              70                  75                      80

Lys Asp Phe Ala Thr Tyr Tyr Cys Gln Gln Ser Tyr Ser Asn Leu Val
                 85                  90                  95

Thr Phe Gly Gln Gly Thr Arg Leu Glu Ile Lys
            100                 105
```

<210> SEQ ID NO 121
<211> LENGTH: 124
<212> TYPE: PRT
<213> ORGANISM: Homo sapiens -continued

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Gln Trp Val Arg Gln Ala Pro Gly Lys Gly Leu Glu Trp Val
        35                  40                  45

Ser Gly Ile Ser Ser Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Gly Tyr Ser Asn Tyr Val Met Asp Leu Gly Leu Asp
            100                 105                 110

Tyr Trp Gly Gln Gly Thr Leu Val Thr Val Ser Ser
        115                 120

<210> SEQ ID NO 122
<211> LENGTH: 107
<212> TYPE: PRT
<213> ORGANISM: Homo sapiens

<400> SEQUENCE: 122

Asp Ile Gln Met Thr Gln Ser Pro Ala Thr Leu Ser Leu Ser Ala Gly
1               5                   10                  15

Glu Arg Ala Thr Leu Ser Cys Arg Ala Ser Gln Thr Val Ser Ser Ser
            20                  25                  30

Leu Ala Trp Tyr Gln His Lys Pro Gly Gln Ala Pro Arg Leu Leu Ile
            35                  40                  45

Tyr Glu Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Pro Gly Thr Lys Val Asp Ile Lys
            100                 105

<210> SEQ ID NO 123
<211> LENGTH: 124
<212> TYPE: PRT
<213> ORGANISM: Homo sapiens

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Pro Met Gln Trp Val Arg Gln Ala Pro Gly Lys Gly Leu Glu Trp Val
        35                  40                  45

Ser Gly Ile Ser Ser Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys 85                  90                  95

Ala Arg Asp Trp Gly Tyr Ser Asn Tyr Val Met Asp Leu Gly Leu Asp
                100                 105                 110

Tyr Trp Gly Gln Gly Thr Leu Val Thr Val Ser Ser
            115                 120

<210> SEQ ID NO 124
<211> LENGTH: 107
<212> TYPE: PRT
<213> ORGANISM: Homo sapiens

<400> SEQUENCE: 124

Asp Ile Gln Met Thr Gln Ser Pro Ala Thr Leu Ser Leu Ser Ala Gly
1               5                   10                  15

Glu Arg Ala Thr Leu Ser Cys Arg Ala Ser Gln Thr Val Ser Ser Ser
            20                  25                  30

Leu Ala Trp Tyr Gln His Lys Pro Gly Gln Ala Pro Arg Leu Leu Ile
        35                  40                  45

Tyr Glu Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Pro Gly Thr Lys Val Asp Ile Lys
            100                 105

<210> SEQ ID NO 125
<211> LENGTH: 124
<212> TYPE: PRT
<213> ORGANISM: Homo sapiens

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Gly Trp Val Arg Gln Ala Pro Gly Lys Gly Leu Glu Trp Val
        35                  40                  45

Ser Ser Ile Ser Pro Ser Gly Gly Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Met Val Arg Asp Pro Arg Tyr Tyr Gly Met Asp
            100                 105                 110

Val Trp Gly Gln Gly Thr Thr Val Thr Val Ser Ser
        115                 120

<210> SEQ ID NO 126
<211> LENGTH: 107
<212> TYPE: PRT
<213> ORGANISM: Homo sapiens

<400> SEQUENCE: 126

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Leu Gly Gln Ser Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Leu Val
                85                  90                  95

Thr Phe Gly Gln Gly Thr Arg Leu Glu Ile Lys
            100                 105

<210> SEQ ID NO 127
<211> LENGTH: 126
<212> TYPE: PRT
<213> ORGANISM: Homo sapiens

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Met Met Thr Trp Val Arg Gln Ala Pro Gly Lys Gly Leu Glu Trp Val
        35                  40                  45

Ser Gly Ile Tyr Pro Ser Gly Gly Phe Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Asp Ala Ser Asp Val Trp Leu Arg Phe Arg Gly Gly Gly Ala
            100                 105                 110

Phe Asp Ile Trp Gly Gln Gly Thr Met Val Thr Val Ser Ser
        115                 120                 125

<210> SEQ ID NO 128
<211> LENGTH: 107
<212> TYPE: PRT
<213> ORGANISM: Homo sapiens

<400> SEQUENCE: 128

Asp Ile Gln Met Thr Gln Ser Pro Thr Ser Leu Ser Ala Ser Val Gly
1               5                   10                  15

Asp Arg Val Ala Ile Thr Cys Arg Ala Ser Gln Ser Ile Asp Thr Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Phe Thr Ile Ser Ser Leu Gln Pro
65                  70                  75                  80

Glu Asp Ile Ala Thr Tyr Tyr Cys Gln Gln Phe Asp Asp Leu Pro Leu
                85                  90                  95

Thr Phe Gly Pro Gly Thr Arg Val Asp Ile Lys
            100                 105

<210> SEQ ID NO 129
<211> LENGTH: 124
<212> TYPE: PRT
<213> ORGANISM: Homo sapiens

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ile Met His Trp Val Arg Gln Ala Pro Gly Lys Gly Leu Glu Trp Val
        35                  40                  45

Ser Ser Ile Ser Pro Ser Gly Gly Leu Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Glu Asn Ala Tyr His Tyr Tyr Tyr Tyr Gly Met Asp
            100                 105                 110

Val Trp Gly Gln Gly Thr Thr Val Thr Val Ser Ser
        115                 120

<210> SEQ ID NO 130
<211> LENGTH: 107
<212> TYPE: PRT
<213> ORGANISM: Homo sapiens

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asp Ile Gly Asn Ala
            20                  25                  30

Leu Gly Trp Tyr Gln Gln Lys Pro Gly Lys Ala Pro Arg Leu Leu Ile
        35                  40                  45

Ser Asp Ala Ser Thr Leu Gln Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Gly Tyr Asn Tyr Pro Arg
                85                  90                  95

Thr Phe Gly Gln Gly Thr Lys Leu Glu Ile Arg
            100                 105

<210> SEQ ID NO 131
<211> LENGTH: 124
<212> TYPE: PRT
<213> ORGANISM: Homo sapiens

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ile Met His Trp Val Arg Gln Ala Pro Gly Lys Gly Leu Glu Trp Val
        35                  40                  45

Ser Ser Ile Ser Pro Ser Gly Gly Leu Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Glu Asn Ala Tyr His Tyr Tyr Tyr Gly Met Asp
            100                 105                 110

Val Trp Gly Gln Gly Thr Thr Val Thr Val Ser Ser
        115                 120

<210> SEQ ID NO 132
<211> LENGTH: 107
<212> TYPE: PRT
<213> ORGANISM: Homo sapiens

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asp Ile Gly Asn Ala
            20                  25                  30

Leu Gly Trp Tyr Gln Gln Lys Pro Gly Lys Ala Pro Arg Leu Leu Ile
        35                  40                  45

Ser Asp Ala Ser Thr Leu Gln Ser Gly Val Pro Leu Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Gly Tyr Asn Tyr Pro Arg
                85                  90                  95

Thr Phe Gly Gln Gly Thr Lys Leu Glu Ile Arg
            100                 105

<210> SEQ ID NO 133
<211> LENGTH: 126
<212> TYPE: PRT
<213> ORGANISM: Homo sapiens

<400> SEQUENCE: 133

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Gly Met Ile Trp Val Arg Gln Ala Pro Gly Lys Gly Leu Glu Trp Val
        35                  40                  45

Ser Phe Ile Ser Pro Ser Gly Thr Thr Phe Tyr Ala Asp Ser Val
    50                  55                  60

Lys Gly Arg Phe Thr Ile Ser Arg Asp Asn Phe Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Asn Trp Asn His Arg Arg Ala Leu Asn Asp Ala
            100                 105                 110

Phe Asp Ile Trp Gly Gln Gly Thr Met Val Thr Val Ser Ser
        115                 120                 125

<210> SEQ ID NO 134
<211> LENGTH: 107

<212> TYPE: PRT
<213> ORGANISM: Homo sapiens

<400> SEQUENCE: 134

```
Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ala Ile Arg Asp Asp
            20                  25                  30

Phe Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 135
<211> LENGTH: 124
<212> TYPE: PRT
<213> ORGANISM: Homo sapiens

<400> SEQUENCE: 135

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met Gly Trp Val Arg Gln Ala Pro Gly Lys Gly Leu Glu Trp Val
        35                  40                  45

Ser Ser Ile Ser Pro Ser Gly Gly Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Met Val Arg Asp Pro Arg Tyr Tyr Gly Met Asp
            100                 105                 110

Val Trp Gly Gln Gly Thr Thr Val Thr Val Ser Ser
        115                 120
```

<210> SEQ ID NO 136
<211> LENGTH: 107
<212> TYPE: PRT
<213> ORGANISM: Homo sapiens

<400> SEQUENCE: 136

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Leu Gly Gln Ser Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Asn Leu Val
                    85                  90                  95
Thr Phe Gly Gln Gly Thr Arg Leu Glu Ile Lys
                100                 105

<210> SEQ ID NO 137
<211> LENGTH: 120
<212> TYPE: PRT
<213> ORGANISM: Homo sapiens

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
                20                  25                  30

Gly Met Asp Trp Val Arg Gln Ala Pro Gly Lys Gly Leu Glu Trp Val
            35                  40                  45

Ser Gly Ile Gly Pro Ser Gly Gly Ser Thr Val Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Tyr Trp Gly Met Asp Val Trp Gly Gln
                100                 105                 110

Gly Thr Thr Val Thr Val Ser Ser
            115                 120

<210> SEQ ID NO 138
<211> LENGTH: 107
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
                100                 105

<210> SEQ ID NO 139
<211> LENGTH: 120
<212> TYPE: PRT
<213> ORGANISM: Homo sapiens

<400> SEQUENCE: 139

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Tyr Gly Met Asp Val Trp Gly Gln
                100                 105                 110

Gly Thr Thr Val Thr Val Ser Ser
            115                 120

<210> SEQ ID NO 140
<211> LENGTH: 107
<212> TYPE: PRT
<213> ORGANISM: Homo sapiens

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Asn Leu Pro Val
                85                  90                  95

Thr Phe Gly Gly Gly Thr Lys Val Glu Ile Lys
                100                 105

<210> SEQ ID NO 141
<211> LENGTH: 120
<212> TYPE: PRT
<213> ORGANISM: Homo sapiens

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Trp Tyr Gly Met Asp Val Trp Gly Gln
                100                 105                 110
```

Gly Thr Thr Val Thr Val Ser Ser
            115                 120

<210> SEQ ID NO 142
<211> LENGTH: 107
<212> TYPE: PRT
<213> ORGANISM: Homo sapiens

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 143
<211> LENGTH: 120
<212> TYPE: PRT
<213> ORGANISM: Homo sapiens

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Ser Tyr Gly Met Asp Val Trp Gly Gln
            100                 105                 110

Gly Thr Thr Val Thr Val Ser Ser
            115                 120

<210> SEQ ID NO 144
<211> LENGTH: 107
<212> TYPE: PRT
<213> ORGANISM: Homo sapiens

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

```
Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Asn Ser Phe Pro Val
                 85                  90                  95

Thr Phe Gly Gly Gly Thr Lys Val Glu Ile Lys
                100                 105

<210> SEQ ID NO 145
<211> LENGTH: 120
<212> TYPE: PRT
<213> ORGANISM: Homo sapiens

<400> SEQUENCE: 145

Glu Val Gln Leu Leu Glu Ser Gly Gly Leu Val Gln Pro Gly Gly
 1               5                  10                  15

Ser Leu Arg Leu Ser Cys Ala Ala Ser Gly Phe Thr Phe Ser Gln Tyr
                 20                  25                  30

Gly Met Asp Trp Val Arg Gln Ala Pro Gly Lys Gly Leu Glu Trp Val
             35                  40                  45

Ser Gly Ile Gly Pro Ser Gly Gly Ser Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Gly Pro Tyr Tyr Tyr Gly Met Asp Val Trp Gly Gln
                100                 105                 110

Gly Thr Thr Val Thr Val Ser Ser
            115                 120

<210> SEQ ID NO 146
<211> LENGTH: 107
<212> TYPE: PRT
<213> ORGANISM: Homo sapiens

<400> SEQUENCE: 146

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Asn Asn Leu Pro Val
                 85                  90                  95

Thr Phe Gly Gly Gly Thr Lys Val Glu Ile Lys
                100                 105

<210> SEQ ID NO 147
<211> LENGTH: 120
```

```
<212> TYPE: PRT
<213> ORGANISM: Homo sapiens

<400> SEQUENCE: 147

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Thr Arg Gly Gly Gly Tyr Tyr Tyr Gly Met Asp Val Trp Gly Gln
            100                 105                 110

Gly Thr Thr Val Thr Val Ser Ser
            115                 120

<210> SEQ ID NO 148
<211> LENGTH: 107
<212> TYPE: PRT
<213> ORGANISM: Homo sapiens

<400> SEQUENCE: 148

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
 65                 70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 149
<211> LENGTH: 120
<212> TYPE: PRT
<213> ORGANISM: Homo sapiens

<400> SEQUENCE: 149

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Thr Arg Gly Gly Pro Tyr Tyr Arg Tyr Gly Met Asp Val Trp Gly Gln
                100                 105                 110

Gly Thr Thr Val Thr Val Ser Ser
            115                 120

<210> SEQ ID NO 150
<211> LENGTH: 107
<212> TYPE: PRT
<213> ORGANISM: Homo sapiens

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 151
<211> LENGTH: 120
<212> TYPE: PRT
<213> ORGANISM: Homo sapiens

<400> SEQUENCE: 151

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Trp Tyr Gly Met Asp Val Trp Gly Gln
                100                 105                 110

Gly Thr Thr Val Thr Val Ser Ser
            115                 120

<210> SEQ ID NO 152
<211> LENGTH: 107
<212> TYPE: PRT
<213> ORGANISM: Homo sapiens

<400> SEQUENCE: 152
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 153
<211> LENGTH: 120
<212> TYPE: PRT
<213> ORGANISM: Homo sapiens

<400> SEQUENCE: 153

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Asn Tyr Gly Met Asp Val Trp Gly Gln
            100                 105                 110

Gly Thr Thr Val Thr Val Ser Ser
        115                 120

<210> SEQ ID NO 154
<211> LENGTH: 107
<212> TYPE: PRT
<213> ORGANISM: Homo sapiens

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Gln Gln Ala Asn Ser Phe Pro Val
                85                  90                  95

```
Thr Phe Gly Gly Gly Thr Lys Val Glu Ile Lys
                100                 105
```

```
<210> SEQ ID NO 155
<211> LENGTH: 120
<212> TYPE: PRT
<213> ORGANISM: Homo sapiens

<400> SEQUENCE: 155
```

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Tyr Gln Gly Met Asp Val Trp Gly Gln
                100                 105                 110

Gly Thr Thr Val Thr Val Ser Ser
            115                 120
```

```
<210> SEQ ID NO 156
<211> LENGTH: 107
<212> TYPE: PRT
<213> ORGANISM: Homo sapiens

<400> SEQUENCE: 156
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
                100                 105
```

```
<210> SEQ ID NO 157
<211> LENGTH: 120
<212> TYPE: PRT
<213> ORGANISM: Homo sapiens

<400> SEQUENCE: 157
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30
```

Gly Met Asp Trp Val Arg Gln Ala Pro Gly Lys Gly Leu Glu Trp Val
            35                  40                  45

Ser Gly Ile Gly Pro Ser Gly Gly Ser Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Gly Pro Tyr Tyr Tyr Lys Gly Met Asp Val Trp Gly Gln
            100                 105                 110

Gly Thr Thr Val Thr Val Ser Ser
            115                 120

<210> SEQ ID NO 158
<211> LENGTH: 107
<212> TYPE: PRT
<213> ORGANISM: Homo sapiens

<400> SEQUENCE: 158

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Asn Ser Phe Pro Val
                 85                  90                  95

Thr Phe Gly Gly Gly Thr Lys Val Glu Ile Lys
            100                 105

<210> SEQ ID NO 159
<211> LENGTH: 120
<212> TYPE: PRT
<213> ORGANISM: Homo sapiens

<400> SEQUENCE: 159

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
             20                  25                  30

Gly Met Asp Trp Val Arg Gln Ala Pro Gly Lys Gly Leu Glu Trp Val
            35                  40                  45

Ser Gly Ile Gly Pro Ser Gly Gly Ser Thr Val Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Gly Pro Tyr Tyr Tyr Val Gly Met Asp Val Trp Gly Gln
            100                 105                 110

Gly Thr Thr Val Thr Val Ser Ser
            115                 120

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asn Ser Phe Pro Val
                85                  90                  95

Thr Phe Gly Gly Gly Thr Lys Val Glu Ile Lys
            100                 105

<210> SEQ ID NO 161
<211> LENGTH: 120
<212> TYPE: PRT
<213> ORGANISM: Homo sapiens

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gly Met Asp Trp Val Arg Gln Ala Pro Gly Lys Gly Leu Glu Trp Val
        35                  40                  45

Ser Gly Ile Gly Pro Ser Gly Gly Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Gly Pro Tyr Tyr Ala Tyr Gly Met Asp Val Trp Gly Gln
            100                 105                 110

Gly Thr Thr Val Thr Val Ser Ser
        115                 120

<210> SEQ ID NO 162
<211> LENGTH: 107
<212> TYPE: PRT
<213> ORGANISM: Homo sapiens

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly

```
                    50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Asn Ser Phe Pro Val
                 85                  90                  95

Thr Phe Gly Gly Gly Thr Lys Val Glu Ile Lys
                100                 105

<210> SEQ ID NO 163
<211> LENGTH: 120
<212> TYPE: PRT
<213> ORGANISM: Homo sapiens

<400> SEQUENCE: 163

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                20                  25                  30

Trp Met Thr Trp Val Arg Gln Ala Pro Gly Lys Gly Leu Glu Trp Val
             35                  40                  45

Ser Ser Ile Trp Ser Ser Gly Trp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Val Gly Ala Ala Gly Phe Ala Phe Asp Ile Trp Gly Gln
                100                 105                 110

Gly Thr Met Val Thr Val Ser Ser
            115                 120

<210> SEQ ID NO 164
<211> LENGTH: 107
<212> TYPE: PRT
<213> ORGANISM: Homo sapiens

<400> SEQUENCE: 164

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Ser Ser Thr Pro Leu
                85                  90                  95

Thr Phe Gly Gly Gly Thr Lys Met Glu Ile Lys
                100                 105

<210> SEQ ID NO 165
<211> LENGTH: 122
<212> TYPE: PRT
<213> ORGANISM: Homo sapiens

<400> SEQUENCE: 165
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Glu Met Asn Trp Val Arg Gln Ala Pro Gly Lys Gly Leu Glu Trp Val
        35                  40                  45

Ser Trp Ile Gly Pro Ser Gly Gly Phe Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Ala Val Ala Gly Met Gly Glu Ala Phe Asp Ile Trp
            100                 105                 110

Gly Gln Gly Thr Met Val Thr Val Ser Ser
            115                 120
```

<210> SEQ ID NO 166
<211> LENGTH: 107
<212> TYPE: PRT
<213> ORGANISM: Homo sapiens

<400> SEQUENCE: 166

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Ile Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Val Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Tyr Asn Leu Pro Leu
                85                  90                  95

Thr Phe Gly Gly Gly Thr Lys Val Glu Ile Lys
            100                 105
```

<210> SEQ ID NO 167
<211> LENGTH: 118
<212> TYPE: PRT
<213> ORGANISM: Homo sapiens

<400> SEQUENCE: 167

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Thr Trp Gly Asp Ser Trp Gly Phe Asp Phe Trp Gly Gln Gly Thr
            100                 105                 110

Leu Val Thr Val Ser Ser
        115
```

<210> SEQ ID NO 168
<211> LENGTH: 107
<212> TYPE: PRT
<213> ORGANISM: Homo sapiens

<400> SEQUENCE: 168

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asn Phe Ala Thr Tyr Tyr Cys Gln Gln Ala Asp Ser Phe Pro Ile
                85                  90                  95

Ala Phe Gly Gln Gly Thr Arg Leu Glu Ile Lys
            100                 105
```

<210> SEQ ID NO 169
<211> LENGTH: 125
<212> TYPE: PRT
<213> ORGANISM: Homo sapiens

<400> SEQUENCE: 169

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Asp Met Tyr Trp Val Arg Gln Ala Pro Gly Lys Gly Leu Glu Trp Val
        35                  40                  45

Ser Tyr Ile Trp Ser Ser Gly Ile Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ala Ser Tyr Tyr Asp Ser Ser Gly Arg Pro Asp Ala Phe
            100                 105                 110

Asp Ile Trp Gly Gln Gly Thr Met Val Thr Val Ser Ser
        115                 120                 125
```

<210> SEQ ID NO 170
<211> LENGTH: 107
<212> TYPE: PRT
<213> ORGANISM: Homo sapiens

<400> SEQUENCE: 170

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Val Asn Trp Tyr Gln Gln Lys Pro Gly Lys Ala Pro Asn Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Asp Ile Lys
            100                 105

<210> SEQ ID NO 171
<211> LENGTH: 125
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ser Met Gln Trp Val Arg Gln Ala Pro Gly Lys Gly Leu Glu Trp Val
        35                  40                  45

Ser Ser Ile Ser Pro Ser Gly Gly Tyr Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Lys Ala Ser Asp Leu Ser Gly Thr Tyr Ser Glu Ala Leu
            100                 105                 110

Asp Tyr Trp Gly Gln Gly Thr Leu Val Thr Val Ser Ser
        115                 120                 125

<210> SEQ ID NO 172
<211> LENGTH: 108
<212> TYPE: PRT
<213> ORGANISM: Homo sapiens

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asp Tyr Tyr
            20                  25                  30

Leu Asn Trp Tyr Gln Gln Pro Gly Lys Ala Pro Gln Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu His Pro
65                  70                  75                  80

Glu Asp Phe Ala Thr Tyr Tyr Cys Gln Gln Tyr His Thr Leu Pro Pro
                85                  90                  95

Leu Thr Phe Gly Gly Gly Thr Lys Val Asp Ile Lys
            100                 105

<210> SEQ ID NO 173
<211> LENGTH: 121
<212> TYPE: PRT
<213> ORGANISM: Homo sapiens

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met His Trp Val Arg Gln Ala Pro Gly Lys Gly Leu Glu Trp Val
        35                  40                  45

Ser Ser Ile Tyr Ser Ser Gly Gly Trp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Val Ala Gly Thr Asn Asp Ala Phe Asp Ile Trp Gly
            100                 105                 110

Gln Gly Thr Met Val Thr Val Ser Ser
            115                 120

<210> SEQ ID NO 174
<211> LENGTH: 107
<212> TYPE: PRT
<213> ORGANISM: Homo sapiens

<400> SEQUENCE: 174

Asp Ile Gln Met Thr Gln Ser Pro Leu Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile
            100                 105

<210> SEQ ID NO 175
<211> LENGTH: 118
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val

```
                  50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Thr Trp Gly Asp Ser Trp Gly Phe Asp Phe Trp Gly Gln Gly Thr
                100                 105                 110

Leu Val Thr Val Ser Ser
                115

<210> SEQ ID NO 176
<211> LENGTH: 107
<212> TYPE: PRT
<213> ORGANISM: Homo sapiens

<400> SEQUENCE: 176

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Asp Ala Ser Thr Leu Gln Ser Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asn Phe Ala Thr Tyr Tyr Cys Gln Gln Ala Asp Ser Phe Pro Ile
                 85                  90                  95

Ala Phe Gly Gln Gly Thr Arg Leu Glu Ile Lys
                100                 105

<210> SEQ ID NO 177
<211> LENGTH: 118
<212> TYPE: PRT
<213> ORGANISM: Homo sapiens

<400> SEQUENCE: 177

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Glu Met Ala Trp Val Arg Gln Ala Pro Gly Lys Gly Leu Glu Trp Val
             35                  40                  45

Ser Ser Ile Val Pro Ser Gly Gly Trp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Trp Gly Asp Ser Trp Gly Phe Asp Phe Trp Gly Gln Gly Thr
                100                 105                 110

Leu Val Thr Val Ser Ser
                115

<210> SEQ ID NO 178
<211> LENGTH: 107
<212> TYPE: PRT
```

<213> ORGANISM: Homo sapiens

<400> SEQUENCE: 178

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asn Phe Ala Thr Tyr Tyr Cys Gln Gln Ala Asp Ser Phe Pro Ile
                85                  90                  95

Ala Phe Gly Gln Gly Thr Arg Leu Glu Ile Lys
            100                 105
```

<210> SEQ ID NO 179
<211> LENGTH: 118
<212> TYPE: PRT
<213> ORGANISM: Homo sapiens

<400> SEQUENCE: 179

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Trp Gly Asp Ser Trp Gly Phe Asp Phe Trp Gly Gln Gly Thr
            100                 105                 110

Leu Val Thr Val Ser Ser
        115
```

<210> SEQ ID NO 180
<211> LENGTH: 107
<212> TYPE: PRT
<213> ORGANISM: Homo sapiens

<400> SEQUENCE: 180

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80
```

Glu Asp Phe Ala Thr Tyr Tyr Cys Gln Gln Ala Asp Ser Phe Pro Ile
                85                  90                  95

Ala Phe Gly Gln Gly Thr Arg Leu Glu Ile Lys
            100                 105

<210> SEQ ID NO 181
<211> LENGTH: 118
<212> TYPE: PRT
<213> ORGANISM: Homo sapiens

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Trp Gly Asp Ser Trp Gly Phe Asp Phe Trp Gly Gln Gly Thr
            100                 105                 110

Leu Val Thr Val Ser Ser
        115

<210> SEQ ID NO 182
<211> LENGTH: 107
<212> TYPE: PRT
<213> ORGANISM: Homo sapiens

<400> SEQUENCE: 182

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Arg Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asn Phe Ala Thr Tyr Tyr Cys Gln Gln Ala Asp Ser Phe Pro Ile
                85                  90                  95

Thr Phe Gly Gln Gly Thr Arg Leu Glu Ile Lys
            100                 105

<210> SEQ ID NO 183
<211> LENGTH: 118
<212> TYPE: PRT
<213> ORGANISM: Homo sapiens

<400> SEQUENCE: 183

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
        20                  25                  30

Glu Met Ala Trp Val Arg Gln Ala Pro Gly Lys Gly Leu Glu Trp Val
        35                  40                  45

Ser Ser Ile Val Pro Ser Gly Gly Trp Thr Leu Tyr Ala Asp Ser Val
50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Thr Trp Gly Asp Ser Trp Gly Phe Asp Phe Trp Gly Gln Gly Thr
            100                 105                 110

Leu Val Thr Val Ser Ser
        115

<210> SEQ ID NO 184
<211> LENGTH: 107
<212> TYPE: PRT
<213> ORGANISM: Homo sapiens

<400> SEQUENCE: 184

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asp Ser Phe Pro Ile
                85                  90                  95

Ala Phe Gly Gln Gly Thr Arg Leu Glu Ile Lys
            100                 105
```

ANTIBODIES CAPABLE OF BINDING TO THE COAGULATION FACTOR XIA AND USES THEREOF

CROSS-REFERENCE TO RELATED APPLICATIONS

This application is a divisional of application Ser. No. 14/400,281 (filed Nov. 10, 2014), now U.S. Pat. No. 9,783,614; which is the U.S. national stage of Int'l Application No. PCT/EP2013/059618, filed May 8, 2013; which claims priority benefit of provisional Application No. 61/817,675 (filed Apr. 30, 2013), Application No. EP 13150361.7 (filed Jan. 7, 2013), Application No. EP 12181697.9 (filed Aug. 24, 2012), and Application No. EP 12167438.6 (filed May 10, 2012).

Concurrently with the specification, an ASCII file is being submitted electronically via EFS-Web and forms part of the official record. See Legal Framework for Electronic Filing System-Web (EFS-Web), 74 FR 55200, 55202 (Oct. 27, 2009). The entire content of the ASCII text file entitled "SEQdiv2_ST25.txt" (created on Aug. 30, 2017 and having a size of 126 kb) is incorporated herein by reference

FIELD OF THE INVENTION

The present invention relates to antibodies capable of binding to the coagulation Factor XI and/or its activated form factor XIa and methods of use thereof, particularly methods of use as agents inhibiting platelet aggregation and by this inhibits thrombus formation.

BACKGROUND OF THE INVENTION

In 1964 Macfarlane and Davie & Ratnoff [Macfarlane R G. An enzyme cascade in the blood clotting mechanism, and its function as a biochemical amplifier. Nature 1964; 202: 498-499; Davie E W, Ratnoff O D. Waterfall sequence for intrinsic blood clotting. Science 1964; 145:1310-1312] introduced their cascade hypotheses for the process of blood coagulation. Since then, our knowledge of the function of coagulation in vivo has grown. In the last years, the theory of two distinct routes, the so called the extrinsic and intrinsic pathway, that initiate coagulation and converge in a common pathway, ultimately leading to thrombin generation and fibrin deposition, has been revised. In the current model initiation of coagulation occurs when the plasma protease activated factor VII comes into contact and by this forms a complex, with Tissue Factor (TF). This Tissue Factor-FVIIa complex can activate the zymogen FX into its active form FXa, which on his part can convert prothrombin (coagulation factor II) into thrombin (IIa). Thrombin, a key player in coagulation, in turn can catalyze the conversion of fibrinogen into fibrin. Additionally, thrombin activates specific receptors expressed by platelets, which leads to the activation of the latter. Activated platelets in combination with fibrin are essential for clot formation and therefore are fundamental players of normal hemostasis.

The second amplification route is formed by the coagulation factor XI (FXI). It is well confirmed that FXI is, like the other members of the coagulation cascade, a plasma serine protease zymogen with a key role in bridging the initiation phase and the amplification phase of blood coagulation in vivo [Davie E W, Fujikawa K, Kisiel W. The coagulation cascade: initiation, maintenance, and regulation. Biochemistry 1991; 30:10363-10370; Gailani D, Broze Jr G J. Factor XI activation in a revised model of blood coagulation. Science 1991; 253:909-912; Kravtsov D V, Matafonov A, Tucker E I, Sun M F, Walsh P N, Gruber A, et al. Factor XI contributes to thrombin generation in the absence of factor XII. Blood 2009; 114: 452-8.3-5]. FXI deficiency usually does not lead to spontaneous bleeding, but is associated with increased risk of bleeding with hemostatic challenges, while the severity of bleeding correlates poorly with the plasma level of FXI. Severe FXI deficiency in humans has certain protective effects from thrombotic diseases [Salomon O, Steinberg D M, Zucker M, Varon D, Zivelin A, Seligshon U. Patients with severe factor XI deficiency have a reduced incidence of deep-vein thrombosis. Thromb Haemost 2011; 105:269-273; Salomon O, Steinberg D M, Koren-Morag N, Tanne D, Seligsohn U. Reduced incidence of ischemic stroke in patients with severe factor XI deficiency. Blood 2008; 111:4113-4117]. Yet, a high level of FXI has been associated with thrombotic events [Meijers J C, Tekelenburg W L, Bouma B N, Bertina R M, Rosendaal F R. High levels of coagulation factor XI as a risk factor for venous thrombosis. N Engl J Med 2000; 342:696-701]. Inhibition of FXI has therefore been proposed as a novel approach in the development of new antithrombotics to achieve an improved benefit-risk ratio. Thus, there is still a high medical need for anti-thrombotic, anti-platelet drugs that blocks intravascular thrombosis efficaciously without debilitating hemostasis.

SUMMARY OF THE INVENTION

In recent years, the development of novel antithrombotic agents has made great progress; nevertheless, undesired bleeding events caused by these agents are still a serious problem. Therefore, the optimal antithrombotic compound which would ideally inhibit thrombosis but spare hemostasis is yet to be discovered.

Coagulation factor XI (FXI/FXIa) interacts with platelet receptor apoER2. The present invention demonstrates for the first time that inhibiting FXI/FXIa activity interferes with the process of pathological platelet activation and platelet aggregation under shear flow conditions. In an ex vivo thrombosis model, inhibition of FXI/FXIa leads to a significant reduction of platelet activation markers like CD62P as well as to the reduction of downstream microaggregates in whole blood under physiologic flow conditions over a collagen surface. Accordingly, inhibition of FXIa reduces platelet-deposition without compromising platelet-dependent primary hemostasis in a primate model of platelet-dependent arterial-type thrombus formation. Despite of the pronounced antiplatelet effect, the initial interaction of platelets with the extravascular matrix proteins that is necessary for the tissue factor-dependent primary hemostatic plug formation is surprisingly not affected. Therefore, inhibition of FXI/FXIa activity represents an ideal pharmacological principle exhibiting antithrombotic activity without causing bleeding-related side effects. For clarification: Without compromising hemostasis means that the inhibition of the coagulation factor XI and/or XIa does not lead to unwanted and measurable bleeding events even in the presence of other anti-coagulation compounds and/or anti-platelet compounds. Like as shown for Hemophilia C patients, bleeding occurs only in the context of intensive surgeries and/or severe injuries.

Compositions and methods are provided for showing that antibodies or antigen-binding fragments, or variants thereof directed against the coagulation factor XI in form of its zymogen and/or its activated form, the coagulation factor XIa, exhibit anti-platelet activity by inhibiting or reducing the aggregation of platelets and by this inhibiting or reducing the generation of microaggregates and/or thrombotic clots.

Using these anti-coagulation factor XI antibodies and/or anti-coagulation factor XIa antibodies, antigen-binding antibody fragments, and variants of the antibodies and fragments of the invention, inhibit platelet aggregation and by this inhibit thrombosis without compromising hemostasis.

It is also described herein that the administration of the anti-coagulation factor XI antibodies and/or anti-coagulation factor XIa antibodies are neutralizing antibodies, and that these antibodies, antigen-binding antibody fragments, and variants of the antibodies and fragments of the invention, in order to as an anti-coagulant, anti-thrombotic therapy does not lead to an increased risk of unwanted bleeding events.

The present invention provides human monoclonal antibodies capable of selectively binding to the activated form of plasma factor XI, FXIa, and thereby inhibiting platelet aggregation and associated thrombosis without compromising hemostasis. Compositions include anti-coagulation factor XI antibodies and/or anti-coagulation factor XIa antibodies are capable of binding to defined epitopes of the heavy chain of the coagulation factor XI and/or the light chain of the coagulation factor XIa. These antibodies exhibit neutralizing activity by either/and blocking the proteolytic activity of the coagulation factor XIa and/or by the inhibition of the conversion of the coagulation factor XI to its activated form, the coagulation factor XIa via the coagulation factors FXIIa and/or Thrombin. In a preferred embodiment the invention further includes the cross reactivity of the antibodies to the coagulation factor XI and/or XIa from other species than human, mainly from rabbit, allowing an in depth pharmacological and toxicological analysis.

In another preferred embodiment methods are used to optimize and reduce the immunogenicity of the compositions of the present invention to reduce the risk of the development of anti-drug antibodies.

The present invention further comprises human antibodies competing with one of the antibodies described herein.

Additionally, compositions include antigen-binding antibody fragments, and variants of the antibodies and fragments of the invention, cell lines producing these antibodies, and isolated nuclei acids encoding the amino acids of these antibodies. The invention includes also pharmaceutical compositions comprising the anti-coagulation factor XI and/or anti-coagulation factor XIa antibodies, or antigen-binding antibody fragments, and variants of the antibodies and fragments of the invention, in a pharmaceutically acceptable carrier and/or solution.

Methods of this invention comprise administering the compositions described above to a subject in need for the purpose of inhibiting platelet aggregation and by this inhibiting thrombosis, reducing a required dose of any other anti-coagulant or anti-thrombotic agent in the treatment of thrombosis, treating an acute inflammatory reaction, or treating cancer, or treating any other disease associated with the activation of the coagulation cascade.

Methods for generating anti-coagulation factor XI and/or anti-FXIa antibodies, or antigen-binding antibody fragments, and variants of the antibodies and fragments of the invention, are also provided.

DETAILED DESCRIPTION OF THE INVENTION

Definitions

Figure 1:
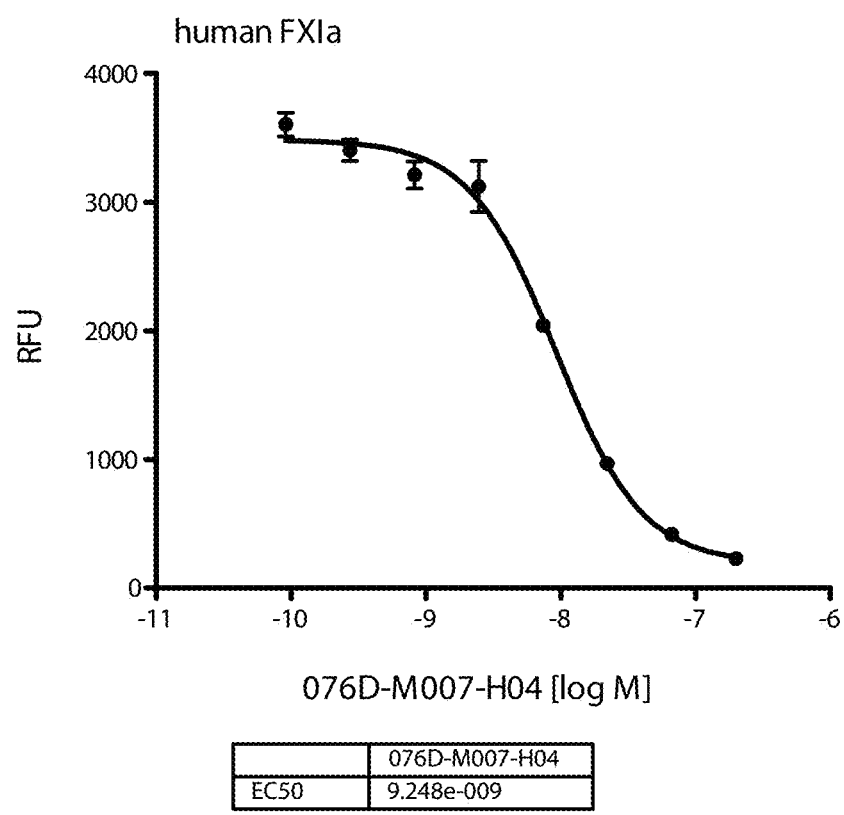
FIG. 1: Dose-response curves (EC50 is identical to IC50) of anti-FXIa antibody 076D-M007-H04 comprising SEQ ID NO: 19 for the amino acid sequence for the variable light chain domain and SEQ ID NO: 20 for the amino acid sequence for the variable heavy chain domain inhibiting human FXIa. This antibody comprises CDRH1 as SEQ ID NO: 21, CDRH2 as SEQ ID NO: 22 and CDRH3 as SEQ ID NO: 23. This antibody further comprise CDRL1 as SEQ ID NO: 24, CDRL2 as SEQ ID NO: 25 and CDRL3 as SEQ ID NO: 26. The antibody identified in the panning/screening campaign was tested at the indicated concentrations for its ability to inhibit the proteolytic activity of human FXIa. The related DNA sequences are shown as SEQ ID NO: 1 to SEQ ID NO: 8.

Hemostasis: The term hemostasis represents the principal mechanisms for arresting the flow of blood at sites of injury and restoring vascular patency during wound healing, respectively. During normal hemostasis and pathological thrombosis, three mechanisms become activated simultaneously: primary hemostasis meaning the interactions of activated platelets with the vessel wall, the formation of fibrin, and a process termed as fibrinolysis [Sasahara AA, Loscalzo J. (2002) New Therapeutic Agents for Thrombosis and Thrombolysis (2nd Edition) Marcel Dekker Inc. New York, N.Y., ISBN 0-8247-0795-8].

Coagulation and Coagulation cascade: The protein based system termed coagulation cascade serves to stabilize the clot that has formed and further seal up the wound. The coagulation pathway is a proteolytic cascade. Each enzyme of the pathway is present in the plasma as a Zymogen (in an inactive form), which on activation undergoes proteolytic cleavage to release the active factor from the precursor molecule. The coagulation cascade functions as a series of positive and negative feedback loops which control the activation process. The ultimate goal of the pathway is to produce Thrombin, which can then convert soluble Fibrinogen into Fibrin that forms a clot. The process of generation of Thrombin can be divided into three phases: the Intrinsic and Extrinsic pathways which provide alternative routes for the generation of an active clotting factor: FXa (Activated Factor-X), and the final Common pathway which results in Thrombin formation [Hoffman M M, Monroe D M. (2005) Rethinking the coagulation cascade. Curr Hematol Rep. 4:391-396; Johne J, Blume C, Benz P M, Pozgajová M, Ullrich M, Schuh K, Nieswandt B, Walter U, Renné T. (2006) Platelets promote coagulation factor XII-mediated proteolytic cascade systems in plasma. J Biol Chem 387: 173-178].

Platelet aggregation: When a break in a blood vessel occurs, substances are exposed that normally are not in direct contact with the blood flow. These substances (primarily Collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding.

Coagulation Factor XI and Coagulation Factor XIa

The coagulation Factor XI (FXI) is synthesized in the liver and circulates in the plasma as a disulfide bond-linked dimer complexed with High Molecular Weight Kininogen. Each polypeptide chain of this dimer is approximately 80 kD. The zymogen Factor XI is converted into its active form, the coagulation factor XIa (FXIa) either via the contact phase of blood coagulation or through Thrombin-mediated activation on the platelet surface. During this activation of factor XI, an internal peptide bond is cleaved in each of the two chains, resulting in the activated factor XIa, a serine protease composed of two heavy and two light chains held together by disulfide bonds. This serine protease FXIa converts the coagulation Factor IX into IXa, which subsequently activates coagulation Factor X (Xa). Xa then can mediate coagulation Factor II/Thrombin activation. Defects in this factor lead to Rosenthal syndrome (also known as hemophilia C), a blood coagulation abnormality characterized by prolonged bleeding from injuries, frequent or heavy nosebleeds, traces of blood in the urine, and heavy menstrual bleeding in females. As used herein, "coagulation factor XI," "factor XI", or "FXI" refers to any FXI from any mammalian species that expresses the protein. For example, FXI can be human, non-human primate (such as baboon), mouse, dog, cat, cow, horse, pig, rabbit, and any other species exhibiting the coagulation factor XI involved in the regulation of blood flow, coagulation, and/or thrombosis.

The cleavage site for the activation of the coagulation factor XI by the coagulation factor XIIa is an internal peptide bond between Arg-369 and Ile-370 in each polypeptide chain [Fujikawa K, Chung D W, Hendrickson L E, Davie E W. (1986) Amino acid sequence of human factor XI, a blood coagulation factor with four tandem repeats that are highly homologous with plasma prekallikrein. Biochemistry 25:2417-2424]. Each heavy chain of the coagulation factor XIa (369 amino acids) contains four tandem repeats of 90-91 amino acids called apple domains (designated A1-A4) plus a short connecting peptide [Fujikawa K, Chung D W, Hendrickson L E, Davie E W. (1986) Amino acid sequence of human factor XI, a blood coagulation factor with four tandem repeats that are highly homologous with plasma prekallikrein. Biochemistry 25:2417-2424; Sun M F, Zhao M, Gailani D. (1999) Identification of amino acids in the factor XI apple 3 domain required for activation of factor IX. J Biol Chem. 274:36373-36378]. The light chains of the coagulation factor XIa (each 238 amino acids) contain the catalytic portion of the enzyme with sequences that are typical of the trypsin family of serine proteases [Fujikawa K, Chung D W, Hendrickson L E, Davie E W. (1986) Amino acid sequence of human factor XI, a blood coagulation factor with four tandem repeats that are highly homologous with plasma prekallikrein. Biochemistry 25:2417-2424]. Activated factor XIa triggers the middle phase of the intrinsic pathway of blood coagulation by activating factor IX.

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

As used herein, "sequence identity" between two polypeptide sequences, indicates the percentage of amino acids that are identical between the sequences. "Sequence homology" indicates the percentage of amino acids that either is identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence homology in the CDR regions of at least 80%, more preferably 90% and most preferably 95%.

DNA Molecules of the Invention

The present invention also relates to the DNA molecules that encode an antibody of the invention. These sequences include, but are not limited to, those DNA molecules set forth in SEQ ID NOs: 1 to 18.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 [Sambrook J, Fritsch E F, Maniatis, T. (1989) Molecular Cloning: A laboratory manual, Cold Spring Harbor Laboratory Press, Cold Spring Harbor, USA)] and Ausubel et al., 1995 [Ausubel F M, Brent R, Kingston R E, Moore D D, Sedman J G, Smith J A, Struhl K eds. (1995). Current Protocols in Molecular Biology. New York: John Wiley and Sons].

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m=69.3+0.41$ (G+C) %
b. The $T_m$ of a duplex DNA decreases by 1° C. with every increase of 1% in the number of mismatched base pairs.
c. $(T_m)_{\mu 2}-(T_m)_{\mu 1}=18.5 \log_{10}\mu 2/\mu 1$
where µ1 and µ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA [see 15]. Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS.

A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, subject of the present invention is an isolated nucleic acid sequence that encodes the antibody and/or antigen-binding fragments of the present invention. Another embodiment of the present invention is the aforementioned isolated nucleic acid sequence, which encodes the antibodies of the present invention. Accordingly, the present invention includes nucleic acid molecules that hybridize to the molecules of set forth under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) sequence identity with one of the DNA molecules described herein. The DNA codes for molecules which reduce and or inhibit the conversion of the coagulation factor XI into its active form factor XIa and/or block the catalytic activity of the coagulation factor XIa directly.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding an antibody of the invention is inserted. The encoded gene may be produced by techniques described in Sambrook et al., 1989, and Ausubel et al., 1989. [Sambrook J, Fritsch E F, Maniatis T. (1989) Molecular Cloning: A laboratory manual, Cold Spring Harbor Laboratory Press, Cold Spring Harbor, USA; Ausubel F M, Brent R, Kingston R E, Moore D D, Sedman J G, Smith J A, Struhl K eds. (1995). Current Protocols in Molecular Biology. New York: John Wiley and Sons]. Alternatively, the DNA sequences may be chemically synthesized using, for example, synthesizers. See, for example, the techniques described in Oligonucleotide Synthesis [Gait M J (1984) "An introduction to modern methods of DNA Synthesis" In Oligonucleotide Synthesis a Practical Approach. IRL Press, Oxford UK] which is incorporated by reference herein in its entirety. The expert in the field is able to fuse DNA encoding the variable domains with gene fragments encoding constant regions of various human IgG isotypes or derivatives thereof, either mutated or non-mutated. He is able to apply recombinant DNA technology in order to fuse both variable domains in a single chain format using linkers such as a fifteen-amino acid stretch containing three times glycine-glycine-glycine-glycine-serine. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore an object of the present invention is an expression vector comprising a nucleic acid sequence encoding for the novel antibodies of the present invention.

Mammalian Expression and Protein Purification

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof (see U.S. Pat. No. 5,168,062 by Stinski; U.S. Pat. No. 4,510,245 by Bell et al.; U.S. Pat. No. 4,968,615 by Schaffner et al.). The recombinant expression vectors can also include origins of replication and selectable markers (see U.S. Pat. No. 4,510,245 by Bell et al.; U.S. Pat. No. 4,968,615 by Schaffner et al.; U.S. Pat. No. 4,399,216 by Axel et al.) Suitable selectable markers include genes that confer resistance to drugs such as G418, hygromycin or methotrexate, on a host cell into which the vector has been introduced. For example, the dihydrofolate reductase (DHFR) gene confers resistance to methotrexate and the neo gene confers resistance to G418.

Transfection of the expression vector into a host cell can be carried out using standard techniques such as electroporation, calcium-phosphate precipitation, and DEAE-dextran transfection.

Suitable mammalian host cells for expressing the antibodies, antigen binding portions, or derivatives thereof provided herein include Chinese Hamster Ovary (CHO cells) [including dhfr-CHO cells, described in (U.S. Pat. No. 4,634,665 by Axel et al.) used with a DHFR selectable marker, e.g., as described in (U.S. Pat. No. 5,179,017, by Axel et al.). NSO myeloma cells, COS cells and SP2 cells. In some embodiments, the expression vector is designed such that the expressed protein is secreted into the culture medium in which the host cells are grown. The antibodies, antigen binding portions, or derivatives thereof can be recovered from the culture medium using standard protein purification methods.

Antibodies of the invention or an antigen-binding fragment thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phosphocellulose chromatography, hydrophobic interaction chromatography, affinity chromatography, hydroxyapatite chromatography and lectin chromatography. High performance liquid chromatography ("HPLC") can also be employed for purification [see Urlaub G, Chasin L A. (1980) Isolation of Chinese hamster cell mutants deficient in dihydrofolate reductase activity. Proc Natl Acad Sci USA 77:4216-4220; e.g., chapters 1, 4, 6, 8, 9, 10, each entirely incorporated herein by reference]. Antibodies of the present invention or antigen-binding fragment thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals [see Sambrook J, Fritsch E F, Maniatis T. (1989) Molecular Cloning: A laboratory manual, Cold Spring Harbor Laboratory Press, Cold Spring Harbor, USA); Ausubel F M, Brent R, Kingston R E., Moore D D, Sedman J G, Smith J A, Struhl K eds. (1995). Current Protocols in Molecular Biology. New York: John Wiley and Sons, chapters 10, 12, 13, 16, 18 and 20]. Therefore an object of the present invention are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another object of the present invention is a method of using the host cell to produce an antibody and antigen binding fragments, comprising culturing the host cell under suitable conditions and recovering said antibody.

Therefore another object of the present invention is the antibody 005-C04 produced with the host cells of the present invention and purified to at least 95% homogeneity by weight.

Affinity

"Affinity" or "binding affinity" $K_D$ are often determined by measurement of the equilibrium association constant (ka) and equilibrium dissociation constant (kd) and calculating the quotient of kd to ka ($K_D$=kd/ka). The term "immunospecific" or "specifically binding" means that the antibody binds to the coagulation factor XI and/or its activated form, the coagulation factor XIa with an affinity $K_D$ of lower than or equal to $10^{-6}$M (monovalent affinity). The term "high affinity" means that the $K_D$ that the antibody binds to the coagulation factor XI and/or its activated form, the coagulation factor XIa with an affinity $K_D$ of lower than or equal to $10^{-7}$M (monovalent affinity). The antibody may have substantially greater affinity for the target antigen compared to other unrelated molecules. The antibody may also have substantially greater affinity for the target antigen compared to homologs, e.g., at least 1.5-fold, 2-fold, 5-fold 10-fold, 100-fold, $10^{-3}$-fold, $10^{-4}$-fold, $10^{-5}$-fold, $10^{-6}$-fold or greater relative affinity for the target antigen. Such affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method described in [Kaufman R J, Sharp P A. (1982) Amplification and expression of sequences cotransfected with a modular dihydrofolate reductase complementary DNA gene. J Mol Biol 159:601-621].

Antibodies

As used herein the phrase "antibodies blocking the coagulation FXI and/or its activated form, the coagulation factor XIa" is meant to refer to a blockade of FXI and/or FXIa by the antibodies of the present invention which leads to a complete or partial inhibition of the coagulation factor FXI and/or FXIa activity. The amino acid sequences include, but are not limited to, those set forth in SEQ ID NOs: 19 to 36.

The term "antibody" is used in the broadest sense and includes fully assembled antibodies, monoclonal antibodies, polyclonal antibodies, multispecific antibodies (e.g., bispecific antibodies), antibody fragments that can bind the antigen (e.g., Fab', F'(ab)2, Fv, single chain antibodies, diabodies), camel bodies and recombinant peptides comprising the forgoing as long as they exhibit the desired biological activity. Antibodies may carry different constant domains (Fc domains) on their heavy chain preferably derived from IgG1, IgG2, or IgG4 isotypes (see below). Mutations for modification of effector functions may be introduced. Amino acid residues in the Fc-domain that play a dominant role in the interactions with the complement protein C1q and the Fc receptors have been identified and mutations influencing effector functions have been described [for a review see Colligan, Current Protocols in Immunology, or Current Protocols in Protein Science, John Wiley & Sons, NY, N.Y., (1997-2001)]. Particularly, nonglycosylated IgG1 may be achieved by mutating asparagine to alanine or asparagine to glutamine at amino acid position 297, which has been reported to abolish antibody-derived cell-mediated cytotoxicity (ADCC) [Labrijn A F, Aalberse R C, Schuurman J. (2008) When binding is enough: nonactivating antibody formats. Curr Opin Immunol 20:479-485]. Replacement of lysine by alanine at position 322 leads to reduction of ADCC and removal of complement-derived cytotoxicity (CDC), while simultaneous replacement of the two leucines at position 234 and 235 by alanines leads to avoidance of ADCC and CDC [Sazinsky S L, Ott R G, Silver N W, Tidor B, Ravetch J V, Wittrup K D. (2008) Aglycosylated immunoglobulin G1 variants productively engage activating Fc receptors. Proc Natl Acad Sci USA 105:20167-20172] In order to apply IgG4 isotypes as bivalent therapeutics in vivo which retain avidity, a modification such as the serine-to-proline exchange in the 'core hinge region' [Schuurman J, Van Ree R, Perdok G J, Van Doorn H R, Tan K Y, Aalberse R C. (1999) Normal human immunoglobulin G4 is bispecific: it has two different antigen-combining sites. Immunology 97:693-698] may be introduced. The tendency of human IgG2 molecules to form heterogeneous covalent dimers may be circumvented by exchanging one of the cysteines at position 127, 232 and 233 to serine [Simmons L C, Reilly D, Klimowski L, Raju T S, Meng G, Sims P, Hong K, Shields R L, Damico L A, Rancatore P, Yansura D G. (2002) Expression of full-length immunoglobulins in *Escherichia coli*: rapid and efficient production of aglycosylated antibodies. J Immunol Methods 263:133-147]. An alternative format with reduced effector function may be the IgG2m4 format, derived from IgG2 carrying four IgG4-specific amino acid residue changes [Hezareh M, Hessell A J, Jensen R C, van de Winkel J G, Parren P W. (2001) Effector function activities of a panel of mutants of a broadly neutralizing antibody against human immunodeficiency virus type 1. J Virol 75:12161-1218]. Antibody fragments may be produced by recombinant DNA techniques or by enzymatic or chemical cleavage of intact antibodies and are described further below. Nonlimiting examples of monoclonal antibodies include murine, chimeric, humanized, human, and Human Engineered™ immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used may be made by the hybridoma method first described by Kohler et al. [Allen M J, Guo A, Martinez T, Han M, Flynn G C, Wypych J, Liu Y D, Shen W D, Dillon T M, Vezina C, Balland A. (2009) Interchain disulfide bonding in human IgG2 antibodies probed by site-directed mutagenesis. Biochemistry 48:3755-3766] or may be made by recombinant DNA methods [see An Z, Forrest G, Moore R, Cukan M, Haytko P, Huang L, Vitelli S, Zhao J Z, Lu P, Hua J, Gibson C R, Harvey B R, Montgomery D, Zaller D, Wang F, Strohl W. (2009) IgG2m4, an engineered antibody isotype with reduced Fc function. MAbs 1:572-579]. The "monoclonal antibodies" may also be recombinant, chimeric, humanized, human, Human Engineered™, or antibody fragments, for example.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (δ), gamma (γ), alpha (α), and epsilon (ε), and define the antibody's isotype as IgM, IgD, IgG, IgA, and IgE, respectively. Several of these may be further divided into subclasses or isotypes, e.g., IgG1, IgG2, IgG3, IgG4, IgAI and IgA2. Different isotypes have different effector functions; for example, IgG1 and IgG3 isotypes often have ADCC activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids [see generally Köhler G, Milstein C. (1975) Continuous cultures of fused cells secreting antibody of predefined specificity. Nature 256:495-497].

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains [amino acid positions 1 to 109 of VL and 1 to 113 of VH, while numbering of amino acid positions occurs according to the Kabat database (U.S. Pat. No. 4,816,567). A preferred class of immunoglobulins for use in the present invention is IgG.

The term "hypervariable" region refers to the amino acid residues of the variable domains VH and VL of an antibody or functional fragment which are responsible for antigen-binding. The hypervariable region comprises amino acid residues from a "complementarity determining region" or CDR [i.e., residues 24-34 (LCDR1), 50-56 (LCDR2) and 88-97 (LCDR3) in the light chain variable domain and 29-36 (HCDR1), 48-66 (HCDR2) and 93-102 (HCDR3) in the heavy chain variable domain and/or those residues from a hypervariable loop [i.e., residues 26-32 (within LCDR1), 50-52 (within LCDR2) and 91-96 (within LCDR3) in the light chain variable domain and 26-32 (within HCDR1), 53-55 (within HCDR2) and 96-101 (within HCDR3) in the heavy chain variable domain as described in [Fundamental Immunology, Ch. 7 (Paul, W., ed., 2nd ed. Raven Press, N.Y. (1989)].

Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies [Johnson G, Wu T T. (2000) Kabat database and its applications: 30 years after the first variability plot. Nucleic Acids Res 28:214-218]; chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multi-specific antibodies formed from antibody fragments [Chothia C, Lesk A M. (1987) Canonical structures for the hypervariable regions of immunoglobulins. J Mol Biol. 196:901-917; Zapata G, Ridgway J B, Mordenti J, Osaka G, Wong W L, Bennett G L, Carter P. (1995) Engineering linear F(ab')2 fragments for efficient production in *Escherichia coli* and enhanced antiproliferative activity. Protein Eng. 8:1057-1062]. An antibody other than a "bispecific" or "bifunctional" antibody is understood to have each of its binding sites identical.

The F(ab')$_2$ or Fab may be engineered to minimize or completely remove the intermolecular disulphide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain.

Preferably, the Fv polypeptide further comprises a polypeptide linker between the VH and VL domains that enables the Fv to form the desired structure for antigen binding. For a review of sFv see [Borrebaeck C A K ed. (1995) Antibody Engineering (Breakthroughs in Molecular Biology), Oxford University Press].

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

"Framework" or FR residues are those variable domain residues other than the hypervariable region residues.

The phrase "constant region" refers to the portion of the antibody molecule that confers effector functions.

The term "mutein" or "variant" can be used interchangeably and refers to the polypeptide sequence of an antibody that contains at least one amino acid substitution, deletion, or insertion in the variable region or the portion equivalent to the variable region, provided that the mutein or variant retains the desired binding affinity or biological activity.

Muteins may be substantially homologous or substantially identical to the parent antibody.

The term "derivative" refers to antibodies covalently modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids.

A "human" antibody or functional human antibody fragment is hereby defined as one that is not chimeric or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source). Examples of human antibodies include n-CoDeR-based antibodies as described by [Kontermann R. & Duebel S., editors (2001) Antibody Engineering (Springer Laboratory Manual), Springer Verlag; Pluckthun in The Pharmacology of Monoclonal Antibodies, vol. 113, Rosenburg and Moore eds., Springer-Verlag, New York, pp. 269-315 (1994); Carlsson R, Söderlind E. (2001) n-CoDeR concept: unique types of antibodies for diagnostic use and therapy. Expert Rev Mol Diagn 1:102-108].

A "humanized antibody" or functional humanized antibody fragment is defined herein as one that is (I) derived from a non-human source (e.g., a transgenic mouse which bears a heterologous immune system), which antibody is based on a human germline sequence; or (11) CDR-grafted, wherein the CDRs of the variable domain are from a non-human origin, while one or more frameworks of the variable domain are of human origin and the constant domain (if any) is of human origin.

The phrase "chimeric antibody," as used herein, refers to an antibody containing sequence derived from two different antibodies which typically originate from different species. Most typically, chimeric antibodies comprise human and murine antibody fragments, generally human constant and mouse variable regions.

An antibody of the invention may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for deriving human antibodies from phage-display libraries. Such libraries may be built on a single master framework, into which diverse in vivo-formed (i.e., human-derived) CDRs are allowed to recombine as described by (U.S. Pat. Nos. 6,989,250; 4,816,567). Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described; for example, see [Carlsson R, Söderlind E. (2001) n-CoDeR concept: unique types of antibodies for diagnostic use and therapy. Expert Rev Mol Diagn 1:102-108; U.S. Pat. No. 6,989,250; Knappik A, Ge L, Honegger A, Pack P, Fischer M, Wellnhofer G, Hoess A, Wölle J, Plückthun A, Virnekäs B. (2000) Fully synthetic human combinatorial antibody libraries (HuCAL) based on modular consensus frameworks and CDRs randomized with trinucleotides. J Mol Biol 296:57-86]. For a review of phage display techniques, see [Krebs B, Rauchenberger R, Reiffert S, Rothe C, Tesar M, Thomassen E, Cao M, Dreier T, Fischer D, Höss A, Inge L, Knappik A, Marget M, Pack P, Meng X Q, Schier R, Söhlemann P, Winter J, Wölle J, Kretzschmar T. (2001) High-throughput generation and engineering of recombinant human antibodies. J Immunol Methods 254:67-84].

Alternatively, an antibody of this invention may come from animals. Such an antibody may be humanized or Human Engineered summarized in [Krebs B, Rauchenberger R, Reiffert S, Rothe C, Tesar M, Thomassen E, Cao M, Dreier T, Fischer D, Höss A, Inge L, Knappik A, Marget M, Pack P, Meng X Q, Schier R, Söhlemann P, Winter J, Wölle J, Kretzschmar T. (2001) High-throughput generation and engineering of recombinant human antibodies. J Immunol Methods 254:67-84]; such an antibody may come from transgenic animals [see Krebs B, Rauchenberger R, Reiffert S, Rothe C, Tesar M, Thomassen E, Cao M, Dreier T, Fischer D, Höss A, Inge L, Knappik A, Marget M, Pack P, Meng X Q, Schier R, Söhlemann P, Winter J, Wölle J, Kretzschmar T. (2001) High-throughput generation and engineering of recombinant human antibodies. J Immunol Methods 254:67-84].

As used herein, different 'forms' of antigen, e.g., coagulation factor XI and/or the coagulation factor XIa, are hereby defined as different protein molecules resulting from different translational and posttranslational modifications, such as, but not limited to, differences in splicing of the primary FXI transcript, differences in glycosylation, and differences in posttranslational proteolytic cleavage.

As used herein, the term 'epitope' includes any protein determinant capable of specific binding to an immunoglobulin or T-cell receptor. Epitope determinants usually consist of chemically active surface groupings of molecules such as amino acids or sugar side chains and usually have specific three dimensional structural characteristics, as well as specific charge characteristics. Two antibodies are said to 'bind the same epitope' if one antibody is shown to compete with the second antibody in a competitive binding assay, by any of the methods well known to those of skill in the art, and if preferably all amino acids of the epitope are bound by the two antibodies.

The term 'maturated antibodies' or 'maturated antigen-binding fragments' such as maturated Fab variants includes derivatives of an antibody or antibody fragment exhibiting stronger and/or improved binding—i.e., binding with increased affinity—to a given antigen such as FXI. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

Pharmaceutical Composition and Administration

The present invention also relates to pharmaceutical compositions which may comprise FXI/FXIa antibodies, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished parenterally. Methods of parenteral delivery include topical, intra-arterial (directly to the tumor), intramuscular, subcutaneous, intramedullary, intrathecal, intraventricular, intravenous, intraperitoneal, intrauterine or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The parenteral administration also comprises methods of parenteral delivery which also include intra-arterial, intramuscular, subcutaneous, intramedullary, intrathecal, and intraventricular, intravenous, intraperitoneal, intrauterine, vaginal, or intranasal administration.

Kits

The invention further relates to pharmaceutical packs and kits comprising one or more containers filled with one or more of the ingredients of the afore mentioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

In another embodiment, the kits may contain DNA sequences encoding the antibodies of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmids may also contain numerous other elements to facilitate cloning and expression of the encoded proteins. Such elements are well known to those of skill in the art and include, for example, selectable markers, initiation codons, termination codons, and the like.

Manufacture and Storage

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a lyophilized powder in 1-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of anti-coagulation factor XI and/or anti-coagualtion factor XIa antibodies, such labeling would include amount, frequency and method of administration.

IC50/EC50

According to the FDA, IC50 represents the concentration of a compound that is required for 50% inhibition of a given biological process. The antibodies of the present invention exhibit IC50 values 100 µM, preferably 1 µM, more preferred 0.1 µM, more preferred 0.01 µM, more preferred 0.001 µM, more preferred 0.0001 µM.

Therapeutically Effective Dose

Pharmaceutical compositions suitable for use in the present invention include compositions wherein the active ingredients are contained in an effective amount to achieve the intended purpose, i.e., treatment of a particular disease state characterized by the coagulation factor XI and/or the coagulation factor XIa. The determination of an effective dose is well within the capability of those skilled in the art.

A therapeutically effective dose refers to that amount of protein or its antibodies, antagonists, or inhibitors that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

The data obtained from cell culture assays and animal studies are used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks, or once within a month depending on half-life and clearance rate of the particular formulation.

Normal dosage amounts may vary from 0.1 to 100,000 micrograms, up to a total dose of about 2 g, depending upon the route of administration. Guidance as to particular dosages and methods of delivery is provided in the literature (see U.S. Pat. No. 6,300,064). Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabeled antibody may range from 0.1 to 10 mCi/mg of protein [WO 08/22295, U.S. Pat. Nos. 4,657,760; 5,206,344; 5,225,212; Riva P, Franceschi G, Frattarelli M, Lazzari S, Riva N, Giuliani G, Casi M, Sarti G, Guiducci G, Giorgetti G, Gentile R, Santimaria M, Jermann E, Maeke H R. (1999) Loco-regional radioimmunotherapy of high-grade malignant gliomas using specific monoclonal antibodies labeled with 90Y: a phase I study. Clin Cancer Res. 5(10 Suppl): 3275s-3280s].

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as [Sambrook J, Fritsch E F, Maniatis T. (1989) Molecular Cloning: A laboratory manual, Cold Spring Harbor Laboratory Press, Cold Spring Harbor, USA].

Measurement of the Coagulation Factor XI and/or the Coagulation Factor XIa Inhibition in Buffer To determine the factor Xa inhibition of the substance listed above, a biological test system is constructed in which the conversion of a factor XIa substrate is used for determining the enzymatic activity of human factor XIa. The determinations are carried out in microtitre plates.

Determination of the Anticoagulation Activity

The anticoagulation activity of the test substances is determined in vitro in human plasma and/or rabbit plasma and/or rat plasma. To this end, blood is drawn off in a mixing ratio of sodium citrate/blood of 1/9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Roche (former Boehringer Mannheim) or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effected a doubling of the prothrombin time is determined.

The thrombin time (TT) is determined in the presence of varying concentrations of test substance or the corresponding solvent using a commercial test kit (thrombin reagent from Roche). The test compounds are incubated with the plasma at 37° C. for 3 minutes. Coagulation is then started by addition of the thrombin reagent, and the time when coagulation occurs is determined. The concentration of test substance which effects a doubling of the thrombin time is determined.

The activated partial thromboplastin time (aPTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects a doubling of the aPTT is determined.

Concentrations of the antibodies of the present invention lead to a doubling of the aPTT at a concentration of 100 µM, preferably at a concentration of 1 µM, more preferred at a concentration of 0.1 µM, more preferred at a concentration of 0.01 µM, more preferred at a concentration of 0.001 µM, more preferred at a concentration of 0.0001 µM, more preferred at a concentration of 0.00001 µM.

Therapeutic Use

Anti-coagulation factor XI antibodies and/or anti-coagulation factor XIa antibodies of the invention may be administrated to any subject in which inhibition of the coagulation cascade and inhibition of platelet aggregation and inhibition of thrombosis would be beneficial.

Therefore, the anti-coagulation factor XI antibodies and/or anti-coagulation factor XIa antibodies of the invention are suitable for the treatment and/or prophylaxis of coagulation-related disease in humans as well as in animals.

The term "thromboembolic diseases" includes diseases like myocardial infarction (MI) or acute myocardial infarction (AMI) with and without ST elevation on ECG (STEMI and non-STEMI), stable Angina Pectoris as well as unstable Angina Pectoris, re-occlusion and re-stenosis following coronary intervention like angioplasty or coronary artery bypass graft (CABG), peripheral artery occlusive disease (PAOD), pulmonary embolism (PE), deep vein thrombosis (DVT) as well as renal vein thrombosis, transient ischemic attack (TIA), thrombotic stroke and thromboembolic stroke.

These antibodies are also useful for the treatment and prevention of cardiogenic thromboembolism like cerebral ischemia, apoplectic stroke as well as systemic thromboembolism, for the treatment of patients with irregular heartbeat or abnormal heart rhythm, e.g., for patients with atrial fibrillation, for patients with valvular heart disease of with artificial heart valves. Further on, these antibodies could be helpful in the treatment of patients with disseminated intravascular coagulation (DIC).

Thromboembolic complications may be caused by atherosclerotic lesions of the vessel wall, especially disturbance of endothelial function, which may lead to acute thrombotic occlusions. Atherosclerosis is a multifactorial disorder which depends on a large number of cardiovascular risk factors. Clinical studies have shown that prophylaxis with anticoagulants does not definitively influence the course of the arterial vascular disorder. Targeted treatment of the risk factors in conjunction with an antithrombotic therapy is therefore advantageous. Risk factors for coronary, peripheral and cerebral vascular disorders are, for example: elevated serum cholesterol levels, arterial hypertension, cigarette smoking, and diabetes mellitus. The principles of preventive medicine are based on elimination of these risk factors. Besides a change in lifestyle, also included are pharmacological measures such as, for example, antihypertensive therapy, lipid-lowering medicaments or thrombosis prophylaxis. In addition, combination with coronary therapeutic agents is suitable for the treatment where there is preexistent coronary heart disease.

Thromboembolic complications are involved in microangiopathic hemolytic anemia (MAHA), extracorporeal blood circulation like haemodialysis and aortic valve replacement.

In addition the antibodies of this invention are useful for the treatment or for prophylaxis of inflammatory diseases like rheumatoid arthritis (RA), or like neurological diseases like Alzheimer's disease (AD). Further on, these antibodies could be useful for the treatment of cancer and metastasis, thrombotic microangiopathy (TMA), age related macular degeneration, diabetic retinopathies, diabetic nephropathies, as well as other microvascular diseases.

The antibodies of this invention are also useful for the treatment of thromboembolic complications following the surgery of tumor patients or tumor patients undergo a chemo- and/or radiotherapy.

The antibodies of this invention are also useful for the treatment and/or prophylaxis of Dialysis patients, especially the Cimino-fistula prevention of shunt thrombosis in hemodialysis. Hemodialysis can be performed using native arteriovenous fistulae, synthetic loop grafts, large-bore central venous catheters or other devices consisting of artificial surfaces. Administration of antibodies of this invention will prevent the formation of clot within the fistula (and propagation of embolized clot in the pulmonary arteries), both during dialysis and shortly thereafter.

The antibodies of this invention are also useful for the treatment and/or prophylaxis of patients undergoing intracardiac and intrapulmonary thromboses after cardiopulmonary bypass surgeries (e.g., ECMO: Extra-corporeal membrane oxygenation).

Beneath the requirement for systemic anticoagulation, and the mechanical stability and duration of the device, major limitations of ventricular assist devices are the high incidence of thromboembolic events. Therefore, the antibodies of this invention are also useful for the treatment and/or prophylaxis of patients getting a left ventricular assist device.

There is a high need for anticoagulation in dialysis patients without increasing the risk of unwanted bleeding events and where the incidence of venous thromboembolism (VTE) and atrial fibrillation (e.g., end-stage renal disease in hemodialysis patients) in this population is high. The antibodies of this invention are also useful for the treatment and/or prophylaxis of these types of patients.

The antibodies of this invention are also useful for the treatment and/or prophylaxis of patients affected with idiopathic thrombocytopenic purpura (IPT). These patients have an increased thrombotic risk compared to the general population. The concentration of the coagulation factor FXI is significantly higher in ITP patients compared to controls and aPTT is significantly longer in ITP patients.

The antibodies of this invention are also useful for the treatment and/or prophylaxis of pulmonary hypertension.

The term "pulmonary hypertension" follows the guidelines defined by the World Health Organization WHO (Clinical Classification of Pulmonary Hypertension, Venice 2003), e.g., the pulmonary arterial hypertension, pulmonary hypertension caused by left ventricular disease, pulmonary hypertension caused by lung diseases and/or hypoxia, by blood clots, artery constriction, and other diseases like chronic thromboembolic pulmonary hypertension (CTEPH).

The term "pulmonary hypertension" also includes diseases like idiopathic pulmonary arterial hypertension IPAH, the familial pulmonary arterial hypertension (FPAH), the associated pulmonary arterial hypertension (APAH), which could be associated with collagenosis, congenital systemic pulmonary shunt vitia, HIV infections, or the administration of certain drugs in combination with diseases like thyroid diseases, Glycogen storage disease (GSD), Morbus Gaucher, hereditary hemorrhagic teleangiectasy, hemoglobinopathy, and/or myeloproliferative disorders.

The antibodies of this invention are useful for the treatment and/or the prophylaxis of diseases like pulmonary veno-occlusive disease, the plmonary capillary hemangiomatosis (PCH), as well as the persistent pulmonary hypertension of the newborn.

The term "pulmonary hypertension" also includes diseases like the chronic obstructive pulmonary disease (CODP), interstitial lung disease (ILD), sleep apnea, alveolar hyperventilation, altitude sickness, as well as constitutional dysplasia.

Diseases caused by chronic thromboembolic pulmonary hypertension (CTEPH) can be associated with proximal and/or distal pulmonary artery obstruction, or with non-thrombotic lung emboli like cancer, parasites, or contaminants.

Further on the antibodies of this invention can be used for the treatment and/or prophylaxis of the pulmonary hypertension caused by sarcoidosis, histiocytosis X, and lymphangiomatosis.

In addition, the antibodies of this invention may be useful for the treatment and/or prophylaxis of pulmonary and/or hepatic fibrosis.

The antibodies of this invention are also useful for the treatment and/or prophylaxis of sepsis, the systemic inflammatory syndrome (SIRS), organ dysfunction, multiple organ dysfunction syndrome (MODS) acute respiratory distress syndrome (ARDS), acute lung injury (ALI), disseminated intravascular coagulation (DIC).

The term "sepsis" defines the occurrence of an infection or of the systemic inflammatory response syndrome (SIRS). SIRS is mainly induced by infections, but can also take place following lesion, burn, shock, operations, ischemia, pancreatitis, reanimation or tumor affection. In the course of a sepsis, the coagulation cascade can be activated, a process termed as disseminated intravascular coagulation or shortly DIC. This can lead to the formation of microthrombi and to secondary complications.

In addition, sepsis or SIRS can lead to endothelial dysfunction, leading to an increase in permeability vessel. In the course of sepsis or SIRS, combined failure of several organs can take place, e.g., kidney failure, liver failure, lung failure, failure of the cardio-vascular system.

Pathogenic organism inducing sepsis or SIRS are gram-positive and gram-negative bacteria, fungi, viruses, and/or eukaryotic pathogens.

DIC and/or SIRS can occur in line with a sepsis, but can also occur due to an operation, tumor diseases, burning, or other types of injury.

During DIC, an activation of the coagulation cascade takes place ate the surface of damaged vessels or other types of tissues. This could lead to the formation of microthrombi, which on their part are leading to the occlusion of small vessels.

In one embodiment, the anti-coagulation factor XI antibodies and/or the anti-coagulation factor XIa antibodies is used in combination with other drugs for the treatment and/or prophylaxis of the already mentioned diseases.

In the following, examples for suitable combinations are listed up and therefore are preferable mentioned:

Combination with lipid lowering compounds, especially inhibitors of the 3-hydroxy-3-methyl-glutaryl-CoA reductase like Lovastatin (Mevacor; U.S. Pat. No. 4,231,938), Simvastatin (Zocor; U.S. Pat. No. 4,444,784), Pravastatin (Pravachol; U.S. Pat. No. 4,346,227), Fluvastatin (Lescol; U.S. Pat. No. 5,354,772), and Atorvastatin (Lipitor; U.S. Pat. No. 5,273,995).

Combination with compounds suitable for the treatment of coronary diseases and/or compounds exhibiting vasodilatative activities especially inhibitors of the angiotensin converting enzyme, like Captopril, Lisinopril, Enalapril, Ramipril, Cilazapril, Benazepril, Fosinopril, Quinapril, and Perindopril, or antagonists of the angiotensin II receptor like Embusartan (U.S. Pat. No. 5,863,930), Losartan, Valsartan, Irbesartan, Candesartan, Eprosartan, and Temisarta, or antagonists of the β-adrenergic receptor like Carvedilol, Alprenolol, Bisoprolol, Acebutolol, Atenolol, Betaxolol, Carteolol, Metoprolol, Nadolol, Penbutolol, Pindolol, Propanolol and Timolol, or the combination with antagonists of the alpha1 adrenergic receptor like Prazosin, Bunazosin, Doxazosin, and Terazosin.

Combination with diuretics Hydrochlorothiazide, Furosemide, Bumetanide, Piretanide, Torasemide, Amiloride, and Dihydralazine.

Combination with inhibitors of calcium channels like Verapamil and Diltiazem, dihydropyridine derivatives like Nifedipin (Adalat), Nitrendipin (Bayotensin), Isosorbid-5-mononitrat, Isosorbid-dinitrat, and Glyceroltrinitrat.

Combination with compounds which are leading to an increase in the concentration of cyclic guanosine monophosphate (cGMP) like stimulators of the soluble Guanylatcyclase (WO 98/16223, WO 98/16507, WO 98/23619, WO 00/06567, WO 00/06568, WO 00/06569, WO 00/21954, WO 00/66582, WO 01/17998, WO 01/19776, WO 01/19355, WO 01/19780, WO 01/19778, WO 07/045366, WO 07/045367, WO 07/045369, WO 07/045370, WO 07/045433).

Combination with other inhibitors of the coagulation cascade like Plasminogen activators (thrombolytics/Fibrinolytics) as well as compounds increasing Thrombolysis and/or Fibrinolysis or inhibitors of the plasminogen activator or inhibitors of the Thrombin-aktivierten Fibrinolyse-Inhibitors (TAFI-Inhibitoren) like the tissue plasminogen activator (t-PA), Streptokinase, Reteplase, and Urokinase.

Combination with anticoagulants like non-fractionated heparins, low molecular weight Heparins, Heparinoid, Hirudin, Bivalirudin and/or Argatroban.

Further combination therapies are the co-administration of the anti-coagulation factor XI antibodies and/or the anti-coagulation factor XIa antibodies with an antibiotic therapy, antifungal therapeutics, and antiviral therapeutics.

Additionally, combinations of the anti-coagulation factor XI antibodies and/or the anti-coagulation factor XIa antibodies with vasopressors like Norepinephrine, Dopamine, and Vasopressin inotropic therapies, e.g., Dobutamine corticosteroids, like hydrocortison or fludrocortisone recombinantly expressed activated protein C blood products, like fresh frozen plasma, erythrocyte concentrates, and/or thrombocyte concentrates Another embodiment of this invention is the usage of the anti-coagulation factor XI antibodies and/or anti-coagulation factor XIa antibodies as an anticoagulant for blood probes, blood preservations, other plasma products or biological samples, which contain the coagulation factor XI and/or the coagulation factor XIa. These samples are characterized in such a way, that an effective concentration of the antibodies has been added to avoid in vitro coagulation.

The anti-coagulation factor XI antibodies and/or anti-coagulation factor XIa antibodies of this invention can also be used for inhibition of ex vivo coagulation, like the preparation of blood catheters or other medicinal additives or devices, for the coating of artificial surfaces of in vivo as well as for ex vivo used medicinal additives, devices, or other biological samples, which contain the coagulation factor XI and/or the coagulation factor XIa.

EXAMPLE 1

Identification of Antibodies

Tools Used for Phage Selection:

Proteins used for the isolation of human antibodies of the present invention were obtained from different sources as listed in Table 1. Proteins were biotinylated using an appr. 2-fold molar excess of biotin-LC-NHS (Pierce; Cat. No. 21347) according to manufacturer's instructions and desalted using Zeba desalting columns (Pierce; Cat. No. 89889).

TABLE 1

List of proteins used in phage selections and screening:

| Protein | Origin | Supplier (Cat. No.) |
| --- | --- | --- |
| hFX | human | Haematologic Technologies Inc. (HCX-0050) |
| hFXa | human | Haematologic Technologies Inc. (HCXA-0060) |
| rbFX | rabbit | In house |
| rbFXa | rabbit | In house |
| hPrekallikrein | human | Enzyme Research Laboratories (HPK 2640 AL) |
| hKallikrein | human | Enzyme Research Laboratories (HPKA 1303) |
| Aprotinin | bovine | Sigma (A1153) |

Phage Selection:

The isolation of human antibodies of the present invention or antigen binding fragments thereof was performed by phage display technology employing DYAX's human Fab antibody library FAB-310 (DYAX Corp., Cambridge, Mass.; described in Hoet et al., Nat Biotech 2005, 23:344-8), which is a Fab library combining natural and synthetic diversity. Tables 2 to 6 summarizes different strategies that were employed to select antibodies covering multiple epitopes.

TABLE 2

Selection strategy I: Prior to each round of selection a depletion step on biotinylated Kallikrein/pre-Kallikrein (500 nM) was included.

| Round of selection: | Strategy IA | Strategy IB |
|---|---|---|
| 1 | 500 nM biotinylated hFXI | |
| 2 | 200 nM biotinylated hFXI | 200 nM biotinylated rbFXI |
| 3 | 100 nM biotinylated hFXI | 200 nM biotinylated hFXI |
| 4 | | 100 nM biotinylated rbFXI |

TABLE 3

Selection strategy II: As described for Strategy I, prior to each round of selection a depletion step on biotinylated Kallikrein/pre-Kallikrein (500 nM) was included. In addition selections were performed in the presence of the complex hFXIa (500 nM)/aprotinin (25 µM).

| Round of selection: | Strategy IIA | Strategy IIB |
|---|---|---|
| 1 | 500 nM biotinylated hFXI | |
| 2 | 200 nM biotinylated hFXI | 200 nM biotinylated rbFXI |
| 3 | 100 nM biotinylated hFXI | 200 nM biotinylated hFXI |
| 4 | | 100 nM biotinylated rbFXI |

TABLE 4

Selection strategy III: Prior to each round of selection a depletion step on biotinylated Kallikrein/pre-Kallikrein (500 nM) was included.

| Round of selection: | Strategy IIIA | Strategy IIIB |
|---|---|---|
| 1 | 500 nM biotinylated hFXIa | |
| 2 | 200 nM biotinylated hFXIa | 200 nM biotinylated rbFXIa |
| 3 | 100 nM biotinylated hFXIa | 200 nM biotinylated hFXIa |
| 4 | | 100 nM biotinylated rbFXIa |

TABLE 5

Selection strategy IV: As described for Strategy III, prior to each round of selection a depletion step on biotinylated Kallikrein/pre-Kallikrein (500 nM) was included. In addition selections were performed in the presence of the complex hFXIa (500 nM)/aprotinin (25 µM).

| Round of selection: | Strategy IVA | Strategy IVB |
|---|---|---|
| 1 | 500 nM biotinylated hFXIa | |
| 2 | 200 nM biotinylated hFXIa | 200 nM biotinylated rbFXIa |
| 3 | 100 nM biotinylated hFXIa | 200 nM biotinylated hFXIa |
| 4 | | 100 nM biotinylated rbFXIa |

TABLE 6

Selection strategy V: Prior to each round of selection depletion steps on biotinylated Kallikrein/pre-Kallikrein (500 nM) and biotinylated hFXI (500 nM) were included.

| Round of selection: | Strategy V |
|---|---|
| 1 | 500 nM biotinylated hFXIa |
| 2 | 200 nM biotinylated rbFXIa |
| 3 | 200 nM biotinylated hFXIa |
| 4 | 100 nM biotinylated rbFXIa |

Standard buffers used in this example are:
1×PBS: from Sigma (D5652-501)
PBST: 1×PBS supplemented with 0.05% Tween20 (Sigma, P7949)
Blocking buffer: PBST supplemented with 3% BSA (Sigma A4503)
Precipitation buffer: 20% PEG6000 (Calbiochem, 528877) in 2.5 M NaCl
Cell panning-buffer: PBS supplemented with 3% FBS (GIBCO, 10082) and 0.01% $NaN_3$ (Sigma, 71289)

The general method used for the library selection has been described by Hoet et. al. (Hoet R M, Cohen E H, Kent R B, Rookey K, Schoonbroodt S, Hogan S, Rem L, Frans N, Daukandt M, Pieters H, van Hegelsom R, Neer N C, Nastri H G, Rondon I J, Leeds J A, Hufton S E, Huang L, Kashin I, Devlin M, Kuang G, Steukers M, Viswanathan M, Nixon A E, Sexton D J, Hoogenboom H R, Ladner R C. (2005) Generation of high-affinity human antibodies by combining donor-derived and synthetic complementarity-determining-region diversity. Nat Biotechnol 23:344-348). Briefly, the Fab antibody library is precipitated by adding 1/5 volume of precipitation buffer followed by an incubation on ice for 1 h and a centrifugation step (1 h at 5500 rpm). The precipitated library was subsequently resuspended in 1 ml blocking buffer and incubated at r.t. for 30 min.

Meanwhile, aliquots of streptavidin-coated Dynabeads M280 (Invitrogen, 11206D) were prepared by washing 3 times with PBST. After that some aliquotes were mixed with biotinylated Kallikrein/pre-Kallikrein (500 nM) or biotinylated hFXI (500 nM) while the remaining were mixed with the biotinylated target protein as indicated in Tables 2 to 6. The mixtures were incubated ON at 4° C. on an end-to-end rotator and subsequently washed 5 times in 1 ml PBST. Coated beads were finally blocked by resuspension in 1 ml blocking buffer, aliquoted in 5 tubes followed by collection of the beads and removal of the supernatant.

5 sequential depletion steps were done as indicated by adding the blocked library (described above) to blocked Dynabeads coated with biotinylated Kallikrein/pre-Kallikrein (500 nM) or biotinylated hFXI (500 nM) and incubated at r.t. for 10 min while rotating. After collection of the beads on a magnetic rack, the supernatant was cleared by centrifugation and mixed with blocked Dynabeads coated with target protein. After 30 min incubation on an end-to-end rotator the samples were washed 3 times with blocking buffer followed by 9 times washing with PBST. Half of the resuspended beads containing enriched phages were then used to infect exponentially growing E. coli TG1 (from Stratagene) for preparation of new phage stocks used in the next selection round according to the strategies depicted in Tables 2 to 6. In more detail, 6 ml of TG1-culture were infected with 500 µl of dynabead/phage suspension for 30 min at 37° C. without shaking. After that aliquots were taken for output tirtration. The remaining culture was centrifuged for 15 min at 5000 rpm and the resulting pellet was resuspended in 2 ml 2×YT and plated on agar plates (2×YT, 100 µg/ml ampicillin, 2% glucose). After overnight incubation at 37° C., cells were scraped off in 5 ml 2×YT and used to inoculate a fresh culture of 20 ml 2×YT (100 µg/ml Amp) at an OD600 of 0.05 and for the preparation of glycerol stocks. The fresh liquid culture was shaked for about 2 h at 37° C. until OD600 0.5 to 0.8 was reached, then 5 ml culture were mixed with M13 helperphage M123K07 (Invitogen 420311) at an multiplicity of infection (MOI) of about 20. After slow shaking for 30 min at 37° C. 30 ml prewarmed 2×YT (100 µg/ml ampicillin, 20 µg/ml kanamycin, f.c.) was added and the culture skaked ON at 30° C. Next morning the supernatant was harvested by centrifugation at 6000 rpm and cleared by filtration through Steriflip (0.22 µm; Milipore SCGP00525). Subsequently, phages were precipitated as described above and resuspended in 1 ml blocking buffer (or cell panning buffer) for use in the next selection round. Aliquots were used for the determination of the input titer.

Enzyme-Linked Immunosorbent Assay (ELISA):

Phage ELISA

Phage pools after different rounds of selection were analyzed for the enrichment of specific binder by ELISA on biotinylated target proteins. Briefly, aliquots from the glycerol stocks were plated on 2×YT (100 mg/ml ampicillin, 1% glucose) ON at 37° C. Single colonies were picked into wells of MTP containing 100 µl medium (2×YT, 100 µg/ml ampicillin, 1% glucose) and shaked overnight at 37° C. Phage expression was performed by adding 10 µl of overnight culture to 190 µl fresh medium (2×YT supplemented with 100 µg/ml ampicillin) containing helperphage M123K07 (Invitogen 420311) and incubating at 200 rpm and 37° C. in 96-well MTP until an OD600 of ~0.5 was reached.

96-well ELISA-plates pre-coated with streptavidin (Pierce, 15500) were coated over night at 4° C. with 1 µg/ml biotinylated target protein. The next day plates were washed 7 times with PBST, treated with blocking reagent, and washed again 3 times with PBST. Meanwhile, ON phage cultures were mixed with 100 µl blocking buffer. After that 100 µl of the blocked phages were transferred per well and incubated for 1 hr at r.t. After washing 7 times with PBST, anti M13 antibody coupled to HRP (GE Healthcare, 27-9421-01; 1:2500 diluted in PBST) was added, incubated for 1 hr at r.t. and wells were washed again 7 times. Color reaction was developed by addition of 100 µl TMB (Invitrogen, 2023) and stopped after 5-15 min by adding 100 µl $H_2SO_4$ (Merck, 1120801000). Colorimetric reaction was recorded at 450 nM in a plate reader (Tecan).

comprised of a light chain variable region and a heavy chain variable region. Variants of the antibodies or antigen-binding fragments contemplated in the invention are molecules in which the binding activity of the antibody or antigen-binding antibody fragment for the coagulation factor XI and/or the coagulation factor XIa are maintained.

The present invention provides antibodies or antigen-binding fragments:

whereby the amino acid sequences of the variable heavy and light regions are at least 60%, more preferred 70%, more preferred 80%, or 90%, or even more preferred 95% identical to SEQ ID NO: 1 for the DNA sequence and SEQ ID NO: 19 for the amino acid sequence for the variable light chain domain and, identical to SEQ ID NO: 2 for the DNA sequence and 20 for the amino acid sequence for the variable heavy chain domain, or whereby for the maturated forms of these antibodies the amino acid sequences of the variable heavy chain and light chain domain are at least 60%, more preferred 70%, more preferred 80%, or 90%, or even more preferred 95% identical thereto whereby the amino acid sequences of the CDRs are at least 60%, more preferred 70%, more preferred 80%, more preferred 90%, or even more preferred 95% identical to SEQ ID NOs: 3, 4 and 5 for the DNA sequence and SEQ ID NOs: 21, 22 and 23 for the amino acid sequence for the heavy chain domain, and to SEQ ID NOs: 6, 7, and 8 for the DNA sequence SEQ ID NOs: 24, 25, and 26 for the amino acid sequence for the variable light chain domain.

The present invention further provides antibodies or antigen-binding fragments:

whereby the amino acid sequences of the variable heavy and light regions are at least 60%, more preferred 70%,

TABLE 7

Hit rates of pools from different strategies in Fab/Phage ELISA: numbers refer to % hit rate on human/rabbit/both targets (crossreactive), respectively (n.a.: not applicable).

| | IA | IB | IIA | IIB | IIIA | IIIB | IVA | IVB | V |
|---|---|---|---|---|---|---|---|---|---|
| $2^{nd}$ round | 3/1/0 | 1/0/0 | 6/5/4 | 0/1/0 | 1/1/0 | 1/0/0 | 0/0/0 | 0/0/0 | 0/0/0 |
| $3^{rd}$ round | 77/20/18 | 22/18/16 | 80/30/31 | 41/28/32 | 35/8/3 | 11/18/9 | 35/3/0 | 10/13/10 | 13/23/9 |
| $4^{th}$ round | n.a. | 74/72/63 | n.a. | 80/84/67 | n.a. | 42/72/34 | n.a. | 86/90/73 | 65/70/53 |

Recloning of sFabs by GenIII-Removal for sFab Screening

For the generation of soluble Fab fragments (sFabs) phagemid DNA from selection rounds 2, 3 and 4 was isolated and digested with restriction enzymes MluI (New England Biolabs, R0198L) according to the providers instructions. In order to remove the gene III containing fragment the vector was gele-extracted and submitted to a kill-cut with NdeI (New England Biolabs, R0111S). After EtOH-precipitation the resulting fragment was re-ligated and constructs were transformed into chemically competent *E. coli* Top 10 using standard methods.

EXAMPLE 2

Anti-Coagulation Factor XI Antibodies and/or Anti-Coagulation Factor XIa Antibodies The antibodies, antigen-binding antibody fragments, and variants of the antibodies and fragments of the invention are more preferred 80%, or 90%, or even more preferred 95% identical to SEQ ID NO: 9 for the DNA sequence and SEQ ID NO: 27 for the amino acid sequence for the variable light chain and, identical to SEQ ID NO: 2 for the DNA sequence and 20 for the amino acid sequence for the variable heavy chain domain, or whereby for the maturated forms of these antibodies the amino acid sequences of the variable heavy chain and light chain domain are at least 60%, more preferred 70%, more preferred 80%, or 90%, or even more preferred 95% identical thereto whereby the amino acid sequences of the CDRs are at least 60%, more preferred 70%, more preferred 80%, more preferred 90%, or even more preferred 95% identical to SEQ ID NO: 10 for the DNA sequence and SEQ ID NO: 28 for the amino acid sequence for the variable light chain domain.

The present invention also provides antibodies or antigen-binding fragments:

whereby the amino acid sequences of the variable heavy and light regions are at least 60%, more preferred 70%, more preferred 80%, or 90%, or even more preferred 95% identical to SEQ ID NO: 11 for the DNA sequence and SEQ ID NO: 29 for the amino acid sequence for the variable light chain domain and, identical to SEQ ID NO: 12 for the DNA sequence and 30 for the amino acid sequence for the variable heavy chain domain, or whereby for the maturated forms of these antibodies the amino acid sequences of the variable heavy chain and light chain domain are at least 60%, more preferred 70%, more preferred 80%, or 90%, or even more preferred 95% identical thereto whereby the amino acid sequences of the CDRs are at least 60%, more preferred 70%, more preferred 80%, more preferred 90%, or even more preferred 95% identical to SEQ ID NOs: 13, 14 and 15 for the DNA sequence and SEQ ID NOs: 31, 32, and 33 for the amino acid sequence for the heavy chain domain, and to SEQ ID NOs: 16, 17, and 18 for the DNA sequence SEQ ID NOs: 34, 35, and 36 for the amino acid sequence for the variable light chain domain.

EXAMPLE 3

Determination of the Anticoagulation Activity Using the Activated Partial Thromboplastin Time (aPTT) Assay The anticoagulation activity of the antibodies 076D-M007-H04, 076D-M007-H04-CDRL3-N110D, and 076D-M028-H17 were tested by using the activated partial thromboplastin time (aPTT) assay.

Values for the concentrations needed for doubling the aPTT in human and in rabbit plasma are given in Table 8.

TABLE 8

Antibody concentrations needed for doubling the aPTT of human and rabbit plasma.

|  | 2xaPTT human [μM] | 2xaPTT rabbit [μM] |
| --- | --- | --- |
| 076D-M028-H17 | 0.3 | 0.003 |
| M076D-M007-H04 | 0.9 | 0.178 |
| 076D-M007-H04-CDRL3-N110D | 0.3 | 0.063 |

TABLE 9

Examples and sequences of antibodies of the present invention.

| Description | SEQ ID NO | type | Sequence |
| --- | --- | --- | --- |
| H04-Vl | 1 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTATC AGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGAACAGCTTTCCGGTGACCTT TGGCGGCGGCACCAAAGTGGAAATTAAA |
| H04-Vh | 2 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCAGTATGGCATGGATTGG GTGCGCCAGGCGCCGGGCAAAGGCCTGGAATGGGT GAGCGGCATTGGCCCGAGCGGCGGCAGCACCGTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCA CCCGCGGCGGCCCGTATTATTATTATGGCATGGATGT GTGGGGCCAGGGCACCACCGTGACCGTGAGCAGC |
| H04 CDR H1 | 3 | DNA | GGCTTTACCTTTAGCCAGTATGGCATGGAT |
| H04 CDR H2 | 4 | DNA | GGCATTGGCCCGAGCGGCGGCAGCACCGTG |
| H04 CDR H3 | 5 | DNA | ACCCGCGGCGGCCCGTATTATTATTATGGCATGGATG TG |
| H04 CDR L1 | 6 | DNA | CAGGCGAGCCAGGATATTAGCAACTATCTGAAC |
| H04 CDR L2 | 7 | DNA | GATGCGAGCAACCTGGAAACC |
| H04 CDR L3 | 8 | DNA | CAGCAGGCGAACAGCTTTCCG |

TABLE 9-continued

Examples and sequences of antibodies of the present invention.

| Description | SEQ ID NO | type | Sequence |
|---|---|---|---|
| N110D-Vl | 9 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTAT CAGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGGATAGCTTTCCGGTGACCTT TGGCGGCGGCACCAAAGTGGAAATTAAA |
| N110D-CDR L3 | 10 | DNA | CAGCAGGCGGATAGCTTTCCG |
| H17-Vl | 11 | DNA | GATATTCAGATGACCCAGAGCCCGAGCAGCGTGAGC GCGAGCGTGGGCGATCGCGTGACCATTACCTGCCGC GCGAGCCAGGGCATTAGCAGCTGGCTGGCGTGGTAT CAGCAGCGCCCGGGCAAAGCGCCGAAACTGCTGATT TATGATGCGAGCACCCTGCAGAGCGGCGTGCCGAGC CGCTTTAGCGGCAGCGGCAGCGGCACCGATTTTACC CTGACCATTAACAGCCTGCAGCCGGAAAACTTTGCGA CCTATTATTGCCAGCAGGCGGATAGCTTTCCGATTGC GTTTGGCCAGGGCACCCGCCTGGAAATTAAA |
| H17-Vh | 12 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCGATTATGAAATGGCGTGG GTGCGCCAGGCGCCGGGCAAAGGCCTGGAATGGGT GAGCAGCATTGTGCCGAGCGGCGGCTGGACCCTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCG CGACCTGGGGCGATAGCTGGGGCTTTGATTTTTGGG GCCAGGGCACCCTGGTGACCGTGAGCAGC |
| H17 CDR H1 | 13 | DNA | GGCTTTACCTTTAGCGATTATGAAATGGCG |
| H17 CDR H2 | 14 | DNA | AGCATTGTGCCGAGCGGCGGCTGGACCCTG |
| H17 CDR H3 | 15 | DNA | GCGACCTGGGGCGATAGCTGGGGCTTTGATTTT |
| H17 CDR L1 | 16 | DNA | CGCGCGAGCCAGGGCATTAGCAGCTGGCTGGCG |
| H17 CDR L2 | 17 | DNA | GATGCGAGCACCCTGCAGAGC |
| H17 CDR L3 | 18 | DNA | CAGCAGGCGGATAGCTTTCCGATTGCGTTTGGC |
| H04-Vl aa | 19 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| H04-Vh aa | 20 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYYGMDVWGQ GTTVTVSS |
| H04 CDR H1 aa | 21 | PRT | GFTFSQYGMD |

TABLE 9-continued

Examples and sequences of antibodies of the present invention.

| Description | SEQ ID NO | type | Sequence |
|---|---|---|---|
| H04 CDR H2 aa | 22 | PRT | GIGPSGGSTV |
| H04 CDR H3 aa | 23 | PRT | TRGGPYYYYGMDV |
| H04 CDR L1 aa | 24 | PRT | QASQDISNYLN |
| H04 CDR L2 aa | 25 | PRT | DASNLET |
| H04 CDR L3 aa | 26 | PRT | QQANSFP |
| N110D-V1 aa | 27 | PRT | DIQMTQSPSSLSASVGDRVTITCQASQDISNYLNWYQQK PGKAPKLLIYDASNLETGVPSRFSGSGSGTDFTFTISSLQ PEDIATYYCQQADSFPVTFGGGTKVEIK |
| N110D-CDR L3 | 28 | PRT | QQADSFP |
| H17-V1 aa | 29 | PRT | DIQMTQSPSSVSASVGDRVTITCRASQGISSWLAWYQQ RPGKAPKLLIYDASTLQSGVPSRFSGSGSGTDFTLTINSL QPENFATYYCQQADSFPIAFGQGTRLEIK |
| H17-Vh aa | 30 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17 CDR H1 aa | 31 | PRT | GFTFSDYEMA |
| H17 CDR H2 aa | 32 | PRT | SIVPSGGWTL |
| H17 CDR H3 aa | 33 | PRT | ATWGDSWGFDF |
| H17 CDR L1 aa | 34 | PRT | RASQGISSWLA |
| H17 CDR L2 aa | 35 | PRT | DASTLQS |
| H17 CDR L3 aa | 36 | PRT | QQADSFPIAFG |
| M009-G02-Vh | 37 | DNA | GAAGTGCAGCTGCTGGAAAGCGGCGGCGGCCTGGTG CAGCCGGGCGGCAGCCTGCGCCTGAGCTGCGCGGGC GAGCGGCTTTACCTTTAGCCGCTATATTATGCATTGG |

TABLE 9-continued

Examples and sequences of antibodies of the present invention.

| Description | SEQ ID NO | type | Sequence |
|---|---|---|---|
| | | | GTGCGCCAGGCGCCGGGCAAAGGCCTGGAATGGGT
GAGCAGCATTAGCCCGAGCGGCGGCCTGACCAGCTA
TGCGGATAGCGTGAAAGGCCGCTTTACCATTAGCCGC
GATAACAGCAAAAACACCCTGTATCTGCAGATGAACA
GCCTGCGCGCGGAAGATACCGCGGTGTATTATTGCG
CGCGCGAATTTGAAAACGCGTATCATTATTATTATTAT
GGCATGGATGTGTGGGGCCAGGGCACCACCGTGACC
GTGAGCAGC |
| M009-G02-Vl | 38 | DNA | GATATTCAGATGACCCAGAGCCCGAGCAGCCTGAGC
GCGAGCGTGGGCGATCGCGTGACCATTACCTGCCGC
GCGAGCGGCGATATTGGCAACGCGCTGGGCTGGTAT
CAGCAGAAACCGGGCAAAGCGCCGCGCCTGCTGATT
AGCGATGCGAGCACCCTGCAGAGCGGCGTGCCGCTG
CGCTTTAGCGGCAGCGGCAGCGGCACCGAATTTACC
CTGACCATTAGCAGCCTGCAGCCGGAAGATTTTGCGA
CCTATTATTGCCTGCAGGGCTATAACTATCCGCGCAC
CTTTGGCCAGGGCACCAAACTGGAAATTCGC |
| G16-Vh | 39 | DNA | GAAGTGCAGCTGCTGGAAAGCGGCGGCGGCCTGGTG
CAGCCGGGCGGCAGCCTGCGCCTGAGCTGCGCGGC
GAGCGGCTTTACCTTTAGCTGGTATCCGATGCAGTGG
GTGCGCCAGGCGCCGGGCAAAGGCCTGGAATGGGT
GAGCGGCATTAGCAGCAGCGGCGGCGGCACCTATTA
TGCGGATAGCGTGAAAGGCCGCTTTACCATTAGCCGC
GATAACAGCAAAAACACCCTGTATCTGCAGATGAACA
GCCTGCGCGCGGAAGATACCGCGGTGTATTATTGCG
CGCGCGATTGGGGCTATAGCAACTATGTGATGGATCT
GGGCCTGGATTATTGGGGCCAGGGCACCCTGGTGAC
CGTGAGCAGC |
| G16-Vl | 40 | DNA | GATATTCAGATGACCCAGAGCCCGGCGACCCTGAGC
CTGAGCCCGGGCGAACGCGCGACCCTGAGCTGCCG
CGCGAGCCAGACCGTGAGCAGCAGCCTGGCGTGGTA
TCAGCATAAACCGGGCCAGGCGCCGCGCCTGCTGAT
TTATGAAACCAGCAACCGCGCGACCGGCATTCCGGC
GCGCTTTAGCGGCAGCGGCAGCGGCACCGATTTTAC
CCTGACCATTAGCAGCCTGGAACCGGAAGATTTTGCG
GTGTATTATTGCCAGCATCGCAGCAACTGGCCGCCGA
CCTTTGGCCCGGGCACCAAAGTGGATATTAAA |
| G11-Vh | 41 | DNA | GAAGTGCAGCTGCTGGAAAGCGGCGGCGGCCTGGTG
CAGCCGGGCGGCAGCCTGCGCCTGAGCTGCGCGGC
GAGCGGCTTTACCTTTAGCACCTATAGCATGGGCTGG
GTGCGCCAGGCGCCGGGCAAAGGCCTGGAATGGGT
GAGCAGCATTAGCCCGAGCGGCGGCGATACCGATTA
TGCGGATAGCGTGAAAGGCCGCTTTACCATTAGCCGC
GATAACAGCAAAAACACCCTGTATCTGCAGATGAACA
GCCTGCGCGCGGAAGATACCGCGGTGTATTATTGCG
CGCGCGAACGCACCATGGTGCGCGATCCGCGCTATT
ATGGCATGGATGTGTGGGGCCAGGGCACCACCGTGA
CCGTGAGCAGC |
| G11-Vl | 42 | DNA | GATATTCAGATGACCCAGAGCCCGGCGACCCTGAGC
CTGAGCCCGGGCGAACGCGCGACCCTGAGCTGCCG
CGCGAGCCAGAGCGTGAGCAGCTATCTGGCGTGGTA
TCAGCAGCGCCTGGGCCAGAGCCCGCGCCTGCTGAT
TTATGATGCGAGCAGCCGCGCGACCGGCATTCCGGC
GCGCTTTAGCGGCAGCGGCAGCGGCACCGATTTTAC
CCTGACCATTAGCAGCCTGCAGCCGGAAGATTTTGCG
ACCTATTATTGCCAGCAGAGCTATAGCAACCTGGTGA
CCTTTGGCCAGGGCACCCGCCTGGAAATTAAA |
| M014-G02-Vh | 43 | DNA | GAAGTGCAGCTGCTGGAAAGCGGCGGCGGCCTGGTG
CAGCCGGGCGGCAGCCTGCGCCTGAGCTGCGCGGC
GAGCGGCTTTACCTTTAGCCTGTATTATATGAAATGGG
TGCGCCAGGCGCCGGGCAAAGGCCTGGAATGGGTGA
GCAGCATTAGCCCGAGCGGCGGCTTTACCAGCTATG
CGGATAGCGTGAAAGGCCGCTTTACCATTAGCCGCGA
TAACAGCAAAAACACCCTGTATCTGCAGATGAACAGC
CTGCGCGCGGAAGATACCGCGGTGTATTATTGCGCG
CGCGAATTTGAAAACGCGTATCATTATTATTATTATGG
CATGGATGTGTGGGGCCAGGGCACCACCGTGACCGT
GAGCAGC |

TABLE 9-continued

Examples and sequences of antibodies of the present invention.

| Description | SEQ ID NO | type | Sequence |
|---|---|---|---|
| M014-G02-Vl | 44 | DNA | GATATTCAGATGACCCAGAGCCCGAGCAGCGTGAGC<br>GCGAGCGTGGGCGATCGCGTGACCATTACCTGCCGC<br>GCGAGCCAGGATATTAACATTTGGCTGGCGTGGTATC<br>AGCAGAAACCGGGCAAAGCGCCGAAACTGCTGATTA<br>GCGCGGCGAGCACCGTGCAGAGCGGCGTGCCGAGC<br>CGCTTTAGCGGCAGCGGCAGCGGCACCGATTTTACC<br>CTGACCATTAACACCCTGCAGCCGGATGATTTTGCGA<br>CCTATTATTGCCAGCAGGCGGCGAGCTTTCCGCTGAC<br>CTTTGGCGGCGGCACCAAAGTGGAAATGAAA |
| M013-J04-Vh | 45 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCACCTATAGCATGGGCTGG<br>GTGCGCCAGGCGCCGGGCAAAGGCCTGGAATGGGT<br>GAGCAGCATTAGCCCGAGCGGCGGCGATACCGATTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGAACGCACCATGGTGCGCGATCCGCGCTATT<br>ATGGCATGGATGTGTGGGGCCAGGGCACCACCGTGA<br>CCGTGAGCAGC |
| M013-J04-Vl | 46 | DNA | GATATTCAGATGACCCAGAGCCCGGGCGACCCTGAGC<br>CTGAGCCCGGGCGAACGCGCGACCCTGAGCTGCCG<br>CGCGAGCCAGAGCGTGAGCAGCTATCTGGCGTGGTA<br>TCAGCAGCGCCTGGGCCAGAGCCCGCGCCTGCTGAT<br>TTATGATGCGAGCAGCCGCGCGACCGGCATTCCGGC<br>GCGCTTTAGCGGCAGCGGCAGCGGCACCGATTTTAC<br>CCTGACCATTAGCAGCCTGCAGCCGAAAGATTTTGCG<br>ACCTATTATTGCCAGCAGAGCTATAGCAACCTGGTGA<br>CCTTTGGCCAGGGCACCCGCCTGGAAATTAAA |
| A10-Vh | 47 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCTGGTATCCGATGCAGTGG<br>GTGCGCCAGGCGCCGGGCAAAGGCCTGGAATGGGT<br>GAGCGGCATTAGCAGCAGCGGCGGCGGCACCTATTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGATTGGGGCTATAGCAACTATGTGATGGATCT<br>GGGCCTGGATTATTGGGGCCAGGGCACCCTGGTGAC<br>CGTGAGCAGC |
| A10-Vl | 48 | DNA | GATATTCAGATGACCCAGAGCCCGGGCGACCCTGAGC<br>CTGAGCGCGGGCGAACGCGCGACCCTGAGCTGCCG<br>CGCGAGCCAGACCGTGAGCAGCAGCCTGGCGTGGTA<br>TCAGCATAAACCGGGCCAGGCGCCGCGCCTGCTGAT<br>TTATGAAACCAGCAACCGCGCGACCGGCATTCCGGC<br>GCGCTTTAGCGGCAGCGGCAGCGGCACCGATTTTAC<br>CCTGACCATTAGCAGCCTGGAACCGGAAGATTTTGCG<br>GTGTATTATTGCCAGCATCGCAGCAACTGGCCGCCGA<br>CCTTTGGCCCGGGCACCAAAGTGGATATTAAA |
| M10-Vh | 49 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCTGGTATCCGATGCAGTGG<br>GTGCGCCAGGCGCCGGGCAAAGGCCTGGAATGGGT<br>GAGCGGCATTAGCAGCAGCGGCGGCGGCACCTATTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGATTGGGGCTATAGCAACTATGTGATGGATCT<br>GGGCCTGGATTATTGGGGCCAGGGCACCCTGGTGAC<br>CGTGAGCAGC |
| M10-Vl | 50 | DNA | GATATTCAGATGACCCAGAGCCCGGGCGACCCTGAGC<br>CTGAGCGCGGGCGAACGCGCGACCCTGAGCTGCCG<br>CGCGAGCCAGACCGTGAGCAGCAGCCTGGCGTGGTA<br>TCAGCATAAACCGGGCCAGGCGCCGCGCCTGCTGAT<br>TTATGAAACCAGCAACCGCGCGACCGGCATTCCGGC<br>GCGCTTTAGCGGCAGCGGCAGCGGCACCGATTTTAC<br>CCTGACCATTAGCAGCCTGGAACCGGAAGATTTTGCG<br>GTGTATTATTGCCAGCATCGCAGCAACTGGCCGCCGA<br>CCTTTGGCCCGGGCACCAAAGTGGATATTAAA |

TABLE 9-continued

Examples and sequences of antibodies of the present invention.

| Description | SEQ ID NO | type | Sequence |
|---|---|---|---|
| H15-Vh | 51 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCACCTATAGCATGGGCTGG<br>GTGCGCCAGGCGCCGGGCAAAGGCCTGGAATGGGT<br>GAGCAGCATTAGCCCGAGCGGCGGCGATACCGATTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGAACGCACCATGGTGCGCGATCCGCGCTATT<br>ATGGCATGGATGTGTGGGGCCAGGGCACCACCGTGA<br>CCGTGAGCAGC |
| H15-Vl | 52 | DNA | GATATTCAGATGACCCAGAGCCCGGCGACCCTGAGC<br>CTGAGCCCGGGCGAACGCGCGACCCTGAGCTGCCG<br>CGCGAGCCAGAGCGTGAGCAGCTATCTGGCGTGGTA<br>TCAGCAGCGCCTGGGCCAGAGCCCGCGCCTGCTGAT<br>TTATGATGCGAGCAGCCGCGCGACCGGCATTCCGGC<br>GCGCTTTAGCGGCAGCGGCAGCGGCACCGATTTTAC<br>CCTGACCATTAGCAGCCTGCAGCCGGAAGATTTTGCG<br>ACCTATTATTGCCAGCAGAGCTATAGCAACCTGGTGA<br>CCTTTGGCCAGGGCACCCGCCTGGAAATTAAA |
| F11-Vh- | 53 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCAACTATATGATGACCTGG<br>GTGCGCCAGGCGCCGGGCAAAGGCCTGGAATGGGT<br>GAGCGGCATTTATCCGAGCGGCGGCTTTACCCAGTAT<br>GCGGATAGCGTGAAAGGCCGCTTTACCATTAGCCGC<br>GATAACAGCAAAAACACCCTGTATCTGCAGATGAACA<br>GCCTGCGCGCGGAAGATACCGCGACCTATTATTGCG<br>CGCGCGATGCGAGCGATGTGTGGCTGCGCTTTCGCG<br>GCGGCGGCGCGTTTGATATTTGGGGCCAGGGCACCA<br>TGGTGACCGTGAGCAGC |
| F11-Vl | 54 | DNA | GATATTCAGATGACCCAGAGCCCGACCAGCCTGAGC<br>GCGAGCGTGGGCGATCGCGTGGCGATTACCTGCCGC<br>GCGAGCCAGAGCATTGATACCTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGTTTGATGATCTGCCGCTGACCTTT<br>GGCCCGGGCACCCGCGTGGATATTAAA |
| K12-Vh | 55 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCGCTATATTATGCATTGG<br>GTGCGCCAGGCGCCGGGCAAAGGCCTGGAATGGGT<br>GAGCAGCATTAGCCCGAGCGGCGGCCTGACCAGCTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGAATTTGAAAACGCGTATCATTATTATTATTAT<br>GGCATGGATGTGTGGGGCCAGGGCACCACCGTGACC<br>GTGAGCAGC |
| K12-Vl | 56 | DNA | GATATTCAGATGACCCAGAGCCCGAGCAGCCTGAGC<br>GCGAGCGTGGGCGATCGCGTGACCATTACCTGCCGC<br>GCGAGCGGCGATATTGGCAACGCGCTGGGCTGGTAT<br>CAGCAGAAACCGGGCAAAGCGCCGCGCCTGCTGATT<br>AGCGATGCGAGCACCCTGCAGAGCGGCGTGCCGCTG<br>CGCTTTAGCGGCAGCGGCAGCGGCACCGAATTTACC<br>CTGACCATTAGCAGCCTGCAGCCGGAAGATTTTGCGA<br>CCTATTATTGCCTGCAGGGCTATAACTATCCGCGCAC<br>CTTTGGCCAGGGCACCAAACTGGAAATTCGC |
| O15-Vh | 57 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCGCTATATTATGCATTGG<br>GTGCGCCAGGCGCCGGGCAAAGGCCTGGAATGGGT<br>GAGCAGCATTAGCCCGAGCGGCGGCCTGACCAGCTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG |

TABLE 9-continued

Examples and sequences of antibodies of the present invention.

| Description | SEQ ID NO | type | Sequence |
|---|---|---|---|
| | | | CGCGCGAATTTGAAAACGCGTATCATTATTATTAT<br>GGCATGGATGTGTGGGGCCAGGGCACCACCGTGACC<br>GTGAGCAGC |
| O15-<br>Vl | 58 | DNA | GATATTCAGATGACCCAGAGCCCGAGCAGCCTGAGC<br>GCGAGCGTGGGCGATCGCGTGACCATTACCTGCCGC<br>GCGAGCGGCGATATTGGCAACGCGCTGGGCTGGTAT<br>CAGCAGAAACCGGGCAAAGCGCCGCGCCTGCTGATT<br>AGCGATGCGAGCACCCTGCAGAGCGGCGTGCCGCTG<br>CGCTTTAGCGGCAGCGGCAGCGGCACCGAATTTACC<br>CTGACCATTAGCAGCCTGCAGCCGGAAGATTTTGCGA<br>CCTATTATTGCCTGCAGGGCTATAACTATCCGCGCAC<br>CTTTGGCCAGGGCACCAAACTGGAAATTCGC |
| A08-<br>Vh | 59 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCGAATATGGCATGATTTGG<br>GTGCGCCAGGCGCCGGGCAAAGGCCTGGAATGGGT<br>GAGCTTTATTAGCCCGAGCGGCGGCACCACCTTTTAT<br>GCGGATAGCGTGAAAGGCCGCTTTACCATTAGCCGC<br>GATAACTTTAAAAACACCCTGTATCTGCAGATGAACAG<br>CCTGCGCGCGGAAGATACCGCGGTGTATTATTGCGC<br>GCGCGGCGGCGGCAACTGGAACCATCGCCGCGCGC<br>TGAACGATGCGTTTGATATTTGGGGCCAGGGCACCAT<br>GGTGACCGTGAGCAGC |
| A08-<br>Vl | 60 | DNA | GATATTCAGATGACCCAGAGCCCGAGCAGCCTGAGC<br>GCGAGCGTGGGCGATCGCATTACCATTACCTGCCGC<br>GCGAGCCAGGCGATTCGCGATGATTTTGGCTGGTATC<br>AGCAGAAACCGGGCAAAGCGCCGAAACTGCTGATTTA<br>TGCGGCGAGCAGCCTGCAGAGCGGCGTGCCGAGCC<br>GCTTTAGCGGCAGCGGCAGCGGCACCGATTTTACCC<br>TGACCATTAGCAGCCTGCAGCCGGAAGATTTTGCGAC<br>CTATTATTGCCAGCAGAGCTATAGCACCCCGCTGACC<br>TTTGGCGGCGGCACCAAAGTGGAAATTAAA |
| E12-<br>Vh | 61 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCACCTATAGCATGGGCTGG<br>GTGCGCCAGGCGCCGGGCAAAGGCCTGGAATGGGT<br>GAGCAGCATTAGCCCGAGCGGCGGCGATACCGATTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGAACGCACCATGGTGCGCGATCCGCGCTATT<br>ATGGCATGGATGTGTGGGGCCAGGGCACCACCGTGA<br>CCGTGAGCAGC |
| E12-<br>Vl | 62 | DNA | GATATTCAGATGACCCAGAGCCCGGCGACCCTGAGC<br>CTGAGCCCGGGCGAACGCGCGACCCTGAGCTGCCG<br>CGCGAGCCAGAGCGTGAGCAGCTATCTGGCGTGGTA<br>TCAGCAGCGCCTGGGCCAGAGCCCGCGCCTGCTGAT<br>TTATGATGCGAGCAGCCGCGCGACCGGCATTCCGGC<br>GCGCTTTAGCGGCAGCGGCAGCGGCACCGATTTTAC<br>CCTGACCATTAGCAGCCTGCAGCCGGAAGATTTTGCG<br>ACCTATTATTGCCAGCAGAGCTATAGCAACCTGGTGA<br>CCTTTGGCCAGGGCACCCGCCTGGAAATTAAA |
| Y111W-<br>Vh | 63 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA<br>CCCGCGGCGGCCCGTATTATTATTGGGGCATGGATGT<br>GTGGGGCCAGGGCACCACCGTGACCGTGAGCAGC |
| Y111W-<br>Vl | 64 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT |

TABLE 9-continued

Examples and sequences of antibodies of the present invention.

| Description | SEQ ID NO | type | Sequence |
|---|---|---|---|
| | | | ACCATTAGCAGCCTGCAGCCGGAAGATATTGCGACCT<br>ATTATTGCCAGCAGGCGAACAGCTTTCCGGTGACCTT<br>TGGCGGCGGCACCAAAGTGGAAATTAAA |
| N110D-<br>S111N-<br>Vh | 65 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA<br>CCCGCGGCGGCCCGTATTATTATTATGGCATGGATGT<br>GTGGGGCCAGGGCACCACCGTGACCGTGAGCAGC |
| N110D-<br>S111N-<br>Vl | 66 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGGCGGATAACCTGCCGGTGACCTT<br>TGGCGGCGGCACCAAAGTGGAAATTAAA |
| Y109W-<br>Vh | 67 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA<br>CCCGCGGCGGCCCGTATTGGTATTATGGCATGGATGT<br>GTGGGGCCAGGGCACCACCGTGACCGTGAGCAGC |
| Y109W-<br>Vl | 68 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGGCGAACAGCTTTCCGGTGACCTT<br>TGGCGGCGGCACCAAAGTGGAAATTAAA |
| Y110S-<br>Vh | 69 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA<br>CCCGCGGCGGCCCGTATTATAGCTATGGCATGGATGT<br>GTGGGGCCAGGGCACCACCGTGACCGTGAGCAGC |
| Y110S-<br>Vl | 70 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGGCGAACAGCTTTCCGGTGACCTT<br>TGGCGGCGGCACCAAAGTGGAAATTAAA |
| O111N-<br>F112L-<br>Vh | 71 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA |

TABLE 9-continued

Examples and sequences of antibodies of the present invention.

| Description | SEQ ID NO | type | Sequence |
|---|---|---|---|
| | | | CCCGCGGCGGCCCGTATTATTATTATGGCATGGATGT GTGGGGCCAGGGCACCACCGTGACCGTGAGCAGC |
| S111N-F112L-Vl | 72 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTATC AGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGAACAACCTGCCGGTGACCTT TGGCGGCGGCACCAAAGTGGAAATTAAA |
| P107G-Vh | 73 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCAGTATGGCATGGATTGG GTGCGCCAGGCGCCGGGCAAAGGCCTGGAATGGGT GAGCGGCATTGGCCCGAGCGGCGGCAGCACCGTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCA CCCGCGGCGGCGGCTATTATTATTATGGCATGGATGT GTGGGGCCAGGGCACCACCGTGACCGTGAGCAGC |
| P107G-Vl | 74 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTATC AGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGAACAGCTTTCCGGTGACCTT TGGCGGCGGCACCAAAGTGGAAATTAAA |
| Y110R-Vh | 75 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCAGTATGGCATGGATTGG GTGCGCCAGGCGCCGGGCAAAGGCCTGGAATGGGT GAGCGGCATTGGCCCGAGCGGCGGCAGCACCGTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCA CCCGCGGCGGCCCGTATTATCGCTATGGCATGGATG TGTGGGGCCAGGGCACCACCGTGACCGTGAGCAGC |
| Y110R-Vl | 76 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTATC AGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGAACAGCTTTCCGGTGACCTT TGGCGGCGGCACCAAAGTGGAAATTAAA |
| Y110W-Vh | 77 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCAGTATGGCATGGATTGG GTGCGCCAGGCGCCGGGCAAAGGCCTGGAATGGGT GAGCGGCATTGGCCCGAGCGGCGGCAGCACCGTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCA CCCGCGGCGGCCCGTATTATTGGTATGGCATGGATGT GTGGGGCCAGGGCACCACCGTGACCGTGAGCAGC |
| Y110W-Vl | 78 | DNA | GATATTCAGATGACCCAGAGCCCGAGCAGCCTGAGC GCGAGCGTGGGCGATCGCGTGACCATTACCTGCCAG GCGAGCCAGGATATTAGCAACTATCTGAACTGGTATC AGCAGAAACCGGGCAAAGCGCCGAAACTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCAGCCGGAAGATATTGCGACCT ATTATTGCCAGCAGGCGAACAGCTTTCCGGTGACCTT TGGCGGCGGCACCAAAGTGGAAATTAAA |

TABLE 9-continued

Examples and sequences of antibodies of the present invention.

| Description | SEQ ID NO | type | Sequence |
|---|---|---|---|
| Y110N-Vh | 79 | DNA | GAAGTGCAGCTGCTGGAAAGCGGCGGCGGCCTGGTGCAGCCGGGCGGCAGCCTGCGCCTGAGCTGCGCGGCGAGCGGCTTTACCTTTAGCCAGTATGGCATGGATTGGGTGCGCCAGGCGCCGGGCAAAGGCCTGGAATGGGTGAGCGGCATTGGCCCGAGCGGCGGCAGCACCGTGTATGCGGATAGCGTGAAAGGCCGCTTTACCATTAGCCGCGATAACAGCAAAAACACCCTGTATCTGCAGATGAACAGCCTGCGCGCGGAAGATACCGCGGTGTATTATTGCACCCGCGGCGGCCCGTATTATAACTATGGCATGGATGTGTGGGGCCAGGGCACCACCGTGACCGTGAGCAGC |
| Y110N-Vl | 80 | DNA | GATATTCAGATGACCCAGAGCCCGAGCAGCCTGAGCGCGAGCGTGGGCGATCGCGTGACCATTACCTGCCAGGCGAGCCAGGATATTAGCAACTATCTGAACTGGTATCAGCAGAAACCGGGCAAAGCGCCGAAACTGCTGATTTATGATGCGAGCAACCTGGAAACCGGCGTGCCGAGCCGCTTTAGCGGCAGCGGCAGCGGCACCGATTTTACCTTTACCATTAGCAGCCTGCAGCCGGAAGATATTGCGACCTATTATTGCCAGCAGGCGAACAGCTTTCCGGTGACCTTTGGCGGCGGCACCAAAGTGGAAATTAAA |
| Y111Q-Vh | 81 | DNA | GAAGTGCAGCTGCTGGAAAGCGGCGGCGGCCTGGTGCAGCCGGGCGGCAGCCTGCGCCTGAGCTGCGCGGCGAGCGGCTTTACCTTTAGCCAGTATGGCATGGATTGGGTGCGCCAGGCGCCGGGCAAAGGCCTGGAATGGGTGAGCGGCATTGGCCCGAGCGGCGGCAGCACCGTGTATGCGGATAGCGTGAAAGGCCGCTTTACCATTAGCCGCGATAACAGCAAAAACACCCTGTATCTGCAGATGAACAGCCTGCGCGCGGAAGATACCGCGGTGTATTATTGCACCCGCGGCGGCCCGTATTATTATCAGGGCATGGATGTGTGGGGCCAGGGCACCACCGTGACCGTGAGCAGC |
| Y111Q-Vl | 82 | DNA | GATATTCAGATGACCCAGAGCCCGAGCAGCCTGAGCGCGAGCGTGGGCGATCGCGTGACCATTACCTGCCAGGCGAGCCAGGATATTAGCAACTATCTGAACTGGTATCAGCAGAAACCGGGCAAAGCGCCGAAACTGCTGATTTATGATGCGAGCAACCTGGAAACCGGCGTGCCGAGCCGCTTTAGCGGCAGCGGCAGCGGCACCGATTTTACCTTTACCATTAGCAGCCTGCAGCCGGAAGATATTGCGACCTATTATTGCCAGCAGGCGAACAGCTTTCCGGTGACCTTTGGCGGCGGCACCAAAGTGGAAATTAAA |
| Y111K-Vh | 83 | DNA | GAAGTGCAGCTGCTGGAAAGCGGCGGCGGCCTGGTGCAGCCGGGCGGCAGCCTGCGCCTGAGCTGCGCGGCGAGCGGCTTTACCTTTAGCCAGTATGGCATGGATTGGGTGCGCCAGGCGCCGGGCAAAGGCCTGGAATGGGTGAGCGGCATTGGCCCGAGCGGCGGCAGCACCGTGTATGCGGATAGCGTGAAAGGCCGCTTTACCATTAGCCGCGATAACAGCAAAAACACCCTGTATCTGCAGATGAACAGCCTGCGCGCGGAAGATACCGCGGTGTATTATTGCACCCGCGGCGGCCCGTATTATTATAAAGGCATGGATGTGTGGGGCCAGGGCACCACCGTGACCGTGAGCAGC |
| Y111K-Vl | 84 | DNA | GATATTCAGATGACCCAGAGCCCGAGCAGCCTGAGCGCGAGCGTGGGCGATCGCGTGACCATTACCTGCCAGGCGAGCCAGGATATTAGCAACTATCTGAACTGGTATCAGCAGAAACCGGGCAAAGCGCCGAAACTGCTGATTTATGATGCGAGCAACCTGGAAACCGGCGTGCCGAGCCGCTTTAGCGGCAGCGGCAGCGGCACCGATTTTACCTTTACCATTAGCAGCCTGCAGCCGGAAGATATTGCGACCTATTATTGCCAGCAGGCGAACAGCTTTCCGGTGACCTTTGGCGGCGGCACCAAAGTGGAAATTAAA |
| Y111V-Vh | 85 | DNA | GAAGTGCAGCTGCTGGAAAGCGGCGGCGGCCTGGTGCAGCCGGGCGGCAGCCTGCGCCTGAGCTGCGCGGCGAGCGGCTTTACCTTTAGCCAGTATGGCATGGATTGGGTGCGCCAGGCGCCGGGCAAAGGCCTGGAATGGGTGAGCGGCATTGGCCCGAGCGGCGGCAGCACCGTGTATGCGGATAGCGTGAAAGGCCGCTTTACCATTAGCCGCGATAACAGCAAAAACACCCTGTATCTGCAGATGAACAGCCTGCGCGCGGAAGATACCGCGGTGTATTATTGCACCCGCGGCGGCCCGTATTATTATGTGGGCATGGATGTGTGGGGCCAGGGCACCACCGTGACCGTGAGCAGC |

TABLE 9-continued

Examples and sequences of antibodies of the present invention.

| Description | SEQ ID NO | type | Sequence |
|---|---|---|---|
| Y111V-Vl | 86 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGGCGAACAGCTTTCCGGTGACCTT<br>TGGCGGCGGCACCAAAGTGGAAATTAAA |
| Y110A-Vh | 87 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCAGTATGGCATGGATTGG<br>GTGCGCCAGGCGCCGGGCAAAGGCCTGGAATGGGT<br>GAGCGGCATTGGCCCGAGCGGCGGCAGCACCGTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCA<br>CCCGCGGCGGCCCGTATTATGCGTATGGCATGGATG<br>TGTGGGGCCAGGGCACCACCGTGACCGTGAGCAGC |
| Y110A-Vl | 88 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGGCGAACAGCTTTCCGGTGACCTT<br>TGGCGGCGGCACCAAAGTGGAAATTAAA |
| M001-G16-Vh | 89 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCACCTATTGGATGACCTGG<br>GTGCGCCAGGCGCCGGGCAAAGGCCTGGAATGGGT<br>GAGCAGCATTTGGAGCAGCGGCGGCTGGACCCTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGCGCGAAGTGGGCGCGGCGGGCTTTGCGTTTGATA<br>TTTGGGGCCAGGGCACCATGGTGACCGTGAGCAGC |
| M001-G16-Vl | 90 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCAACTATCTGAACTGGTATC<br>AGCAGAAACCGGGCAAAGCGCCGAAACTGCTGATTTA<br>TGATGCGAGCAACCTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGAGCAGCAGCACCCCGCTGACCTT<br>TGGCGGCGGCACCAAAATGGAAATTAAA |
| M001-J11-Vh | 91 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCCACCTATGAAATGAACTGG<br>GTGCGCCAGGCGCCGGGCAAAGGCCTGGAATGGGT<br>GAGCTGGATTGGCCCGAGCGGCGGCTTTACCTTTTAT<br>GCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGAAAGATAAAGCGGTGGCGGGCATGGGCGAAGCGT<br>TTGATATTTGGGGCCAGGGCACCATGGTGACCGTGA<br>GCAGC |
| M001-J11-Vl | 92 | DNA | GATATTCAGATGACCCAGAGCCCGAGCAGCCTGAGC<br>GCGAGCGTGGGCGATCGCGTGACCATTACCTGCCAG<br>GCGAGCCAGGATATTAGCATTTATCTGAACTGGTATC<br>AGCAGAAACCGGGCAAAGCGCCGAAACTGCTGATTTA<br>TGATGCGAGCAACGTGGAAACCGGCGTGCCGAGCCG<br>CTTTAGCGGCAGCGGCAGCGGCACCGATTTTACCTTT<br>ACCATTAGCAGCCTGCAGCCGGAAGATATTGCGACCT<br>ATTATTGCCAGCAGTTTTATAACCTGCCGCTGACCTTT<br>GGCGGCGGCACCAAAGTGGAAATTAAA |

TABLE 9-continued

Examples and sequences of antibodies of the present invention.

| Description | SEQ ID NO | type | Sequence |
|---|---|---|---|
| M028-H17-Vh | 93 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCGATTATGAAATGGCGTGG GTGCGCCAGGCGCCGGGCAAAGGCCTGGAATGGGT GAGCAGCATTGTGCCGAGCGGCGGCTGGACCCTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCG CGACCTGGGGCGATAGCTGGGGCTTTGATTTTTGGG GCCAGGGCACCCTGGTGACCGTGAGCAGC |
| M028-H17-Vl | 94 | DNA | GATATTCAGATGACCCAGAGCCCGAGCAGCGTGAGC GCGAGCGTGGGCGATCGCGTGACCATTACCTGCCGC GCGAGCCAGGGCATTAGCAGCTGGCTGGCGTGGTAT CAGCAGCGCCCGGGCAAAGCGCCGAAACTGCTGATT TATGATGCGAGCACCCTGCAGAGCGGCGTGCCGAGC CGCTTTAGCGGCAGCGGCAGCGGCACCGATTTTACC CTGACCATTAACAGCCTGCAGCCGGAAAACTTTGCGA CCTATTATTGCCAGCAGGCGGATAGCTTTCCGATTGC GTTTGGCCAGGGCACCCGCCTGGAAATTAAA |
| M067-F04-Vh | 95 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCCGTATGATATGTATTGG GTGCGCCAGGCGCCGGGCAAAGGCCTGGAATGGGT GAGCTATATTTGGAGCAGCGGCGGCATTACCCAGTAT GCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCG CGCGCCATGCGAGCTATTATGATAGCAGCGGCCGCC CGGATGCGTTTGATATTTGGGGCCAGGGCACCATGGT GACCGTGAGCAGC |
| M067-F04-Vl | 96 | DNA | GATATTCAGATGACCCAGAGCCCGAGCAGCCTGAGC GCGAGCGTGGGCGATCGCGTGACCATTACCTGCCGC GCGAGCCAGAGCATTAGCAGCTATGTGAACTGGTATC AGCAGAAACCGGGCAAAGCGCCGAACCTGCTGATTTA TGCGGCGAGCAGCCTGGAAAGCGGCGTGCCGAGCC GCTTTAGCGGCAGCGGCAGCGGCACCGATTTTACCC TGACCATTAGCAGCCTGCAGCCGGAAGATTTTGCGAC CTATTATTGCCAGCAGAGCTATAGCACCCCGTATACC TTTGGCCAGGGCACCAAACTGGATATTAAA |
| M067-C04-Vh | 97 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCATTATAGCATGCAGTGG GTGCGCCAGGCGCCGGGCAAAGGCCTGGAATGGGT GAGCAGCATTAGCCCGAGCGGCGGCTATACCATGTAT GCGGATAGCGTGAAAGGCCGCTTTACCATTAGCCGC GATAACAGCAAAAACACCCTGTATCTGCAGATGAACA GCCTGCGCGCGGAAGATACCGCGATGTATTATTGCG CGCGCGAAAAAGCGAGCGATCTGAGCGGCACCTATA GCGAAGCGCTGGATTATTGGGGCCAGGGCACCCTGG TGACCGTGAGCAGC |
| M067-C04-Vl | 98 | DNA | GATATTCAGATGACCCAGAGCCCGAGCAGCCTGAGC GCGAGCGTGGGCGATCGCGTGACCATTACCTGCCAG GCGAGCCAGGATATTGATTATTATCTGAACTGGTATCA GCAGCAGCCGGGCAAAGCGCCGCAGCTGCTGATTTA TGATGCGAGCAACCTGGAAACCGGCGTGCCGAGCCG CTTTAGCGGCAGCGGCAGCGGCACCGATTTTACCTTT ACCATTAGCAGCCTGCATCCGGAAGATTTTGCGACCT ATTATTGCCAGCAGTATCATACCCTGCCGCCGCTGAC CTTTGGCGGCGGCACCAAAGTGGATATTAAA |
| M071-F17-Vh | 99 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCCCGTATTGGATGCATTGG GTGCGCCAGGCGCCGGGCAAAGGCCTGGAATGGGT GAGCAGCATTTATAGCAGCGGCGGCTGGACCGATTAT GCGGATAGCGTGAAAGGCCGCTTTACCATTAGCCGC GATAACAGCAAAAACACCCTGTATCTGCAGATGAACA |

TABLE 9-continued

Examples and sequences of antibodies of the present invention.

| Description | SEQ ID NO | type | Sequence |
|---|---|---|---|
| | | | GCCTGCGCGCGGAAGATACCGCGGTGTATTATTGCG<br>CGCGCGAAGGCGTGGCGGGCACCAACGATGCGTTTG<br>ATATTTGGGGCCAGGGCACCATGGTGACCGTGAGCA<br>GC |
| M071-<br>F17-<br>Vl | 100 | DNA | GATATTCAGATGACCCAGAGCCCGCTGAGCCTGAGC<br>GCGAGCGTGGGCGATCGCGTGACCATTACCTGCCGC<br>GCGAGCCAGAGCATTAGCAGCTATCTGAACTGGTATC<br>AGCAGAAACCGGGCAAAGCGCCGAAACTGCTGATTTA<br>TGCGGCGAGCAGCCTGCAGAGCGGCGTGCCGAGCC<br>GCTTTAGCGGCAGCGGCAGCGGCACCGATTTTACCC<br>TGACCATTAGCAGCCTGCAGCCGGAAGATTTTGCGAC<br>CTATTATTGCCAGCAGAGCTATAGCACCCCGCCGTGG<br>ACCTTTGGCCAGGGCACCAAAGTGGAAATTAAA |
| H17-<br>R47K-<br>Vh | 101 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCGATTATGAAATGGCGTGG<br>GTGCGCCAGGCGCCGGGCAAAGGCCTGGAATGGGT<br>GAGCAGCATTGTGCCGAGCGGCGGCTGGACCCTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGACCTGGGGCGATAGCTGGGGCTTTGATTTTTGGG<br>GCCAGGGCACCCTGGTGACCGTGAGCAGC |
| H17-<br>R47K-<br>Vl | 102 | DNA | GATATTCAGATGACCCAGAGCCCGAGCAGCGTGAGC<br>GCGAGCGTGGGCGATCGCGTGACCATTACCTGCCGC<br>GCGAGCCAGGGCATTAGCAGCTGGCTGGCGTGGTAT<br>CAGCAGAAACCGGGCAAAGCGCCGAAACTGCTGATTT<br>ATGATGCGAGCACCCTGCAGAGCGGCGTGCCGAGCC<br>GCTTTAGCGGCAGCGGCAGCGGCACCGATTTTACCC<br>TGACCATTAACAGCCTGCAGCCGGAAAACTTTGCGAC<br>CTATTATTGCCAGCAGGCGGATAGCTTTCCGATTGCG<br>TTTGGCCAGGGCACCCGCCTGGAAATTAAA |
| H17-<br>T69S-<br>Vh | 103 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCGATTATGAAATGGCGTGG<br>GTGCGCCAGGCGCCGGGCAAAGGCCTGGAATGGGT<br>GAGCAGCATTGTGCCGAGCGGCGGCTGGACCCTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGACCTGGGGCGATAGCTGGGGCTTTGATTTTTGGG<br>GCCAGGGCACCCTGGTGACCGTGAGCAGC |
| H17-<br>T69S-<br>Vl | 104 | DNA | GATATTCAGATGACCCAGAGCCCGAGCAGCGTGAGC<br>GCGAGCGTGGGCGATCGCGTGACCATTACCTGCCGC<br>GCGAGCCAGGGCATTAGCAGCTGGCTGGCGTGGTAT<br>CAGCAGCGCCCGGGCAAAGCGCCGAAACTGCTGATT<br>TATGATGCGAGCAGCCTGCAGAGCGGCGTGCCGAGC<br>CGCTTTAGCGGCAGCGGCAGCGGCACCGATTTTACC<br>CTGACCATTAACAGCCTGCAGCCGGAAAACTTTGCGA<br>CCTATTATTGCCAGCAGGCGGATAGCTTTCCGATTGC<br>GTTTGGCCAGGGCACCCGCCTGGAAATTAAA |
| H17-<br>N100D-<br>Vh | 105 | DNA | GAAGTGCAGCTGCTGGAAAGCGGCGGCGGCCTGGTG<br>CAGCCGGGCGGCAGCCTGCGCCTGAGCTGCGCGGC<br>GAGCGGCTTTACCTTTAGCGATTATGAAATGGCGTGG<br>GTGCGCCAGGCGCCGGGCAAAGGCCTGGAATGGGT<br>GAGCAGCATTGTGCCGAGCGGCGGCTGGACCCTGTA<br>TGCGGATAGCGTGAAAGGCCGCTTTACCATTAGCCGC<br>GATAACAGCAAAAACACCCTGTATCTGCAGATGAACA<br>GCCTGCGCGCGGAAGATACCGCGGTGTATTATTGCG<br>CGACCTGGGGCGATAGCTGGGGCTTTGATTTTTGGG<br>GCCAGGGCACCCTGGTGACCGTGAGCAGC |
| H17-<br>N100D-<br>Vl | 106 | DNA | GATATTCAGATGACCCAGAGCCCGAGCAGCGTGAGC<br>GCGAGCGTGGGCGATCGCGTGACCATTACCTGCCGC<br>GCGAGCCAGGGCATTAGCAGCTGGCTGGCGTGGTAT<br>CAGCAGCGCCCGGGCAAAGCGCCGAAACTGCTGATT<br>TATGATGCGAGCACCCTGCAGAGCGGCGTGCCGAGC<br>CGCTTTAGCGGCAGCGGCAGCGGCACCGATTTTACC<br>CTGACCATTAACAGCCTGCAGCCGGAAGATTTTGCGA |

TABLE 9-continued

Examples and sequences of antibodies of the present invention.

| Description | SEQ ID NO | type | Sequence |
|---|---|---|---|
| | | | CCTATTATTGCCAGCAGGCGGATAGCTTTCCGATTGC GTTTGGCCAGGGCACCCGCCTGGAAATTAAA |
| H17-A115T-Vh | 107 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCGATTATGAAATGGCGTGG GTGCGCCAGGCGCCGGGCAAAGGCCTGGAATGGGT GAGCAGCATTGTGCCGAGCGGCGGCTGGACCCTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCG CGACCTGGGGCGATAGCTGGGCTTTGATTTTTGGG GCCAGGGCACCCTGGTGACCGTGAGCAGC |
| H17-A115T-Vl | 108 | DNA | GATATTCAGATGACCCAGAGCCCGAGCAGCGTGAGC GCGAGCGTGGGCGATCGCGTGACCATTACCTGCCGC GCGAGCCAGGGCATTAGCAGCTGGCTGGCGTGGTAT CAGCAGCGCCCGGGCAAAGCGCCGAAACTGCTGATT TATGATGCGAGCACCCTGCAGAGCGGCGTGCCGAGC CGCTTTAGCGGCAGCGGCAGCGGCACCGATTTTACC CTGACCATTAACAGCCTGCAGCCGGAAAACTTTGCGA CCTATTATTGCCAGCAGGCGGATAGCTTTCCGATTAC CTTTGGCCAGGGCACCCGCCTGGAAATTAAA |
| H17-R47K-Vh | 109 | DNA | GAAGTGCAGCTGCTGGAAAGCGGCGGCGGCCTGGTG CAGCCGGGCGGCAGCCTGCGCCTGAGCTGCGCGGC GAGCGGCTTTACCTTTAGCGATTATGAAATGGCGTGG GTGCGCCAGGCGCCGGGCAAAGGCCTGGAATGGGT GAGCAGCATTGTGCCGAGCGGCGGCTGGACCCTGTA TGCGGATAGCGTGAAAGGCCGCTTTACCATTAGCCGC GATAACAGCAAAAACACCCTGTATCTGCAGATGAACA GCCTGCGCGCGGAAGATACCGCGGTGTATTATTGCG CGACCTGGGGCGATAGCTGGGCTTTGATTTTTGGG GCCAGGGCACCCTGGTGACCGTGAGCAGC |
| H17-R47K-Vl | 110 | DNA | GATATTCAGATGACCCAGAGCCCGAGCAGCGTGAGC GCGAGCGTGGGCGATCGCGTGACCATTACCTGCCGC GCGAGCCAGGGCATTAGCAGCTGGCTGGCGTGGTAT CAGCAGAAACCGGGCAAAGCGCCGAAACTGCTGATTT ATGATGCGAGCACCCTGCAGAGCGGCGTGCCGAGCC GCTTTAGCGGCAGCGGCAGCGGCACCGATTTTACCC TGACCATTAACAGCCTGCAGCCGGAAGATTTTGCGAC CTATTATTGCCAGCAGGCGGATAGCTTTCCGATTGCG TTTGGCCAGGGCACCCGCCTGGAAATTAAA |
| M009-G02-Vh | 111 | PRT | EVQLLESGGGLVQPGGSLRLSCAASGFTFSRYIMHWVR QAPGKGLEWVSSISPSGGLTSYADSVKGRFTISRDNSK NTLYLQMNSLRAEDTAVYYCAREFENAYHYYYGMDV WGQGTTVTVSS |
| M009-G02-Vl | 112 | PRT | DIQMTQSPSSLSASVGDRVTITCRASGDIGNALGWYQQ KPGKAPRLLISDASTLQSGVPLRFSGSGSGTEFTLTISSL QPEDFATYYCLQGYNYPRTFGQGTKLEIR |
| G16-Vh | 113 | PRT | EVQLLESGGGLVQPGGSLRLSCAASGFTFSWYPMQWV RQAPGKGLEWVSGISSSGGGTYYADSVKGRFTISRDNS KNTLYLQMNSLRAEDTAVYYCARDWGYSNYVMDLGLD YWGQGTLVTVSS |
| G16-Vl | 114 | PRT | DIQMTQSPATLSLSAGERATLSCRASQTVSSSLAWYQH KPGQAPRLLIYETSNRATGIPARFSGSGSGTDFTLTISSL EPEDFAVYYCQHRSNWPPTFGPGTKVDIK |
| G11-Vh | 115 | PRT | EVQLLESGGGLVQPGGSLRLSCAASGFTFSTYSMGWV RQAPGKGLEWVSSISPSGGDTDYADSVKGRFTISRDNS KNTLYLQMNSLRAEDTAVYYCARERTMVRDPRYYGMD VWGQGTTVTVSS |
| G11-Vl | 116 | PRT | DIQMTQSPATLSLSPGERATLSCRASQSVSSYLAWYQQ RLGQSPRLLIYDASSRATGIPARFSGSGSGTDFTLTISSL QPEDFATYYCQQSYSNLVTFGQGTRLEIK |

TABLE 9-continued

Examples and sequences of antibodies of the present invention.

| Description | SEQ ID NO | type | Sequence |
|---|---|---|---|
| M014-G02-Vh | 117 | PRT | EVQLLESGGGLVQPGGSLRLSCAASGFTFSLYYMKWVR QAPGKGLEWVSSISPSGGFTSYADSVKGRFTISRDNSK NTLYLQMNSLRAEDTAVYYCAREFENAYHYYYGMDV WGQGTTVTVSS |
| M014-G02-Vl | 118 | PRT | DIQMTQSPSSVSASVGDRVTITCRASQDINIWLAWYQQK PGKAPKLLISAASTVQSGVPSRFSGSGSGTDFTLTINTLQ PDDFATYYCQQAASFPLTFGGGTKVEMK |
| M013-J04-Vh | 11 9 | PRT | EVQLLESGGGLVQPGGSLRLSCAASGFTFSTYSMGWV RQAPGKGLEWVSSISPSGGDTDYADSVKGRFTISRDNS KNTLYLQMNSLRAEDTAVYYCARERTMVRDPRYYGMD VWGQGTTVTVSS |
| M013-J04-Vl | 120 | PRT | DIQMTQSPATLSLSPGERATLSCRASQSVSSYLAWYQQ RLGQSPRLLIYDASSRATGIPARFSGSGSGTDFTLTISSL QPKDFATYYCQQSYSNLVTFGQGTRLEIK |
| A10-Vh | 121 | PRT | EVQLLESGGGLVQPGGSLRLSCAASGFTFSWYPMQWV RQAPGKGLEWVSGISSSGGGTYYADSVKGRFTISRDNS KNTLYLQMNSLRAEDTAVYYCARDWGYSNYVMDLGLD YWGQGTLVTVSS |
| A10-Vl | 122 | PRT | DIQMTQSPATLSLSAGERATLSCRASQTVSSSLAWYQH KPGQAPRLLIYETSNRATGIPARFSGSGSGTDFTLTISSL EPEDFAVYYCQHRSNWPPTFGPGTKVDIK |
| M10-Vh | 123 | PRT | EVQLLESGGGLVQPGGSLRLSCAASGFTFSWYPMQWV RQAPGKGLEWVSGISSSGGGTYYADSVKGRFTISRDNS KNTLYLQMNSLRAEDTAVYYCARDWGYSNYVMDLGLD YWGQGTLVTVSS |
| M10-Vl | 124 | PRT | DIQMTQSPATLSLSAGERATLSCRASQTVSSSLAWYQH KPGQAPRLLIYETSNRATGIPARFSGSGSGTDFTLTISSL EPEDFAVYYCQHRSNWPPTFGPGTKVDIK |
| H15-Vh | 125 | PRT | EVQLLESGGGLVQPGGSLRLSCAASGFTFSTYSMGWV RQAPGKGLEWVSSISPSGGDTDYADSVKGRFTISRDNS KNTLYLQMNSLRAEDTAVYYCARERTMVRDPRYYGMD VWGQGTTVTVSS |
| H15-Vl | 126 | PRT | DIQMTQSPATLSLSPGERATLSCRASQSVSSYLAWYQQ RLGQSPRLLIYDASSRATGIPARFSGSGSGTDFTLTISSL QPEDFATYYCQQSYSNLVTFGQGTRLEIK |
| F11-Vh | 127 | PRT | EVQLLESGGGLVQPGGSLRLSCAASGFTFSNYMMTVVV RQAPGKGLEWVSGIYPSGGFTQYADSVKGRFTISRDNS KNTLYLQMNSLRAEDTATYYCARDASDVWLRFRGGGAF DIWGQGTMVTVSS |
| F11-Vl | 128 | PRT | DIQMTQSPTSLSASVGDRVAITCRASQSIDTYLNWYQQK PGKAPKLLIYDASNLETGVPSRFSGSGSGTDFTFTISSLQ PEDIATYYCQQFDDLPLTFGPGTRVDIK |
| K12-Vh | 129 | PRT | EVQLLESGGGLVQPGGSLRLSCAASGFTFSRYIMHWVR QAPGKGLEWVSSISPSGGLTSYADSVKGRFTISRDNSK NTLYLQMNSLRAEDTAVYYCAREFENAYHYYYGMDV WGQGTTVTVSS |
| K12-Vl | 130 | PRT | DIQMTQSPSSLSASVGDRVTITCRASGDIGNALGWYQQ KPGKAPRLLISDASTLQSGVPLRFSGSGSGTEFTLTISSL QPEDFATYYCLQGYNYPRTFGQGTKLEIR |
| O15-Vh | 131 | PRT | EVQLLESGGGLVQPGGSLRLSCAASGFTFSRYIMHWVR QAPGKGLEWVSSISPSGGLTSYADSVKGRFTISRDNSK NTLYLQMNSLRAEDTAVYYCAREFENAYHYYYGMDV WGQGTTVTVSS |
| O15-Vl | 132 | PRT | DIQMTQSPSSLSASVGDRVTITCRASGDIGNALGWYQQ KPGKAPRLLISDASTLQSGVPLRFSGSGSGTEFTLTISSL QPEDFATYYCLQGYNYPRTFGQGTKLEIR |

TABLE 9-continued

Examples and sequences of antibodies of the present invention.

| Description | SEQ ID NO | type | Sequence |
|---|---|---|---|
| A08-Vh | 133 | PRT | EVQLLESGGGLVQPGGSLRLSCAASGFTFSEYGMIWVR QAPGKGLEWVSFISPSGGTTFYADSVKGRFTISRDNFKN TLYLQMNSLRAEDTAVYYCARGGGNWNHRRALNDAFDI WGQGTMVTVSS |
| A08-Vl | 134 | PRT | DIQMTQSPSSLSASVGDRITITCRASQAIRDDFGWYQQK PGKAPKLLIYAASSLQSGVPSRFSGSGSGTDFTLTISSLQ PEDFATYYCQQSYSTPLTFGGGTKVEIK |
| E12-Vh | 135 | PRT | EVQLLESGGGLVQPGGSLRLSCAASGFTFSTYSMGWV RQAPGKGLEWVSSISPSGGDTYADSVKGRFTISRDNS KNTLYLQMNSLRAEDTAVYYCARERTMVRDPRYYGMD VWGQGTTVTVSS |
| E12-Vl | 136 | PRT | DIQMTQSPATLSLSPGERATLSCRASQSVSSYLAWYQQ RLGQSPRLLIYDASSRATGIPARFSGSGSGTDFTLTISSL QPEDFATYYCQQSYSNLVTFGQGTRLEIK |
| Y111W-Vh | 137 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYWGMDVWG QGTTVTVSS |
| Y111W-Vl | 138 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| N110D-S111N-Vh | 139 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYYGMDVWGQ GTTVTVSS |
| N110D-S111N-Vl | 140 | PRT | DIQMTQSPSSLSASVGDRVTITCQASQDISNYLNWYQQK PGKAPKLLIYDASNLETGVPSRFSGSGSGTDFTFTISSLQ PEDIATYYCQQADNLPVTFGGGTKVEIK |
| Y109W-Vh | 141 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYWYYGMDVWG QGTTVTVSS |
| Y109W-Vl | 142 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y110S-Vh | 143 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYSYGMDVWGQ GTTVTVSS |
| Y110S-Vl | 144 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| S111N-F112L-Vh | 145 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYYGMDVWGQ GTTVTVSS |
| S111N-F112L-Vl | 146 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANNLPVTFGGGTKVEIK |
| P107G-Vh | 147 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGGYYYYGMDVWGQ GTTVTVSS |
| P107G-Vl | 148 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |

TABLE 9-continued

Examples and sequences of antibodies of the present invention.

| Description | SEQ ID NO | type | Sequence |
|---|---|---|---|
| Y110R-Vh | 149 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYRYGMDVWGQ GTTVTVSS |
| Y110R-Vl | 150 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y110W-Vh | 151 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYWYGMDVWG QGTTVTVSS |
| Y110W-Vl | 152 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y110N-Vh | 153 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYNYGMDVWGQ GTTVTVSS |
| Y110N-Vl | 154 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y111Q-Vh | 155 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYQGMDVWGQ GTTVTVSS |
| Y111Q-Vl | 156 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y111K-Vh | 157 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYKGMDVWGQ GTTVTVSS |
| Y111K-Vl | 158 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y111V-Vh | 159 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYYVGMDVWGQ GTTVTVSS |
| Y111V-Vl | 160 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| Y110A-Vh | 161 | PRT | EVQLLESGGGLVQPGGSLRLSCAASGFTFSQYGMDWV RQAPGKGLEWVSGIGPSGGSTVYADSVKGRFTISRDNS KNTLYLQMNSLRAEDTAVYYCTRGGPYYAYGMDVWGQ GTTVTVSS |
| Y110A-Vl | 162 | PRT | DIQMTQSPSSLSASVGDRVTITCQASQDISNYLNWYQQK PGKAPKLLIYDASNLETGVPSRFSGSGSGTDFTFTISSLQ PEDIATYYCQQANSFPVTFGGGTKVEIK |
| M001-G16-Vh | 163 | PRT | EVQLLESGGGLVQPGGSLRLSCAASGFTFSTYWMTWV RQAPGKGLEWVSSIWSSGGWTLYADSVKGRFTISRDNS KNTLYLQMNSLRAEDTAVYYCAREVGAAGFAFDIWGQG TMVTVSS |
| M001-G16-Vl | 164 | PRT | DIQMTQSPSSLSASVGDRVTITCQASQDISNYLNWYQQK PGKAPKLLIYDASNLETGVPSRFSGSGSGTDFTFTISSLQ PEDIATYYCQQSSSTPLTFGGGTKMEIK |

TABLE 9-continued

Examples and sequences of antibodies of the present invention.

| Description | SEQ ID NO | type | Sequence |
|---|---|---|---|
| M001-J11-Vh | 165 | PRT | EVQLLESGGGLVQPGGSLRLSCAASGFTFSTYEMNWV RQAPGKGLEWVSWIGPSGGFTFYADSVKGRFTISRDNS KNTLYLQMNSLRAEDTAVYYCAKDKAVAGMGEAFDIWG QGTMVTVSS |
| M001-J11-Vl | 166 | PRT | DIQMTQSPSSLSASVGDRVTITCQASQDISIYLNWYQQK PGKAPKLLIYDASNVETGVPSRFSGSGSGTDFTFTISSLQ PEDIATYYCQQFYNLPLTFGGGTKVEIK |
| M028-H17-Vh | 167 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| M028-H17-Vl | 168 | PRT | DIQMTQSPSSVSASVGDRVTITCRASQGISSWLAWYQQ RPGKAPKLLIYDASTLQSGVPSRFSGSGSGTDFTLTINSL QPENFATYYCQQADSFPIAFGQGTRLEIK |
| M067-F04-Vh | 169 | PRT | EVQLLESGGGLVQPGGSLRLSCAASGFTFSPYDMYWV RQAPGKGLEWVSYIWSSGGITQYADSVKGRFTISRDNS KNTLYLQMNSLRAEDTAVYYCARHASYYDSSGRPDAFD IWGQGTMVTVSS |
| M067-F04-Vl | 170 | PRT | DIQMTQSPSSLSASVGDRVTITCRASQSISSYVNWYQQK PGKAPNLLIYAASSLESGVPSRFSGSGSGTDFTLTISSLQ PEDFATYYCQQSYSTPYTFGQGTKLDIK |
| M067-C04-Vh | 171 | PRT | EVQLLESGGGLVQPGGSLRLSCAASGFTFSHYSMQWV RQAPGKGLEWVSSISPSGGYTMYADSVKGRFTISRDNS KNTLYLQMNSLRAEDTAMYYCAREKASDLSGTYSEALD YWGQGTLVTVSS |
| M067-C04-Vl | 172 | PRT | DIQMTQSPSSLSASVGDRVTITCQASQDIDYYLNWYQQ QPGKAPQLLIYDASNLETGVPSRFSGSGSGTDFTFTISSL HPEDFATYYCQQYHTLPPLTFGGGTKVDIK |
| M071-F17-Vh | 173 | PRT | EVQLLESGGGLVQPGGSLRLSCAASGFTFSPYWMHWV RQAPGKGLEWVSSIYSSGGWTDYADSVKGRFTISRDNS KNTLYLQMNSLRAEDTAVYYCAREGVAGTNDAFDIWGQ GTMVTVSS |
| M071-F17-Vl | 174 | PRT | DIQMTQSPLSLSASVGDRVTITCRASQSISSYLNWYQQK PGKAPKLLIYAASSLQSGVPSRFSGSGSGTDFTLTISSLQ PEDFATYYCQQSYSTPPWTFGQGTKVEI |
| H17-R47K-Vh | 175 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17-R47K-Vl | 176 | PRT | DIQMTQSPSSVSASVGDRVTITCRASQGISSWLAWYQQ KPGKAPKLLIYDASTLQSGVPSRFSGSGSGTDFTLTINSL QPENFATYYCQQADSFPIAFGQGTRLEIK |
| H17-T69S-Vh | 177 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17-T69S-Vl | 178 | PRT | DIQMTQSPSSVSASVGDRVTITCRASQGISSWLAWYQQ RPGKAPKLLIYDASSLQSGVPSRFSGSGSGTDFTLTINSL QPENFATYYCQQADSFPIAFGQGTRLEIK |
| H17-N100D-Vh | 179 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17-N100D-Vl | 180 | PRT | DIQMTQSPSSVSASVGDRVTITCRASQGISSWLAWYQQ RPGKAPKLLIYDASTLQSGVPSRFSGSGSGTDFTLTINSL QPEDFATYYCQQADSFPIAFGQGTRLEIK |

TABLE 9-continued

Examples and sequences of antibodies of the present invention.

| Description | SEQ ID NO | type | Sequence |
|---|---|---|---|
| H17-A115T-Vh | 181 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17-A115T-Vl | 182 | PRT | DIQMTQSPSSVSASVGDRVTITCRASQGISSWLAWYQQ RPGKAPKLLIYDASTLQSGVPSRFSGSGSGTDFTLTINSL QPENFATYYCQQADSFPITFGQGTRLEIK |
| H17-R47K-Vh | 183 | PRT | EVQLLESGGGLVQPGGSLRLSCAASGFTFSDYEMAWV RQAPGKGLEWVSSIVPSGGWTLYADSVKGRFTISRDNS KNTLYLQMNSLRAEDTAVYYCATWGDSWGFDFWGQGT LVTVSS |
| H17-R47K-Vl | 184 | PRT | DIQMTQSPSSVSASVGDRVTITCRASQGISSWLAWYQQ KPGKAPKLLIYDASTLQSGVPSRFSGSGSGTDFTLTINSL QPEDFATYYCQQADSFPIAFGQGTRLEIK |

EXAMPLE 4

Determination of the Anti-Aggregatory Activity of the FXIa Antibody

For the measurement of platelet activation under flow conditions, glass slides (Menzel-Glaser SUPERFROST 76 mm×26 mm; Gerhard Menzel GmbH, Braunschweig, Germany) were coated with collagen (150 µg/ml) overnight at 4° C., followed by blocking with BSA (5 mg/ml) prior to assembly into a flow system on the stage of a Zeiss Axiovert 135 microscope (Carl Zeiss, Göttingen, Germany). Citrated whole blood was incubated with GPRP (3 mM final) and vehicle or FXI antibodies for 10 min at 37° C. After the addition of $CaCl_2$ (5 mM), blood was immediately perfused over the collagen-coated slide at the initial shear rate of 1000 $s^{-1}$ for 5 min. After the perfusion of whole blood as described above, post-chamber whole blood was collected into sodium citrate (1:10 vol/vol) at each 1 min. Pre-chamber blood was also sampled and treated with or without TRAP6 as positive control (10 µg/ml) for 5 min.

Pre- and post-chamber blood samples were diluted in Cell Wash (BD Biosciences, Heidelberg, Germany) and incubated with antibodies for 20 min at 4° C. Antibody reaction was stopped by adding ice cold-Cell Wash and all samples were kept on ice until measurement. 10000 single platelets were determined with the positivity of the FITC-conjugated platelet marker (CD41a or CD61a) and the characteristic light scatter patterns by flow cytometry (FACSCalibur; BD Biosciences, Heidelberg, Germany). For CD62P expression, single platelets were gated to a separate scatter plot with a PE-CD62P fluorescence threshold which was verified with unlabeled control samples. The platelet population above the threshold was considered activated and quantified. Platelet microaggregates were defined with the arbitrary thresholds for Forward Scatter (FSC) and FITC-fluorescence.

EXAMPLE 5

$FeCl_2$ Induced Thrombosis and Ear Bleeding Time in Rabbits

The antithrombotic activity of 076D-M007-H04, 076D-M007-H04-CDRL3-N110D and 076D-M028-H17 was determined in an arterial thrombosis model. 15 minutes after an i.v. bolus administration of 076D-M007-H04 (0.5 mg/kg, 1 mg/kg, 2 mg/kg), 076D-M007-H04-CDRL3-N110D (0.1 mg/kg, 0.3 mg/kg, 1 mg/kg) or 076D-M028-H17 (0.075 mg/kg, 0.15 mg/kg, 0.3 mg/kg) thrombosis was induced by chemical damage of a carotid artery by ferric chloride in rabbits. Male rabbits (Crl:KBL (NZW)BR, Charles River) were anaesthetized with a mixture of xylazine and ketamine (Rompun, Bayer 5 mg/kg and Ketavet Pharmacia & Upjohn GmbH, 40 mg/kg body weight) given by i.m. injection. Supplemental anesthesia was administered by infusion of the anesthetic mixture in the marginal vein of the right ear. After exposure of the right common carotid artery vascular damage was produced by placing a piece of blotting paper (10 mm×10 mm) on a strip of Parafilm® (25 mm×12 mm) under the right common carotid artery in a way that the blood flow was not affected. The blotting paper was saturated with 100 µl $FeCl_2$ (Iron(II) chloride tetrahydrate), 13% in A. dest, Sigma). After 5 minutes the filter paper was removed, and the vessel was rinsed twice with 0.9% NaCl. 30 minutes after the injury the carotid artery was removed, the thrombus withdrawn and weighed immediately. 5-7 animals were used for each group. The ear bleeding time was determined 2 minutes after the $FeCl_2$-injury. The left ear was shaved and a standardized incision (3 mm long) was made with a surgical blade (number 10-150-10, Martin, Tuttlingen, Germany) parallel to the long axis of the ear. Care was taken to avoid damage of visible blood vessels. The incision sites were blotted at 30 sec intervals with filter paper, carefully avoiding contact with the wound. The bleeding time was determined by measuring the time from the incision until blood no longer stained the filter paper.

EXAMPLE 6

Figure 14A:
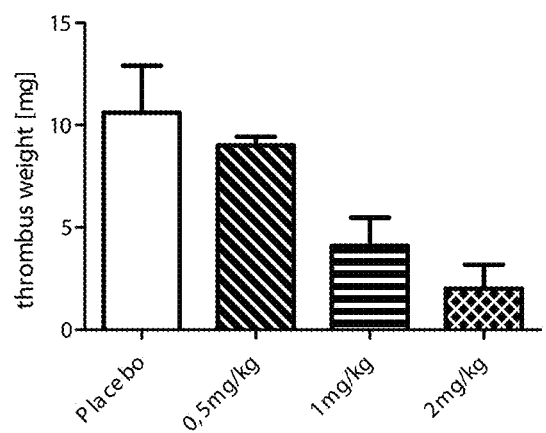
FIGS. 14A-14B: In vivo effect of 076D-M007-H04 on ferric chloride induced thrombosis (FIG. 14A) and on ear bleeding time (FIG. 14B). It could be demonstrated that 076D-M007-H04 dose-dependently reduces the thrombus weight without increasing the ear bleeding time.
Figure 14B:
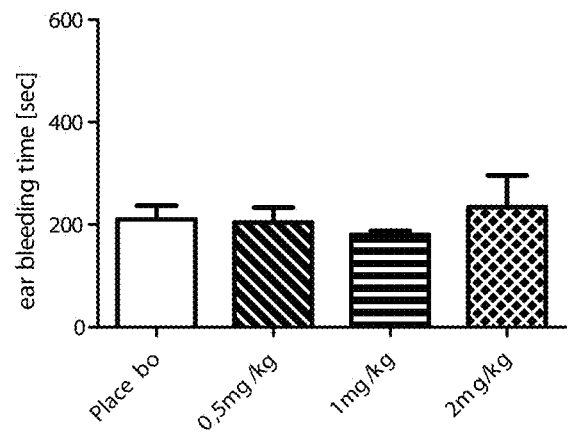
Figure 15A:
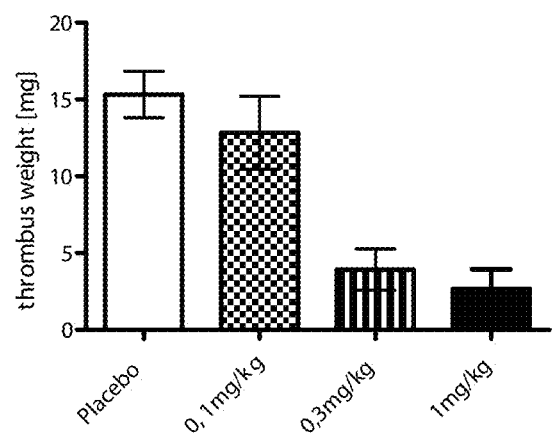
FIGS. 15A-15B: In vivo effect of 076D-M007-H04-CDRL3-N110D on ferric chloride induced thrombosis (FIG. 15A) and on ear bleeding time (FIG. 15B) (described in Example 6). It could be demonstrated that 076D-M007-H04-CDRL3-N110D dose-dependently reduces the thrombus weight without increasing the ear bleeding time.
Figure 15B:
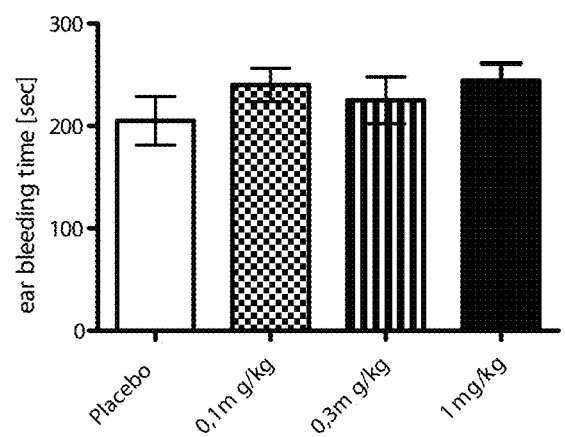
Figure 16A:
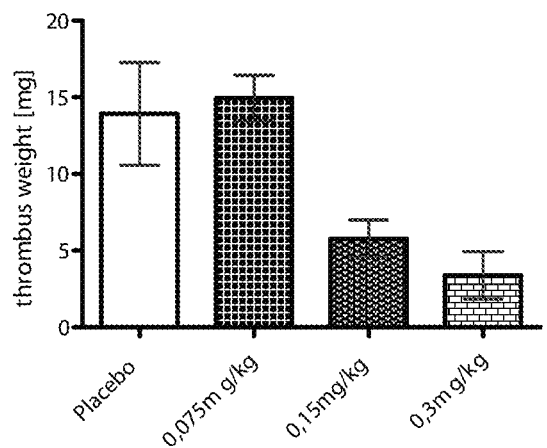
FIGS. 16A-16B: In vivo effect shows the effect of 076D-M028-H17 on ferric chloride induced thrombosis (FIG. 16A) and on ear bleeding time (FIG. 16B) (described in Example 6). It could be demonstrated that 076D-M028-H17 dose-dependently reduces the thrombus weight without increasing the ear bleeding time.
Figure 16B:
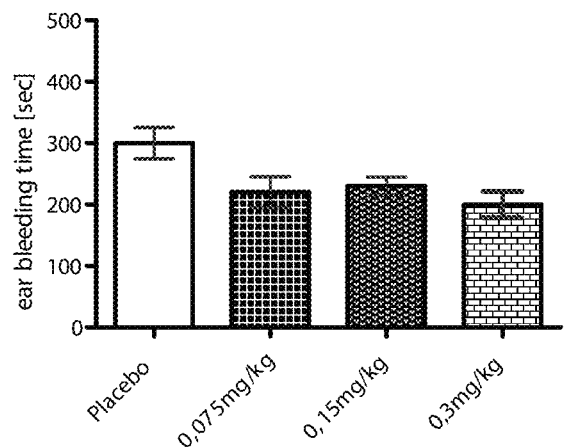

Determination of the $FeCl_2$ Induced Thrombosis and Ear Bleeding Time in Rabbits 076D-M007-H04 dose-dependently reduces the thrombus weight and does not prolong the ear bleeding time as shown in FIGS. 14A-14B. FIGS. 15A-15B demonstrate the antithrombotic effect of 076D-M007-H04-CDRL3-N110D without an increase in ear bleeding time. In FIGS. 16A-16B the antithrombotic effect and no bleeding time prolongation of 076D-M028-H17 are shown.

EXAMPLE 7

Complex Formation, Crystallization and X-Ray Structure Determination of Fab 076D-M007-H04:FXIa Complex Complex Formation and Crystallization FXIa C500S (amino acids 388-625) was purchased by Proteros Biostructures. Purified Fab 076D-M007-H04 was mixed in a 1:1 ratio with FXIa C500S. To allow complex formation the solution was stored for 18 hours on ice. The complex solution was loaded on a Superdex 200 HR 16/60 column and was further concentrated to a final concentration of 20 mg/ml in 20 mM Tris/HCl at pH 7.5 and 75 mM NaCl. Crystals of the protein complex comprising Fab 076D-M007-H04 and FXIa C500S were grown at 20° C. using the sitting-drop method and crystallized by mixing equal volumes of protein complex solution and well solution (100 mM TRIS pH 8.25, 0.05% PEG20000, and 2.4M $NH_4SO_4$ as precipitant. A rosette like crystal appeared after approximately five days.

Data Collection and Processing

Crystal was flash-frozen in liquid nitrogen without use of cryo-buffer. Data of crystal was collected at beamline BL14.1, BESSY synchrotron (Berlin) on a MAR CCD detector. Data was indexed and integrated with XDS (Kabsch, W. (2010) Acta Cryst D66:125-132), prepared for scaling with POINTLESS, and scaled with SCALA (P. R. Evans, (2005) Acta Cryst D62:72-82). The crystal diffracted up to 2.7 Å and possesses orthorhombic space group P2(1)22(1) with cell constant a=61.9, b=70.7, c=185.9 and one Fab 076D-M007-H04:FXIa C500S complex in the asymmetric unit.

Structure Determination and Refinement

The complex-structure of FXIa and the monoclonal antibody Fab 076D-M007-H04 was solved by molecular replacement in different steps. First the H-chain was located using BALBES (F. Long, A. Vagin, P. Young and G. N. Murshudov (2008) Acta Cryst D64:125-132), with pdb code 3GJE as search model. Then FXIa C500S was added using program MolRep with an internal FXIa crystal structure as search model. Initial refinement with REFMAC5.5 (G. N. Murshudov et al. (1997) Acta Cryst D53:240-255) results in R1=39.4% and Rfree=44.1%. Finally, the H-chain was located using the L-chain of pdb entry 3IDX as search model and fixed coordiantes of the initially refined H-chain and FXIa C500S solution. Iterative rounds of model building with COOT (P. Emsley et al. (2010) Acta Cryst D66: 486-501) and maximum likelihood refinement using REFMAC5.5 completed the model. Data set and refinement statistics are summarized in Table 10.

TABLE 10

Data set and refinement statistics for Fab 076D-M007-H04:FXIa complex.

| | |
|---|---|
| Wavelength | 0.91823 Å |
| Resolution (highest shell) | 33.03-2.70 (2.84-2.70) Å |
| Reflections (observed/unique) | 110602/16132 |
| Completeness[a] | 99.8% (99.15%) |
| I/s[a] | 5.61 (1.79) |
| $R_{merge}$[a, b] | 0.12 (0.43) |
| Space group | P2(1)22(1) |
| Unit cell parameters | |
| a | 61.94 Å |
| b | 87.68 Å |
| c | 185.89 Å |

TABLE 10-continued

Data set and refinement statistics for Fab 076D-M007-H04:FXIa complex.

| | |
|---|---|
| $R_{cryst}$[c] | 0.228 |
| $R_{free}$[d] | 0.305 |
| Wilson temperature factor | 51.7 Å² |
| RMSD bond length[e] | 0.022 Å |
| RMSD bond angles | 1.95° |
| Protein atoms | 5042 |
| Water and solvent molecules | 34 |

[a]The values in parentheses are for the high resolution shell.
[b]$R_{merge} = \Sigma hkl\ |I_{hkl} - <I_{hkl}>|/\Sigma hkl\ <I_{hkl}>$ where $I_{hkl}$ is the intensity of reflection hkl and $<I_{hkl}>$ is the average intensity of multiple observations.
[c]$R_{cryst} = \Sigma\ |F_{obs} - F_{calc}|/\Sigma\ F_{obs}$ where $F_{obs}$ and $F_{calc}$ are the observed and calculated structure factor amplitues, respectively.
[d]5% test set
[e]RMSD, root mean square deviation from the parameter set for ideal stereochemistry

EXAMPLE

X-Ray Structure-Based Epitope Mapping

Figure 17:
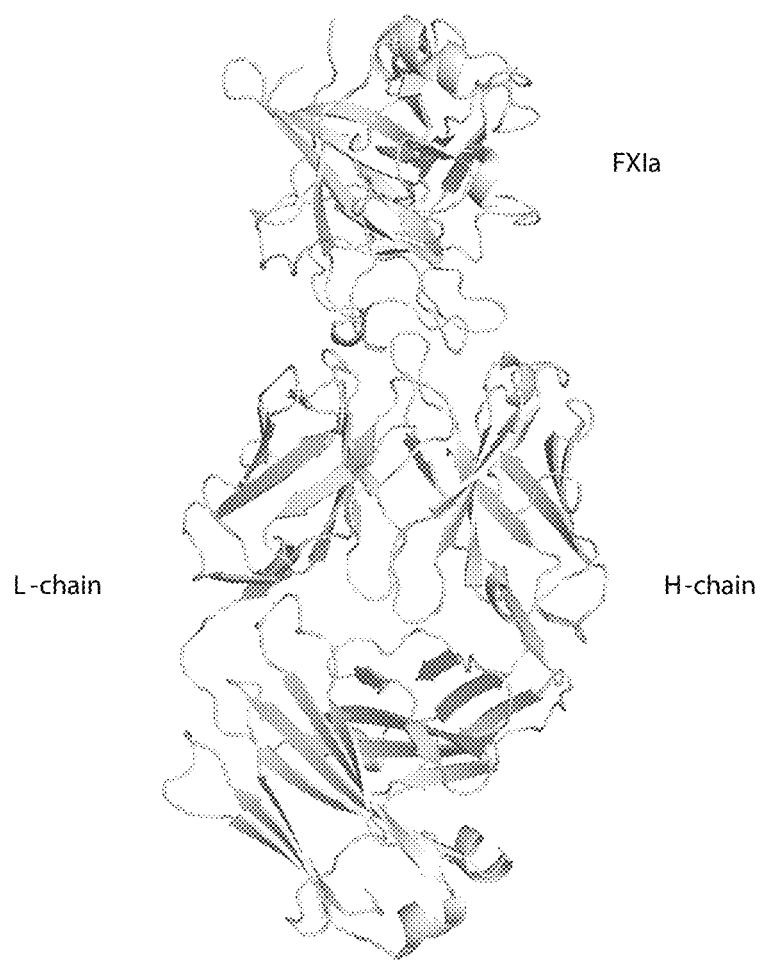
FIG. 17: This figure depicts a cartoon representation of the Fab 076D-M007-H04 (lower part) in complex with FXIa (upper part).

The complex of Fab 076D-M007-H04 and FXIa C500S (FIG. 17) crystallized as one copy of the complex per asymmetric unit. Residues of Fab 076D-M007-H04 (paratope) in contact with FXIa C500S (epitope) were determined and are listed in Tables XA and XB. Buried surface was analyzed with the CCP4 program AREAIMOL (P. J. Briggs (2000) CCP4 Newsletter No. 38) and residues showing a total area difference when calculated with bound and without bound Fab 076D-M007-H04 (Table 11A) and FXIa C500S (Table 11B), respectively.

TABLE 11A

Residues of FXIa in contact with Fab 076D-M007-H04. Epitope

| Residue No. | Area Differences |
|---|---|
| HIS A 406 | −8.30 |
| PRO A 410 | −55.30 |
| THR A 411 | −60.10 |
| GLN A 412 | −2.10 |
| ARG A 413 | −35.60 |
| HIS A 414 | −4.00 |
| ASN A 450 | −12.40 |
| GLN A 451 | −26.90 |
| SER A 452 | −48.20 |
| ILE A 454 | −1.50 |
| LYS A 455 | −32.40 |
| ARG A 522 | −29.90 |
| LYS A 523 | −53.00 |
| LEU A 524 | −105.20 |
| ARG A 525 | −171.10 |
| ASP A 526 | −6.20 |
| LYS A 527 | −120.10 |
| ILE A 528 | −28.60 |
| GLN A 529 | −41.30 |
| ASN A 530 | −58.50 |
| THR A 531 | −6.30 |

TABLE 11B

Residues of Fab 076D-M007-H04 in contact with FXIa. Paratope

| Residue No. | Area Differences |
|---|---|
| SER L 32 | −4.50 |
| ASN L 33 | −15.90 |
| TYR L 34 | −87.20 |
| TYR L 51 | −21.80 |

TABLE 11B-continued

Residues of Fab 076D-M007-H04 in contact with FXIa.
Paratope

| Residue No. | Area Differences |
|---|---|
| ASP L 52 | −18.30 |
| ASN L 55 | −38.10 |
| THR L 58 | −33.50 |
| ALA L 93 | −12.50 |
| ASN L 94 | −36.80 |
| SER L 95 | −11.80 |
| PHE L 96 | −41.30 |
| VAL L 98 | −0.30 |
| THR H 28 | −27.80 |
| GLN H 31 | −60.20 |
| TYR H 32 | −19.00 |
| GLY H 33 | −15.00 |
| ASP H 35 | −3.90 |
| GLY H 50 | −5.60 |
| ILE H 51 | −7.20 |
| GLY H 52 | −10.20 |
| PRO H 53 | −13.30 |
| SER H 57 | −3.00 |
| VAL H 59 | −0.70 |
| GLY H 99 | −8.80 |
| GLY H 100 | −5.50 |
| PRO H 101 | −3.10 |
| TYR H 102 | −149.50 |
| TYR H 103 | −103.50 |
| TYR H 104 | −10.20 |
| TYR H 105 | −52.10 |

In summary, FXIa C500S epitope is formed by the following residues:
HIS A 406, PRO A 410, THR A 411, GLN A 412. ARG A 413, HIS A 414, ASN A 450, GLN A 451, SER A 452, ILE A 454, LYS A 455, ARG A 522, LYS A 523, LEU A 524, ARG A 525, ASP A 526, LYS A 527, ILE A 528, GLN A 529, ASN A 530, THR A 531

Figure 18A:
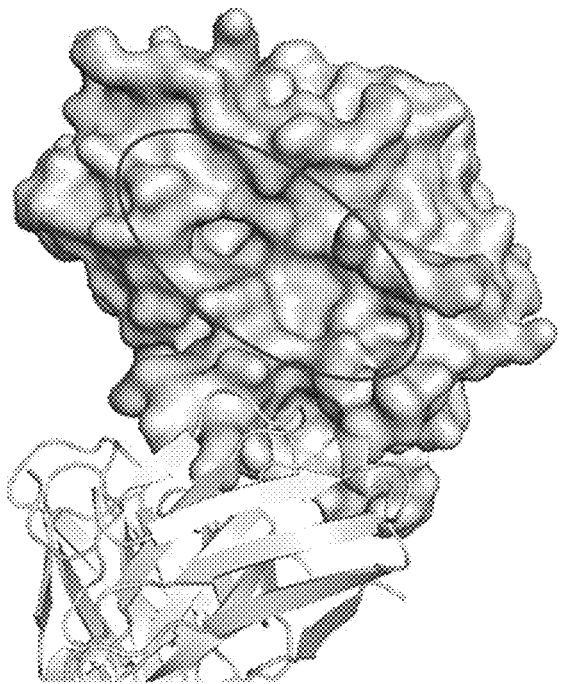
FIG. 18A: This figure depicts—a detailed view into the binding epitope of Fab 076D-M007-H04 (cartoon) to FXIa C500S. FXIa C500S is shown as surface representation.
Figure 18B:
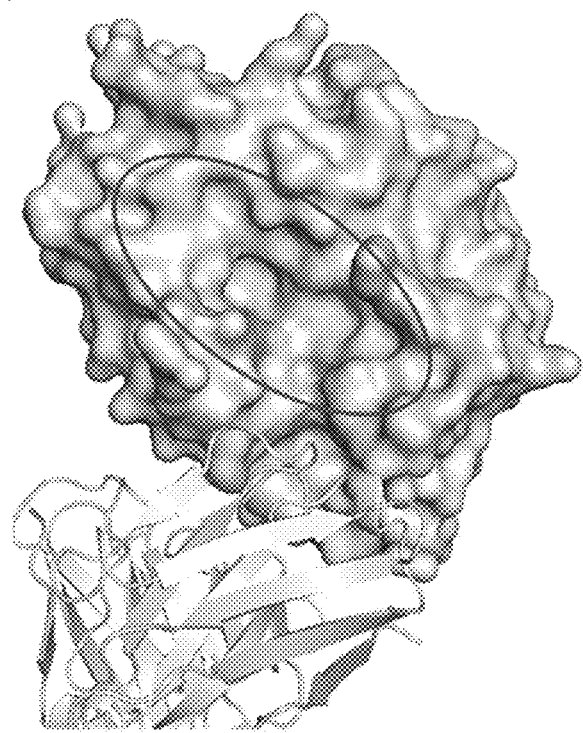
FIG. 18B: This figure shows Fab 076D-M007-H04 with a superimposed peptidic x-ray structure of FXIa C500S shown as surface representation. The active site cleft is highlighted with an ellipsoid.
Figure 19A:
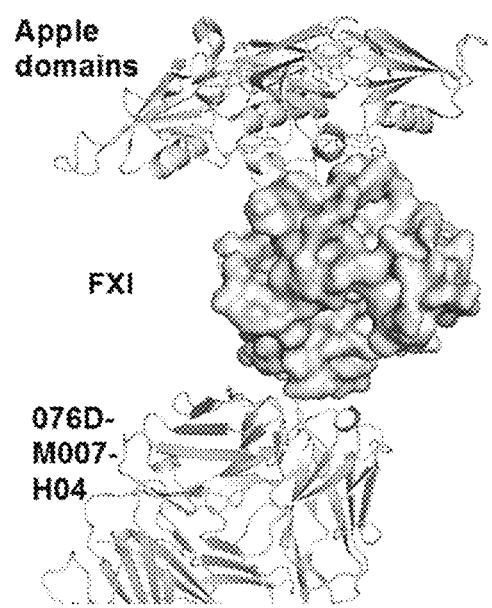
FIG. 19A: This figure depicts the crystal structure of zymogen FXI (odb entry 2F83) with superimposed Fab 076D-M007-H04.
Figure 19B:
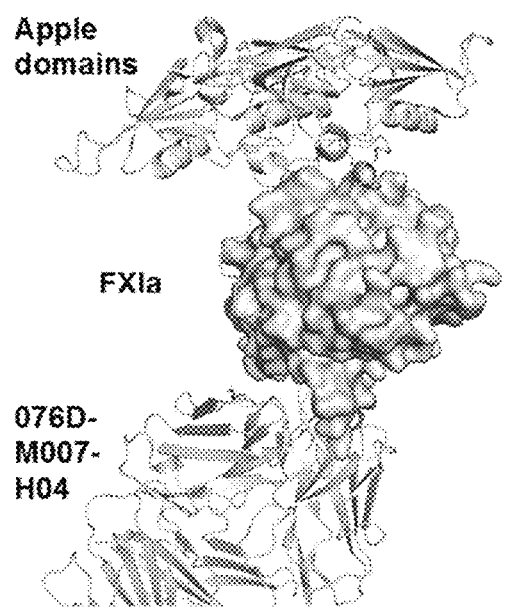
FIG. 19B: This figure depicts the same view but the catalytic domain of FXI of zymogen is replaced by catalytic domain of FXIa C500S of the complex structure of Fab 076D-M007-H04:FXIa C500S. The catalytic domains of FXI and FXIa C500S are shown as surface represenations, all other domains are shown as cartoons. The not properly ordered loops at the interface to Fab 076D-M007-H04 are highlighted.

Fab 076D-M007-H04 acts as a allosteric competitive inhibitor. It is not blocking the active site of FXIa directly but binds adjacent to it. This adjacent binding triggers a re-arrangement of parts of active site of FXIa hindering natural substrates to bind to activated FXIa (FIGS. 18A-18B).

In contrast, Fab 076D-M007-H04 does not bind zymogen FXI. In the reported x-ray structure of zymogen FXI (pdb entry 2F83) various loops building up the active site as well as the epitope to Fab 076D-M007-H04 are not properly ordered. Especially the epitope region is well structured in the Fab 076D-M007-H04:FXIa C500S complex.

EXAMPLE 9

Hydrogen/Deuterium-Exchange Mass Spectrometry-Based Epitope Mapping

A different analysis of Epitope mapping has been performed by the contract research organization ExSAR [ExSAR Corporation; 11 Deer Park Drive, Suite 103; Monmouth Junction, N.J. 08852; USA]. In this case, the interactions of FXIa C500S (amino acids 388-625; purchased by Proteros Biostructures) and the purified Fabs of 076D-M007-H04 and 076D-M049-015, respectively, have been analyzed by the differential hydrogen/deuterium exchange mass spectrometry method [for overview see Percy A J, Rey M, Burns K M, Schriemer D C. (2012) Probing protein interactions with hydrogen/deuterium exchange and mass spectrometry—a review. Anal Chim Acta. 721:7-21]. Thereby, differences in the deuteration level of more than 10% indicates a strong protection by the Fab of the corresponding antigen. Values between 5 and 10% indicate weak binding, differences in the deuteration level of below 5% indicates no protection at all.

Table 12A and Table 12B are summarizing the residues of Fab 076D-M007-H04 and of Fab 076D-M049-015 in contact with FXIa, respectively.

TABLE 12A

Residues of Fab 076D-M007-H04 in contact with FXIa.

| Residue Nr | average deuteration level difference (%) |
|---|---|
| THR 408 | 5-10 |
| SER 409 | 5-10 |
| PRO 410 | 5-10 |
| THR 411 | 5-10 |
| GLN 412 | 5-10 |
| ARG 413 | 5-10 |
| HIS 414 | 5-10 |
| LEU 415 | 5-10 |
| CYS 416 | 5-10 |
| GLY 417 | 5-10 |
| GLY 418 | 5-10 |
| SER 419 | 5-10 |
| ILE 420 | 5-10 |
| ILE 421 | 5-10 |
| GLY 422 | 5-10 |
| ASN 423 | 5-10 |
| GLN 424 | 5-10 |
| VAL 444 | >10 |
| TYR 445 | >10 |
| SER 446 | >10 |
| GLY 447 | >10 |
| ILE 448 | >10 |
| LEU 449 | >10 |
| ASN 450 | >10 |
| GLN 451 | >10 |
| SER 452 | >10 |
| ILE 454 | >10 |
| LYS 455 | >10 |
| THR 517 | >10 |
| GLY 518 | >10 |
| TRP 519 | >10 |
| LYS 523 | 34 |
| LEU 524 | 34 |
| ARG 525 | 34 |
| ASP 526 | 34 |
| LYS 527 | 34 |
| ILE 528 | 34 |
| GLN 529 | 34 |
| ASN 530 | 34 |
| THR 531 | 34 |
| LEU 532 | 34 |
| GLN 533 | 34 |

TABLE 12B

Residues of Fab 076D-M049-O15 in contact with FXIa.

| Residue Nr | average deuteration level difference (%) |
|---|---|
| THR 517 | 5-10 |
| GLY 518 | 5-10 |
| TRP 519 | 5-10 |
| LYS 523 | >10 |
| LEU 524 | >10 |
| ARG 525 | >10 |
| ASP 526 | >10 |
| LYS 527 | >10 |
| ILE 528 | >10 |
| GLN 529 | >10 |
| ASN 530 | >10 |
| THR 531 | >10 |
| LEU 532 | >10 |
| GLN 533 | >10 |

TABLE 12B-continued

Residues of Fab 076D-M049-O15 in contact with FXIa.

| Residue Nr | average deuteration level difference (%) |
|---|---|
| TYR 563 | 5-10 |
| ARG 564 | 5-10 |
| GLU 565 | 5-10 |
| GLY 566 | 5-10 |
| GLY 567 | 5-10 |
| LYS 568 | 5-10 |
| ASP 569 | 5-10 |
| ALA 570 | 5-10 |
| CYS 571 | 5-10 |
| LYS 572 | 5-10 |
| GLY 573 | 5-10 |
| ASP 574 | 5-10 |
| SER 575 | 5-10 |
| GLY 576 | 5-10 |
| GLY 577 | 5-10 |
| PRO 578 | 5-10 |
| LEU 579 | 5-10 |
| SER 580 | 5-10 |
| CYS 581 | 5-10 |
| LYS 582 | 5-10 |
| HIS 583 | 5-10 |
| ASN 584 | 5-10 |
| GLU 585 | 5-10 |
| VAL 586 | 5-10 |
| TRP 587 | 5-10 |
| HIS 588 | 5-10 |
| LEU 589 | 5-10 |
| VAL 590 | 5-10 |
| GLY 591 | 5-10 |
| SER 594 | >10 |
| TRP 595 | >10 |
| GLY 596 | >10 |
| GLU 597 | >10 |
| GLY 598 | >10 |
| CYS 599 | >10 |
| ALA 600 | >10 |
| GLU 603 | >10 |
| ARG 604 | >10 |
| PRO 605 | >10 |
| GLY 607 | >10 |
| VAL 608 | >10 |
| TYR 609 | >10 |

These data clearly show that covering an epitope of 200 amino acids within FXIa (amino acids 408-609 of FXIa C500S) leads to an inhibition of FXIa proteolytic activity.

EXAMPLE 10

Functional Neutralization of FXIa by Antibodies of this Invention

Figure 2:
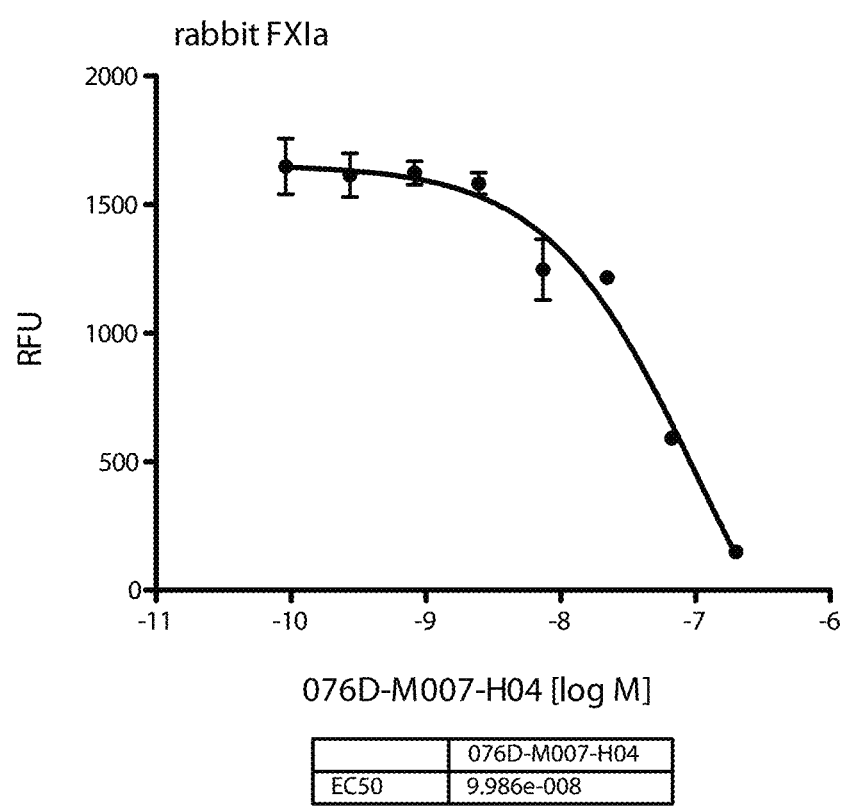
FIG. 2: Dose-response curves of anti-FXIa antibody 076D-M007-H04 inhibiting rabbit FXIa. The antibody identified in the panning/screening campaign was tested at the indicated concentrations for its ability to inhibit the proteolytic activity of rabbit FXIa.
Figure 3:
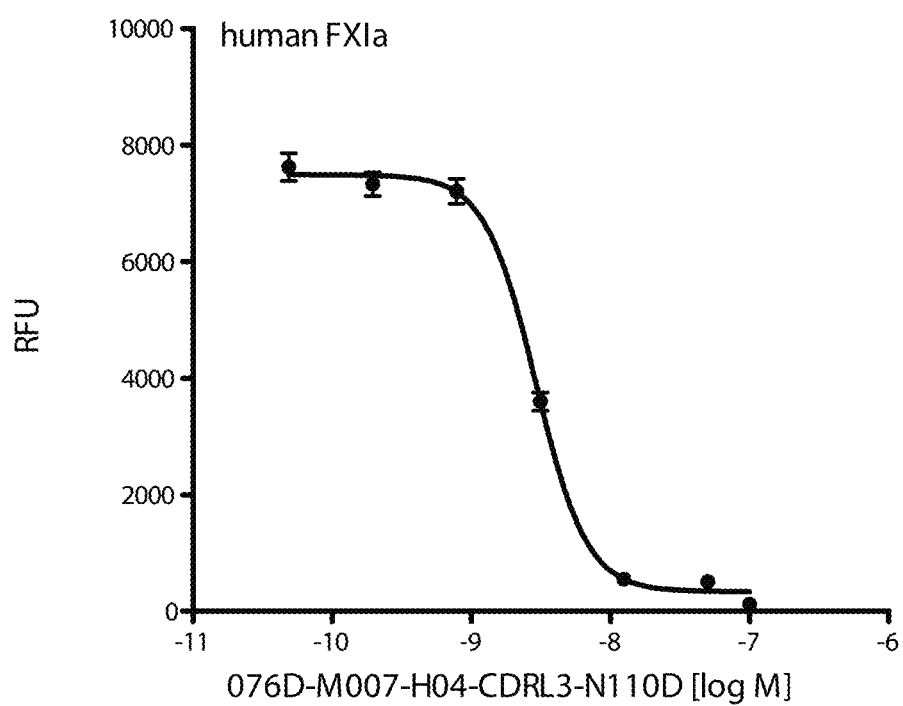
FIG. 3: Dose-response curves of anti-FXIa antibody 076D-M007-H04-CDRL3-N110D comprising SEQ ID NO: 27 for the amino acid sequence for the variable light chain domain and SEQ ID NO: 20 for the amino acid sequence for the variable heavy chain domain inhibiting human FXIa. The antibody identified in the panning/screening campaign was tested at the indicated concentrations for its ability to inhibit the proteolytic activity of human FXIa.
Figure 4:
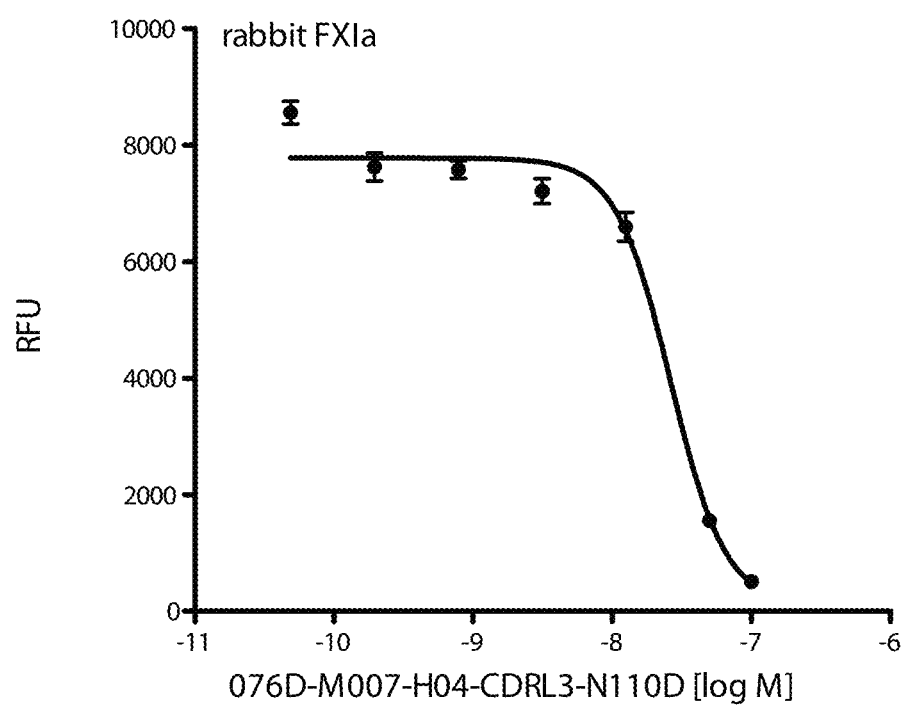
FIG. 4: Dose-response curves of anti-FXIa antibody 076D-M007-H04-CDRL3-N110D. The antibody identified in the panning/screening campaign was tested at the indicated concentrations for its ability to inhibit the proteolytic activity of rabbit FXIa.

Human FXIa (Haematologic Technologies, Inc., catalogue number HCXIA-0160) activity is determined by measuring the cleavage of a specific, fluorogenically-labeled substrate (1-1575, Bachem, final concentration 25 μM) and the fluorescence is monitored continuously at 360/465 nm using a SpectraFluorplus Reader (Tecan). For testing the inhibitory activity, the antibodies are pre-incubated for 60 minutes at 37° C. with a final concentration of 10 nM of FXIa in a buffer containing 50 mM Tris/HCl, 100 mM NaCl, 5 mM CaCl$_2$ and 0.1% BSA. Following this incubation step, the substrate 1-1575 is added, and the signals from the reaction are measured. Data are analyzed using the GraphPadPrism software as shown in FIG. 1, FIG. 2, FIG. 3, and in FIG. 4. Data are given as mean+SEM, n=4.

For some experiments instead of the full length human FXIa (Haematologic Technologies, Inc., catalogue number HCXIA-0160) the isolated catalytic domain of FXIa C500S (amino acids 388-625; purchased by Proteros Biostructures) is used. All other conditions are as described above.

EXAMPLE 11

Figure 5:
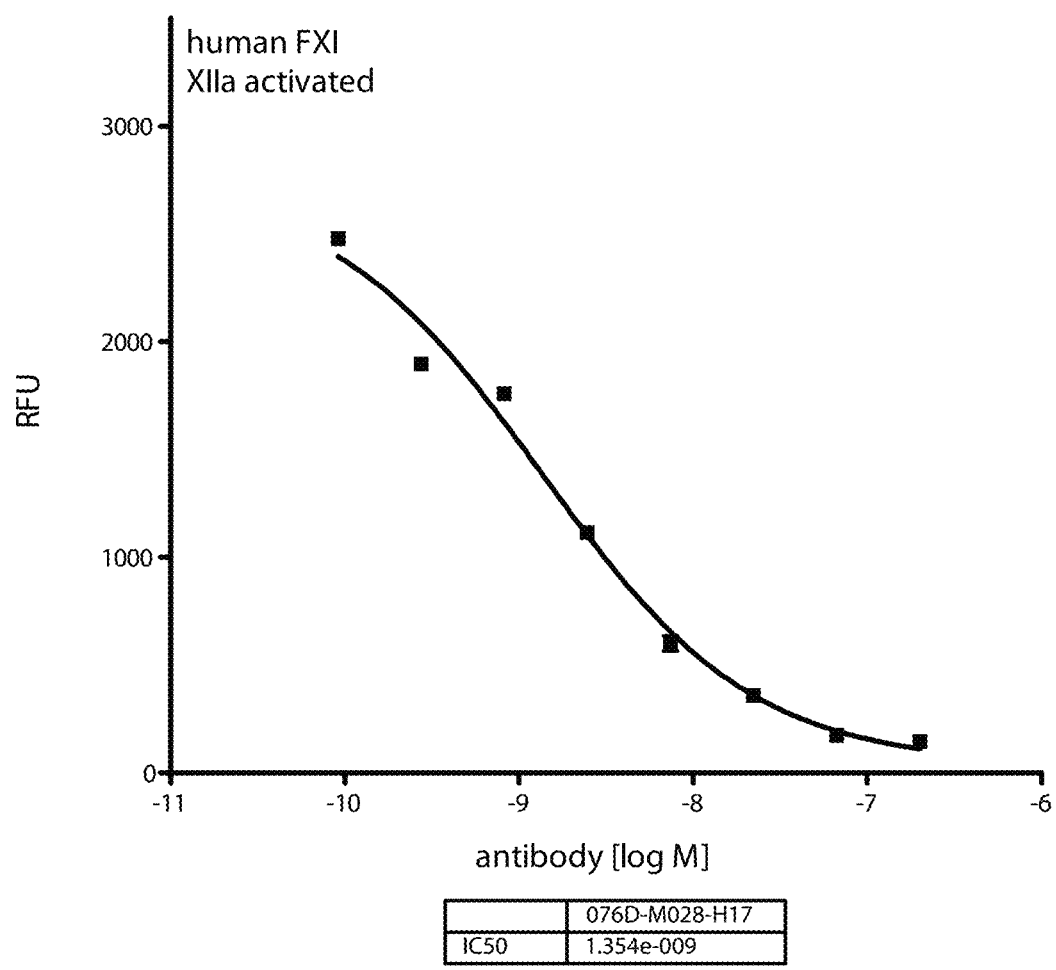
FIG. 5: Dose-response curves of anti-FXI antibody 076D-M028-H17 comprising SEQ ID NO: 29 for the amino acid sequence for the variable light chain domain and SEQ ID NO: 30 for the amino acid sequence for the variable heavy chain domain inhibiting the conversion human FXI to FXIa by the coagulation factor XIIa. This antibody comprises CDRH1 as SEQ ID NO: 31, CDRH2 as SEQ ID NO: 32 and CDRH3 as SEQ ID NO: 33. This antibody further comprise CDRL1 as SEQ ID NO: 34, CDRL2 as SEQ ID NO: 35 and CDRL3 as SEQ ID NO: 36. The antibody identified in the panning/screening campaign was tested at the indicated concentrations for their ability to inhibit the conversion of the zymogen FXI into its activated form FXIa. The related DNA sequences are shown as SEQ ID NO: 11 to SEQ ID NO: 18.
Figure 6:
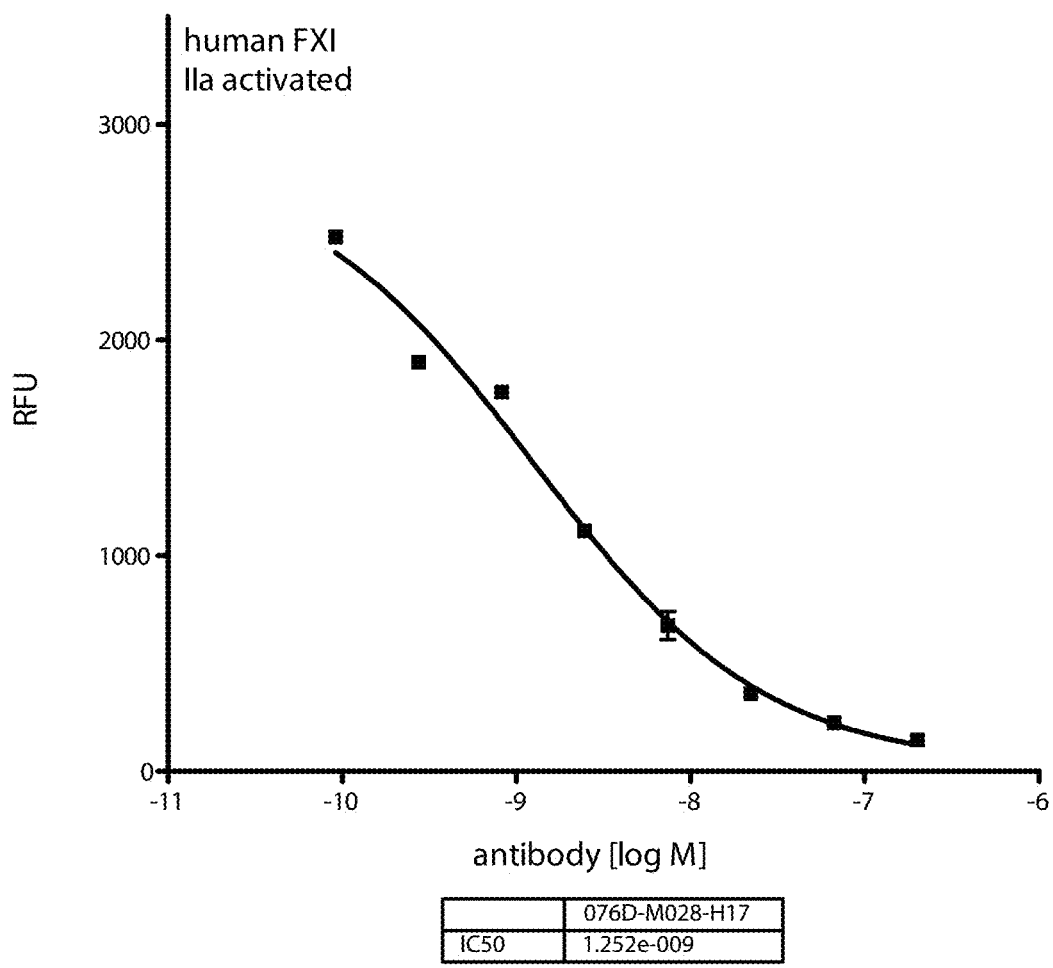
FIG. 6: Dose-response curves of anti-FXI antibody 076D-M028-H17 of inhibiting the conversion human FXI to FXIa by the coagulation factor IIa. The antibody identified in the panning/screening campaign was tested at the indicated concentrations for their ability to inhibit the conversion of the zymogen FXI into its activated form FXIa.
Figure 7:
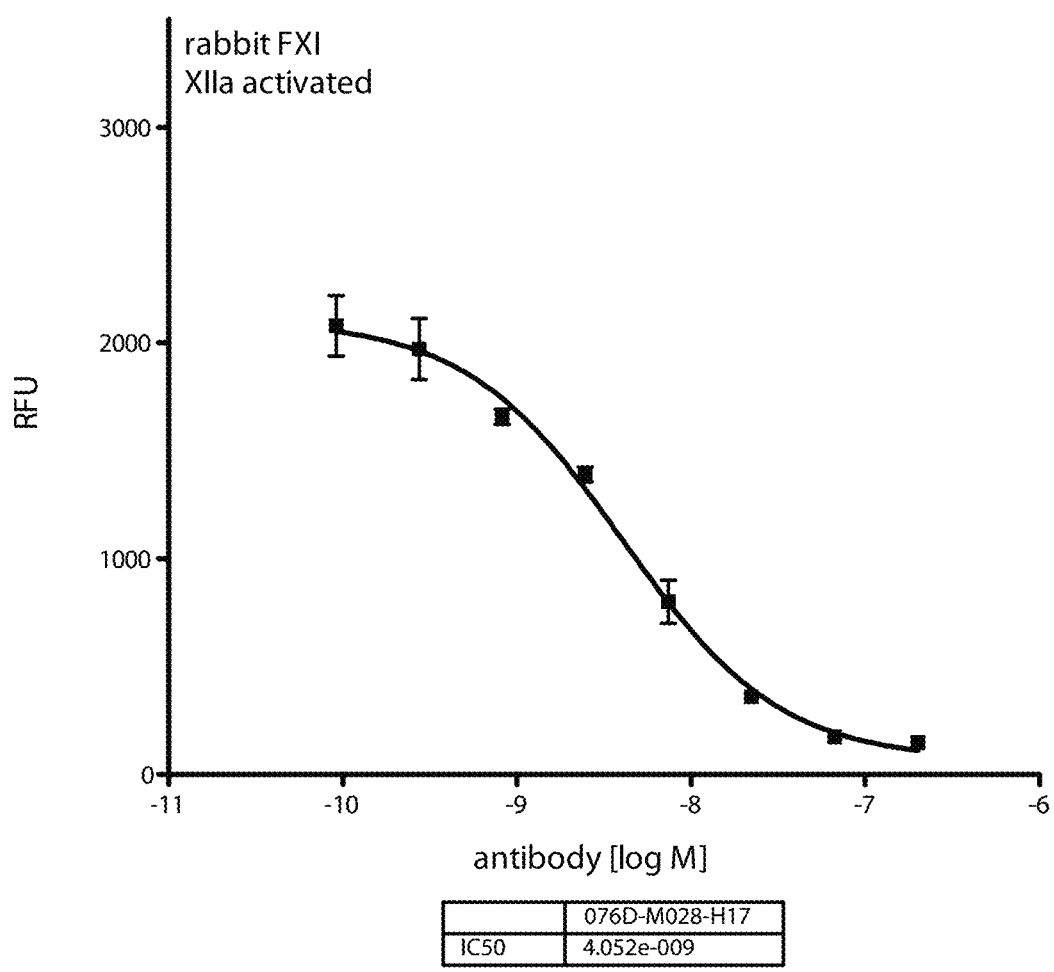
FIG. 7: Dose-response curves of anti-FXI antibody 076D-M028-H17 of inhibiting the conversion rabbit FXI to FXIa by the coagulation factor XIIa. The antibody identified in the panning/screening campaign was tested at the indicated concentrations for their ability to inhibit the conversion of the zymogen FXI into its activated form FXIa.
Figure 8:
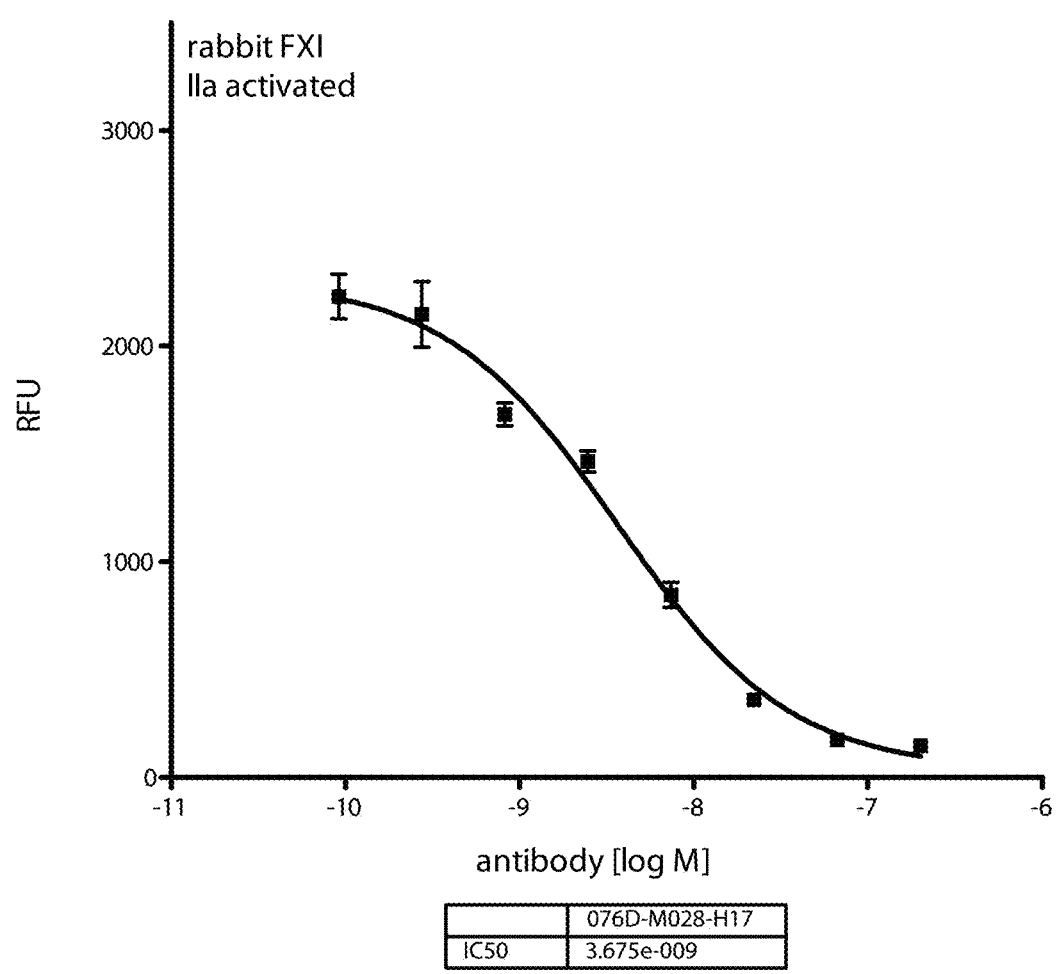
FIG. 8: Dose-response curves of anti-FXI antibody 076D-M028-H17 of inhibiting the conversion rabbit FXI to FXIa by the coagulation factor IIa. The antibody identified in the panning/screening campaign was tested at the indicated concentrations for their ability to inhibit the conversion of the zymogen FXI into its activated form FXIa.
Figure 9:
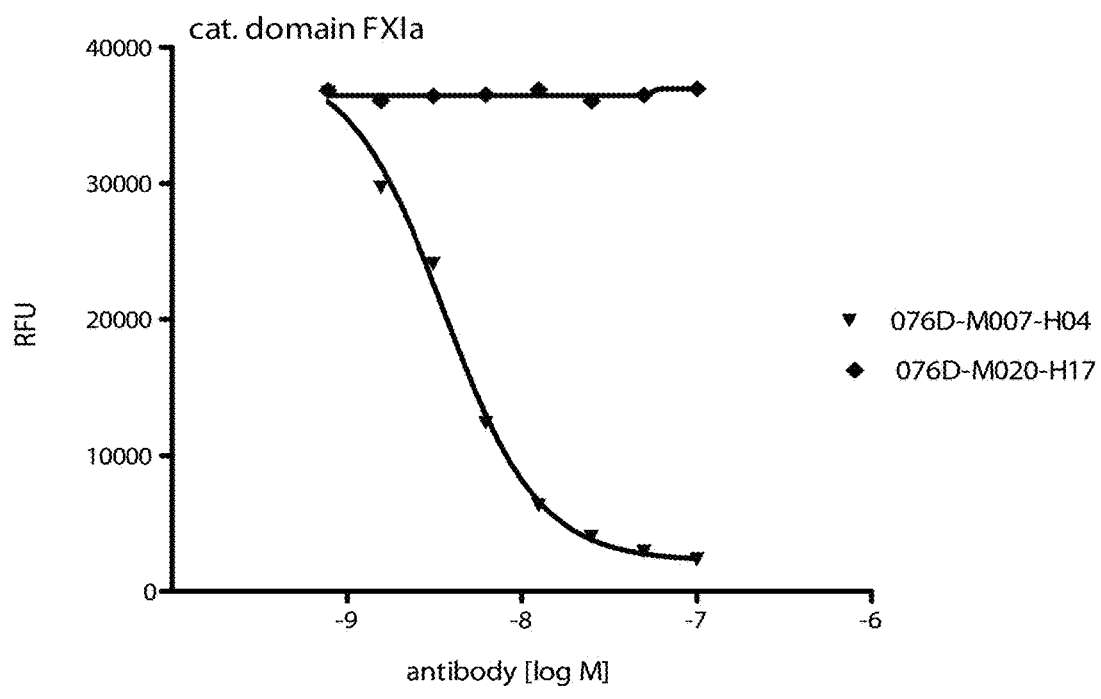
FIG. 9: Binding and blocking activity of 076D-M007-H04 to the catalytic domain of human FXIa. Whereas 076D-M007-H04 inhibits the proteolytic activity of human FXIa, 076D-M028-H17 does not exhibit such an activity, indicating that 076D-M007-H04 binds to the catalytic domain of FXIa.
Figure 10:
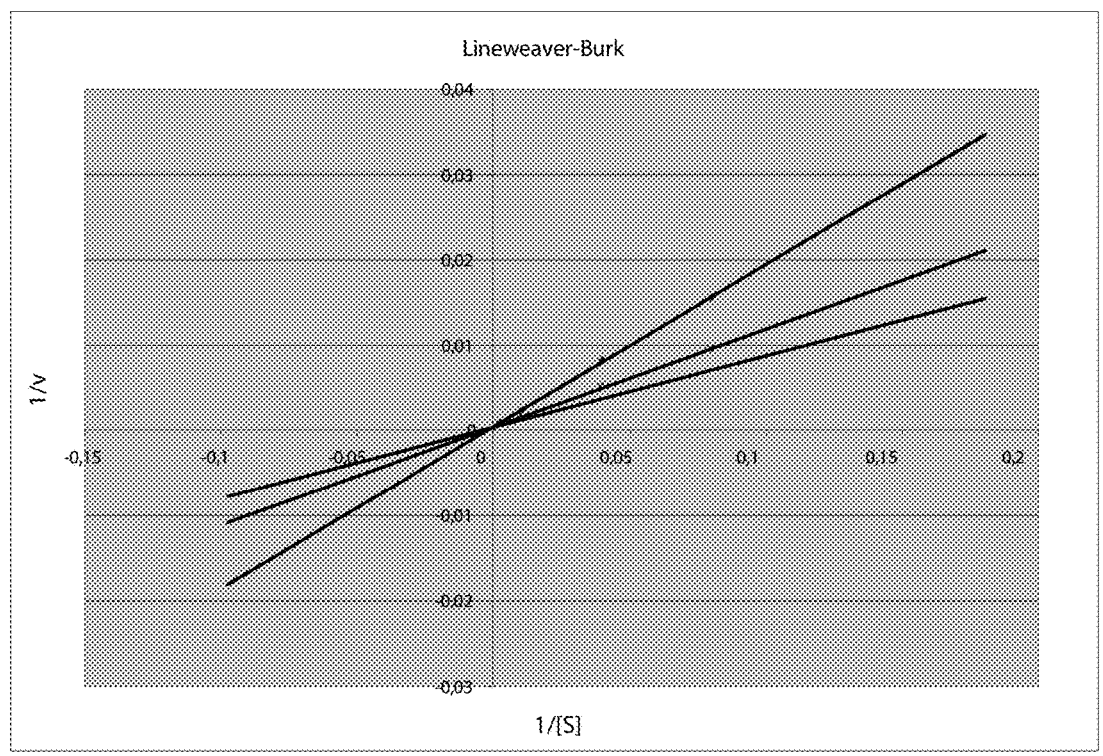
FIG. 10: Characterization of the binding modus of 076D-M007-H04 using the Lineweaver-Burk plot shows that this antibody exhibits a competitive type inhibition activity.
Figure 11A:
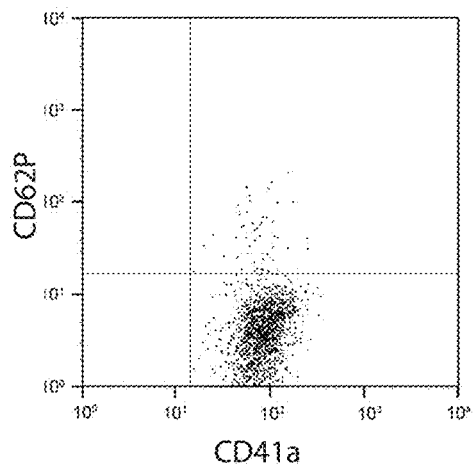
FIGS. 11A-11D: Flow cytometric analysis for CD62P expression and platelet microaggregate formation. Single platelets were detected by the combination of light scattering and FITC-CD41/CD61 (GPIIbIIIa) fluorescence. Determination of CD62P expression by a dot plot with FITC-CD41 and PE-CD62P fluorescence. Gated platelets before (FIG. 11A) and after (FIG. 11B) perfusion are shown. Platelet microaggregate formation was defined with the increased size (forward scatter), indicated in the circle. Dot plots of samples collected before (FIG. 11C) and after (FIG. 11D) perfusion are shown.
Figure 11B:
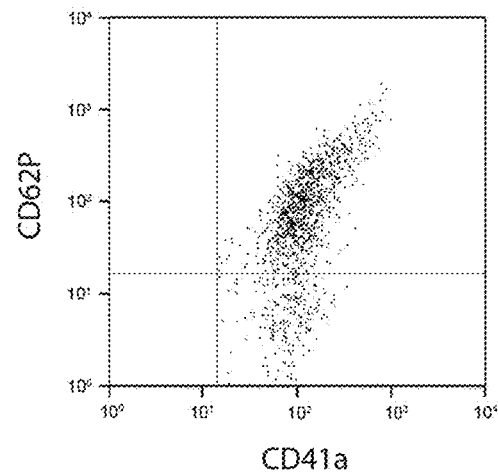
Figure 11C:
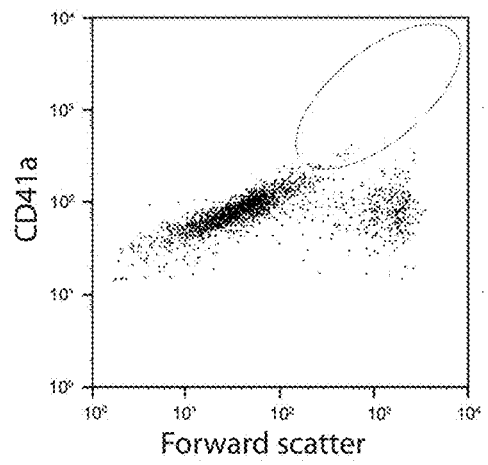
Figure 11D:
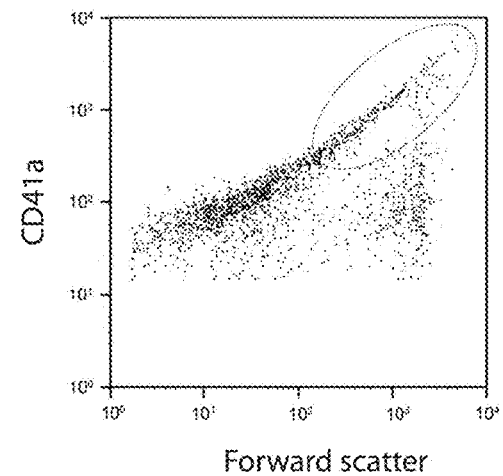
Figure 12A:
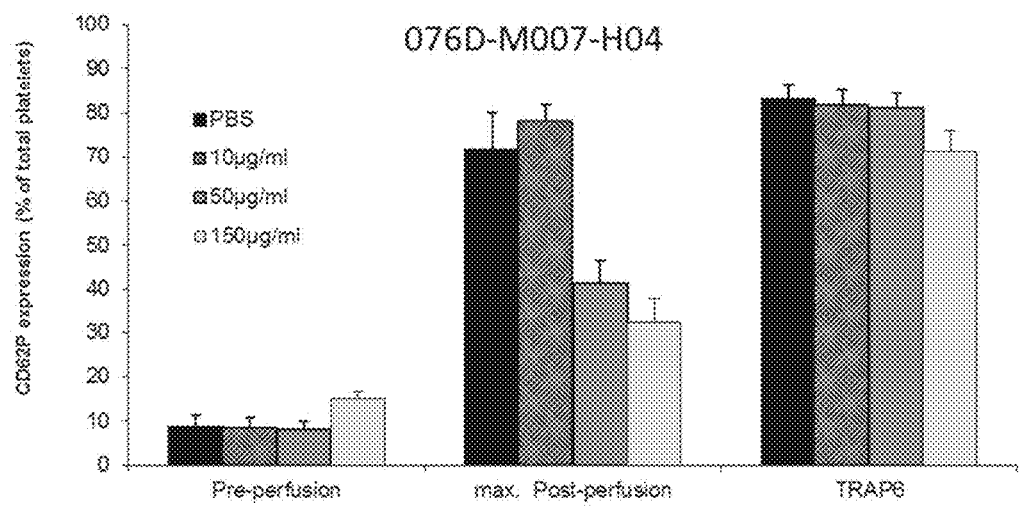
FIGS. 12A-12B: Platelet CD62P expression was reduced by FXI(a) antibodies. Whole blood was treated with 076D-M007-H04 (FIG. 12A) and 076D-M028-H17 (FIG. 12B) and perfused over collagen-coated surface immediately after recalcification. In parallel, whole blood samples were collected after treatment with vehicle or inhibitor, and incubated with or without TRAP6 (10 µg/ml) for 5 min. Platelet CD62P expression was analyzed by flow cytometry as shown in FIGS. 11A-11B. Data are reported as mean±SEM percentage of CD62P-positive platelets in gated population of at least 5 experiments. The maximum CD62P expression levels during 5 min perfusion in each treatment are shown in the graphs.
Figure 12B:
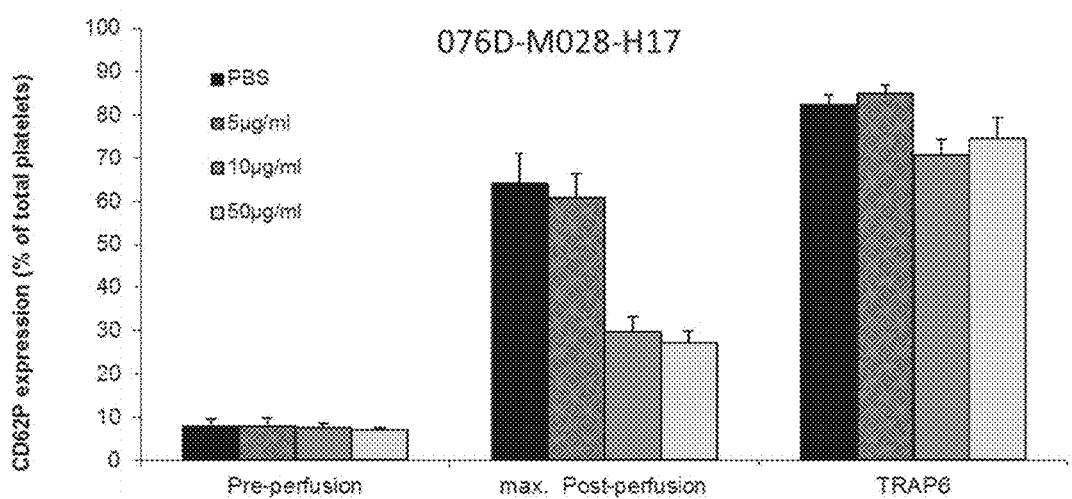
Figure 13A:
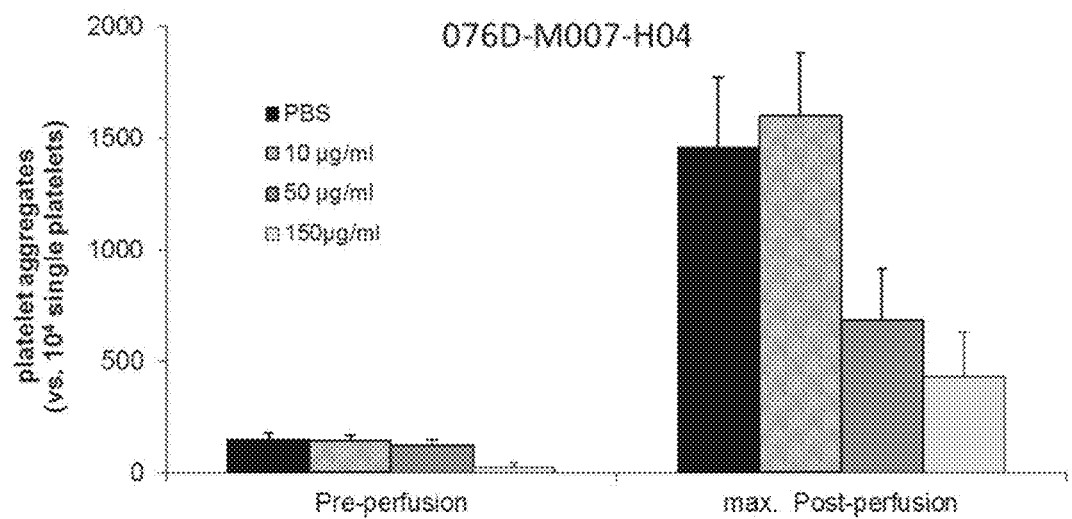
FIGS. 13A-13B: Platelet microaggregate formation was inhibited by FXI(a) antibodies. Whole blood was treated with 076D-M007-H04 (FIG. 13A) and 076D-M028-H17 (FIG. 13B) and perfused over collagen-coated surface immediately after recalcification. Platelet microaggregates were analyzed by flow cytometry as shown in FIGS. 11C-11D. Data are reported as mean±SEM aggregate count versus $10^4$ gated single platelets of at least 5 experiments. The maximum aggregate counts during 5 min perfusion in each treatment are shown in the graphs.
Figure 13B:
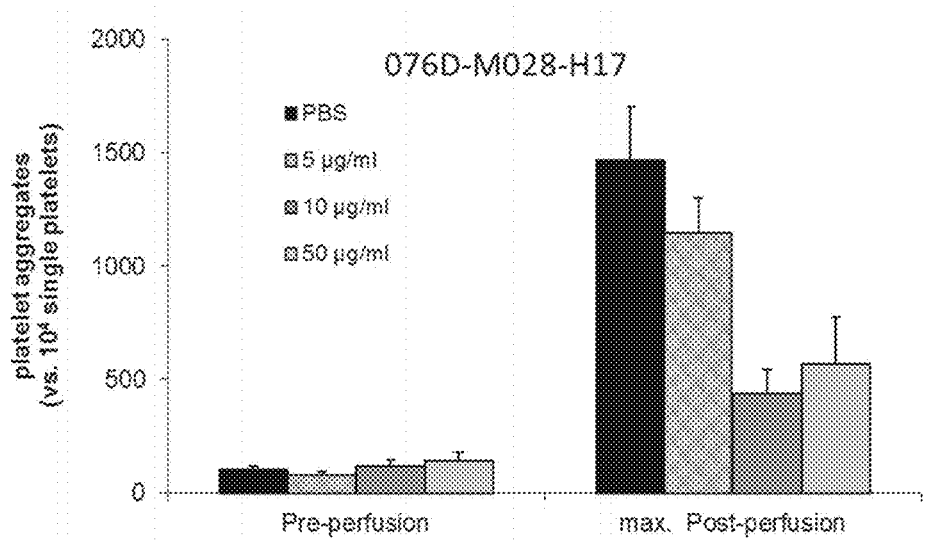

Functional Neutralization of the Conversion of FXI into its Active Form, FXIa, by Antibodies of this Invention For testing the inhibition of the conversion of FXI (Haematologic Technologies, Inc., catalogue number HCXIA-0150) into its active form FXIa by FXIIa or Thrombin (Thrombin is IIa), 10 nM of human FXI is incubated in 50 mM Tris/HCl, 100 mM NaCl, 5 mM CaCl$_2$ und 0.1% BSA with different concentrations of the antibodies for 1 hour at 37° C. In a next step, 10 nM final concentration of human FXIIa (Enzyme Research, catalogue number HFXIIa 1212a) or Thrombin (Enzyme Research, catalogue number HT 1002a) at a final concentration of 1 unit/mg are added and incubated for 24 hours at 37° C. Next the Corn Trypsin Inhibitor (Enzyme Research, CTI) at a final concentration of 200 nM and the fluorogenically-labeled substrate (1-1575, Bachem, final concentration 25 μM) are added. The fluorescence is monitored continuously at 360/465 nm using a SpectraFluorplus Reader (Tecan). Data are analyzed using the GraphPadPrism software as shown in FIG. 5 and FIG. 7 for the FXIIa mediated conversion of FXI and in FIG. 6 and FIG. 8 for the Thrombin induced conversion of FXI into its activated form FXIa. Data are given as mean±SEM, n=4.

EXAMPLE 12

Evaluation of the Anti-Thrombotic Activity of the Anti-FXIa Antibody 076D-M007-H04 in an Experimental Thrombosis In Vivo Model in Primates Experimental Procedures Experiments were conducted on non-anticoagulated awake juvenile baboons weighing 9-11 kg. These animals had chronic exteriorized arterio-venous (AV) shunts placed between the femoral artery and vein, as described elsewhere (Hanson et al. (1993) Journal of Clinical Investigation 92:2003-2012). Baseline shunt blood flow exceeded 250 ml/min in all study animals. Anxiety was managed with low dose ketamine (<2 mg/kg/hr). Whole blood cell counts were measured daily, before and after the experiments. Calculated blood loss did not exceed 4% of total blood volume on any experimental day.

Thrombus formation was initiated within the baboon AV shunt by interposing a thrombogenic segment of prosthetic vascular graft (ePTFE, WL Gore & Co., Flagstaff, Ariz.), as previously described (Hanson et al. [1993] J. Clin. Invest. 92:2003-2012). To consistently trigger platelet-dependent thrombus formation, the clinical graft segments were coated with immobilized collagen. Twenty mm long grafts having internal diameters (i.d.) of either 2 mm or 4 mm were filled with equine type I collagen (1 mg/ml; Nycomed Arzenmittel, Munich, Germany) for 15 min, and then dried overnight under sterile airflow. This method produced a uniform collagen coating within the graft lumen as determined by scanning electron microscopy. In addition, in some experiments, a 20 mm long chamber of 9 mm i.d. followed the 20 mm long graft with 4 mm i.d. to model average venous and arterial shear rates, respectively. The thrombogenic collagen-coated grafts were then incorporated between segments of silicon rubber tubing, and deployed into the AV shunts.

The grafts were exposed to blood for up to 60 min. During each experiment, the blood flow rate through the graft was restricted to 100 ml/min by clamping the proximal silicone rubber shunt segment, thereby producing a mean wall shear rate (MWSR) in the 4 mm grafts of 265/sec, while in the 2 mm grafts the initial MWSR was 2120/sec. Flow rates were continuously monitored using an ultrasonic flow meter (Transonics Systems, Ithaca, N.Y.). The 4 mm grafts did not occlude and pulsatile flow rates remained at 100 ml/min until the thrombogenic graft segments were removed at 60 min. Baseline blood flow was restored through the permanent shunt after each experiment. In the 2 mm diameter grafts blood flow rates progressively declined due to thrombus formation. The grafts were removed from the AV shunts when the flow rate fell from 100 ml/min to below 20 ml/min, signaling imminent occlusion. The time from initiation of blood flow to graft removal (<20 ml/min blood flow) was taken as the occlusion time.

For imaging of the platelet deposition, autologous baboon platelets were labeled with 1 mCi of 111 In-oxine as previously described (Hanson et al. [1993] J. Clin. Invest. 92:2003-2012). Labeled platelets were infused and allowed to circulate for at least 1 hr before studies were performed. Accumulation of labeled platelets onto thrombogenic grafts and silicon chambers were measured in 5-min intervals using a gamma scintillation camera. Homologous 125I-labeled baboon fibrinogen (4 µCi, >90% clottable) was infused 10 min before each study, and incorporation of the labeled fibrin within the thrombus was assessed using a gamma counter >30 days later to allow the 111 In to decay. The radioactivity deposited (cpm) was divided by the clottable fibrin(ogen) radioactivity of samples taken at the time of the original study (cpm/mg).

Occlusion studies were performed using 20 mm long, 2 mm i.d. collagen-coated devices which produced high initial wall shear rates (2120/sec at 100 ml/min clamped blood flow). Accumulation of labeled platelets onto the 2 mm thrombogenic grafts were measured in 3-min intervals using a gamma scintillation camera. Flow was maintained at 100 ml/min by proximal clamping for as long as possible, and then allowed to decrease as the propagating thrombus began to occlude the device. A final blood flow rate of 20 ml/min was used as a cutoff for occlusion, since a fully occlusive thrombi and lack of blood flow through the device could lead to occlusion of the shunt and a significant loss of blood for the animals.

Blood sample analysis. Blood cell counts were determined using a micro-60 automated cell counter (Horiba-ABX Diagnostics). Blood samples were collected into a final concentration of 0.32% sodium citrate. All samples were centrifuged for 5 min at 12,900 g, and the plasmas were collected and stored at minus 80° C. Cross-reacting ELISA assays were used to determine thrombin-antithrombin complexes (TAT, Enzygnost-TAT, Dade-Behring; LOD: 2 ng/mL). All ELISA test kits utilized for these studies have previously shown sensitivity to baboon markers.

In interruption studies (4 mm i.d. collagen-coated graft only), 076D-M007-H04 was administered as a bolus 30 minutes into the study (0.5 mg/kg, i.v. bolus over 10 seconds) to determine whether this antibody can interrupt acute thrombus propagation. In occlusion studies (2 mm i.d. collagen-coated graft only), 076D-M007-H04 was administered as a bolus 3 hours before the experiment (0.5 mg/kg or 2 mg/kg 24 hours following a 0.5 mg/kg dose, i.v.). In prevention studies (4 mm i.d. collagen-coated graft followed by 9 mm i.d. silicon chamber), 076-M007-H04 was administered as a bolus 1 hour before the experiment (0.5 mg/kg or 2 mg/kg 24 hours following a 0.5 mg/kg dose, i.v.).

Hemostatic assessment. The effects of FXIa inhibition on primary hemostasis in baboons were assessed using the standard template skin bleeding time test (Surgicutt®, International Technidyne Corp). Experimentally, this and similar tests (e.g., Simplate bleeding times) have been shown to be sensitive to the effects of therapeutic anticoagulants, antiplatelet agents, and coagulation abnormalities in humans and non-human primates (Gruber et al. [2007] Blood 109: 3733-3740; Smith et al. [1985] Am. J. Clin. Pathol. 83:211-215; Payne et al. [2002] J. Vasc. Surg. 35:1204-1209). All bleeding time measurements were performed by the same expert technician. For indirect assessment of hemostasis, aPTT (activated partial thromboplastin time; SynthASil, HemosIL; Instrumentation Laboratory Company, Bedford, Mass.) and ACT (activated clotting time, LupoTek KCT; r2 Diagnostics, South Bend, Ind.) measurements were also performed at various time-points before, during, and after the experiments.

Figure 20:
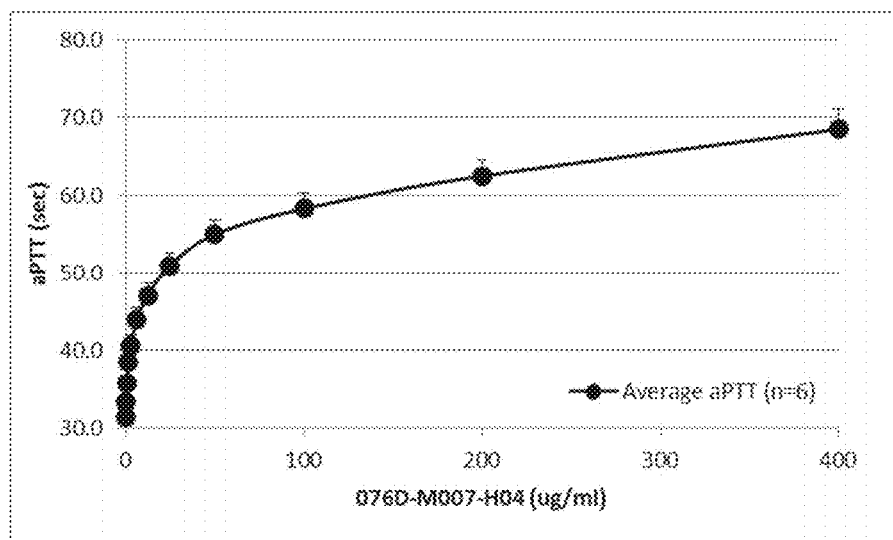
FIG. 20: Increase in in vitro aPTT clotting time determined in plasma samples collected from baboons following 076D-M007-H04 administration.

In vitro aPTT. Various concentrations of 076D-M007-H04 were incubated in plasma for 10 minutes prior to the initiation of the aPTT assay. As shown in FIG. 20, aPTT clotting times were determined in plasma samples collected from the baboons at the "pre" time-point, i.e., before any treatment was administered. Results show that 076D-M007-H04 was anticoagulant in plasma from all 6 experimental baboons used in the thrombosis studies.

Figure 21:
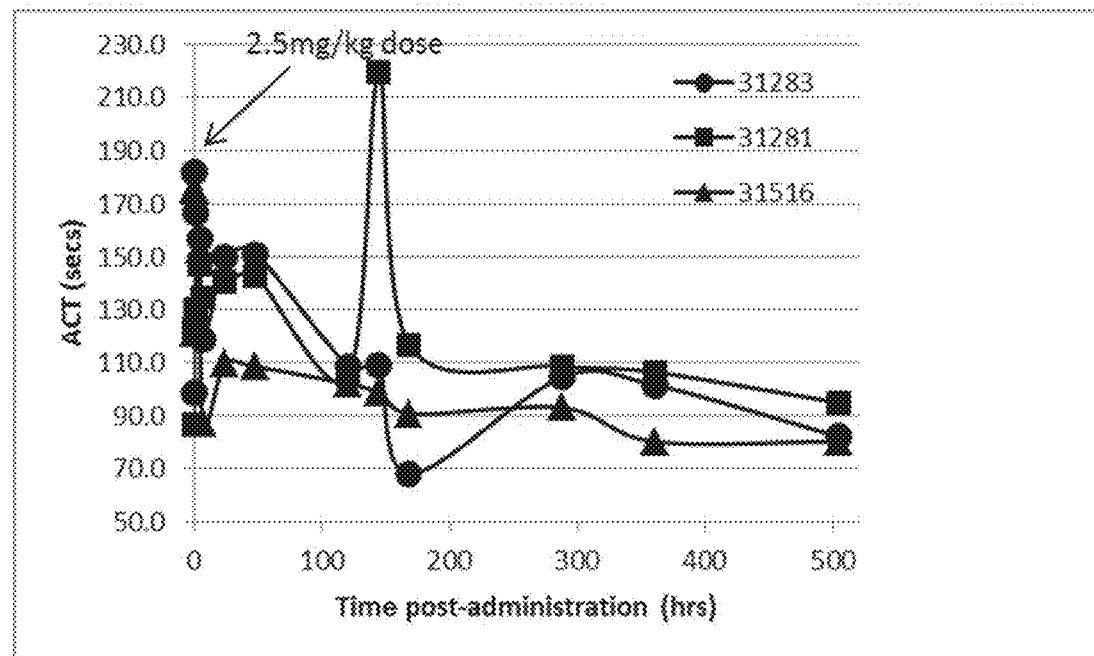
FIG. 21: ACT measurements following 2.5 mg/kg 076D-M007-H04 administration (i.v. bolus) from 5 minutes post-dose through 504 hours post-dose.
Figure 22:
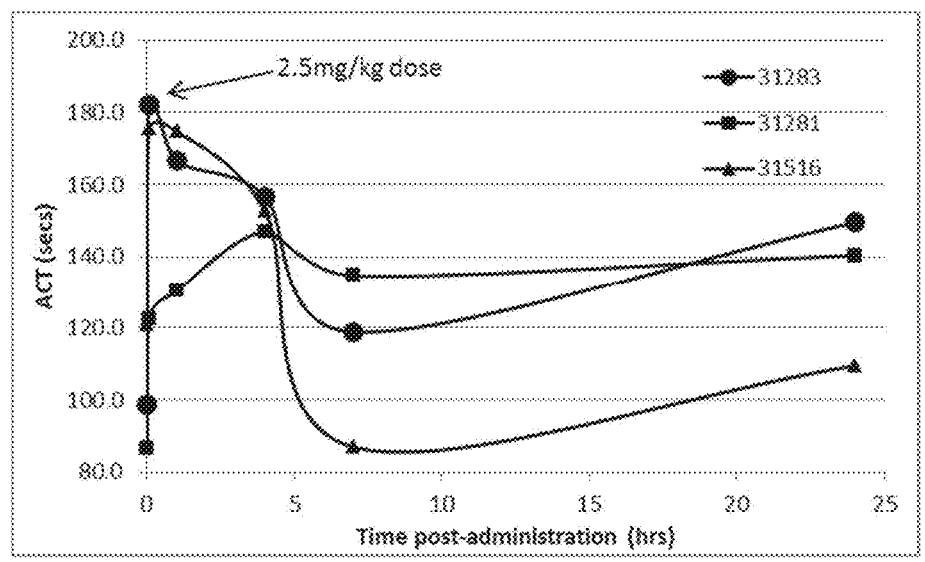
FIG. 22: The first 24 hours of ACT measurements following 2.5 mg/kg 076D-M007-H04 administration (i.v. bolus).
Figure 23:
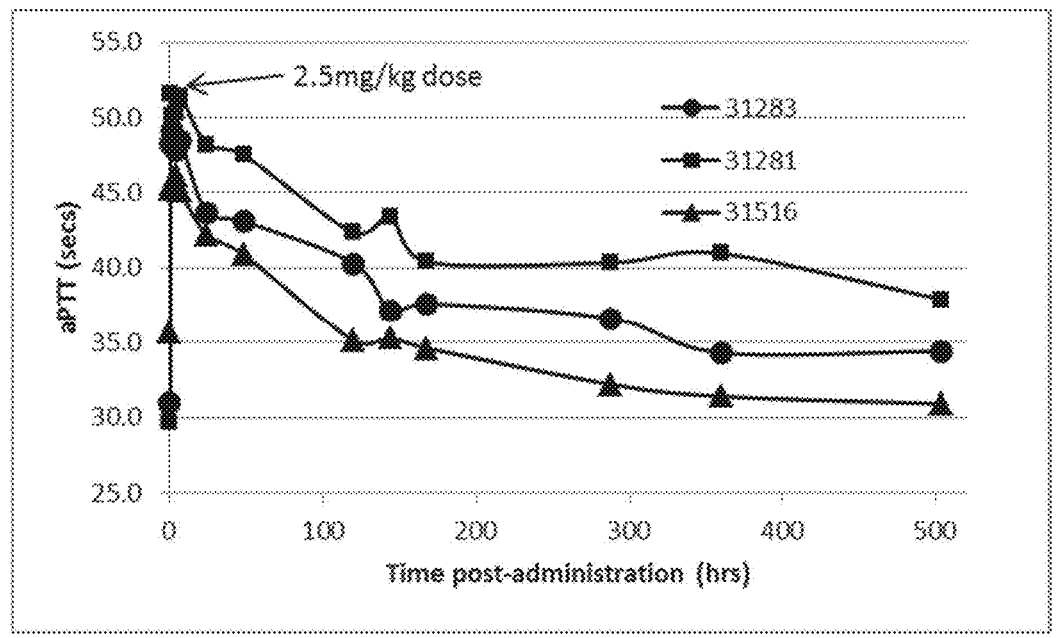
FIG. 23: aPTT measurements following 2.5 mg/kg 076D-M007-H04 administration (i.v. bolus) from 5 minutes post-dose through 504 hours post-dose.
Figure 24:
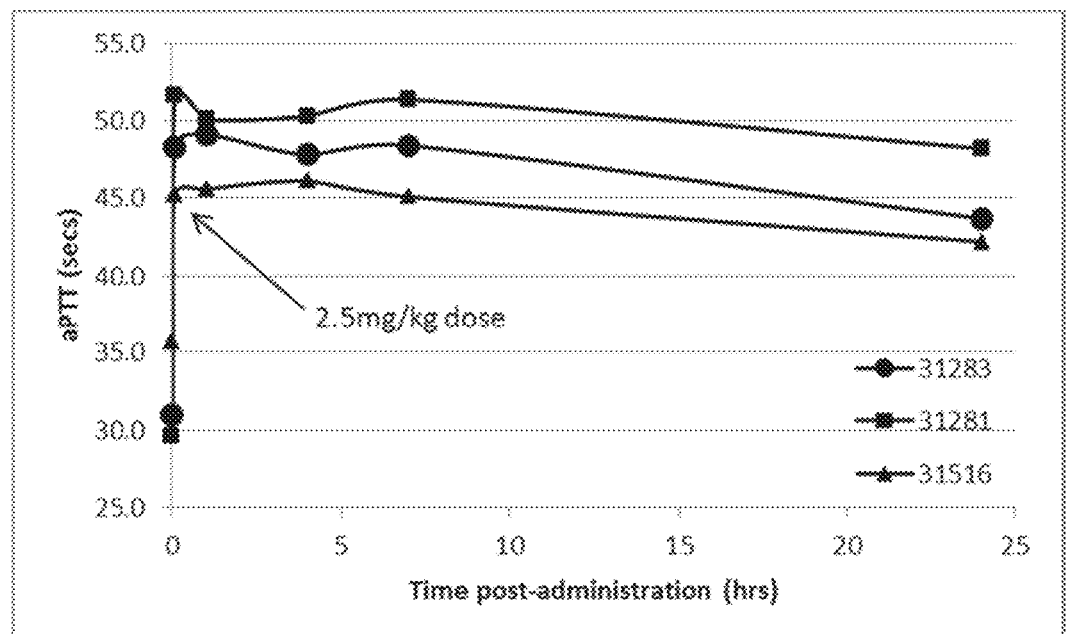
FIG. 24: The first 24 hours of aPTT measurements following 2.5 mg/kg 076D-M007-H04 administration (i.v. bolus).

In vivo clotting Studies. Three baboons were used in these studies: two baboons were dosed with 076D-M007-H04 (2.5 mg/kg H04, i.v. bolus) after being given 32 m/kg chewable aspirin and 1 baboon was dosed with 0.5 mg/kg 076D-M007-H04 (i.v. bolus) followed by a 2 mg/kg dose 24 hours later (i.v. bolus). ACT (FIG. 21 and FIG. 22) and aPTT (FIG. 23 and FIG. 24) were measured at various time-points following administration.

Platelet Deposition During Shunt Experiments

Thrombosis occlusion experiments. The thrombogenic device that was used to evaluate whether 076D-M007-H04 treatment can prevent occlusion of a small blood vessel or prolong the time to occlusion consisted of a 2 mm i.d., 20 mm long collagen-coated graft.

Figure 25:
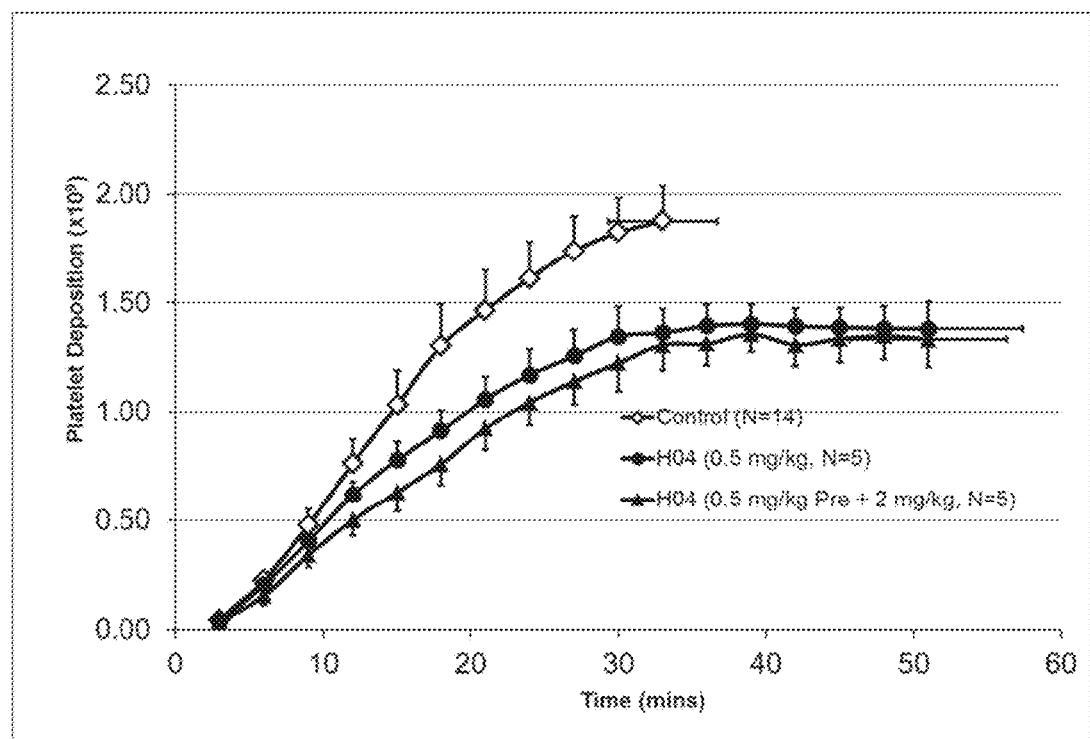
FIG. 25: Platelet deposition in 2 mm i.d. collagen-coated ePTFE vascular grafts.

As shown in FIG. 25, platelet deposition is shown for 60 minutes or until the time of graft occlusion when applicable. 12/14 control devices occluded within 60 minutes, while 2/5 076D-M007-H04 (0.5 mg/kg) and 2/5 076D-M007-H04 (0.5 mg/kg+2 mg/kg) devices occluded. Data are means±SEM.

Figure 26:
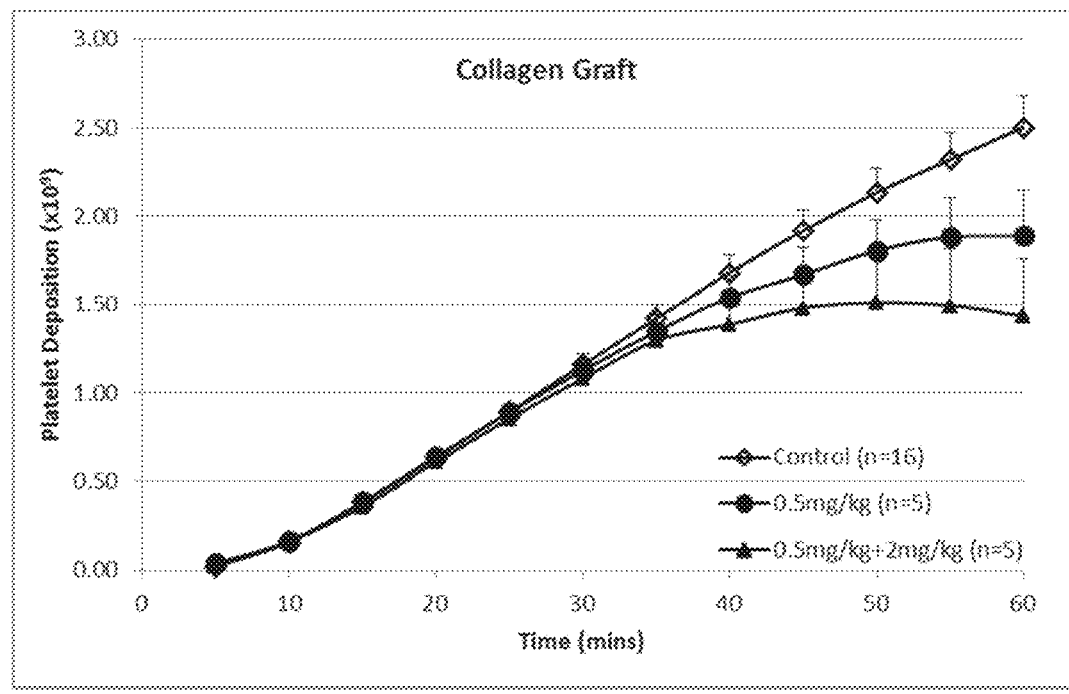
FIG. 26: Platelet deposition on collagen-coated ePTFE vascular grafts as described in Example 12.

Thrombosis prevention experiments. The thrombogenic device that was used to evaluate the effect of 076D-M007-H04 on thrombus initiation and propagation consisted of a 4 mm i.d., 20 mm long collagen-coated ePTFE graft that was followed by a 9 mm i.d., 20 mm long silicon rubber chamber. The slope of platelet deposition as shown in FIG. 26 is an indication of antiplatelet activity. Both doses of 076D-M007-H04 (0.5 mg/kg and 0.5 mg/kg followed by 2 mg/kg 24 hours later) showed efficacy as evidenced by reduction in the rates of platelet deposition at various times from the initiation of thrombus formation. The data have been normalized to account for platelet count variations between experiments. Data are means+SEM.

Figure 27:
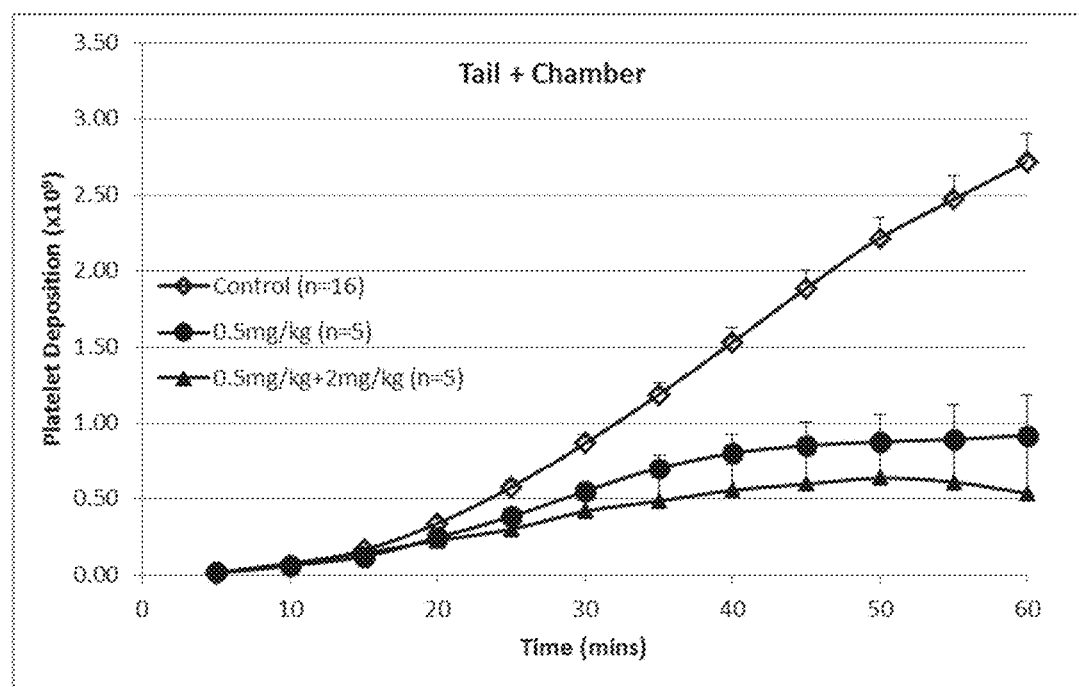
FIG. 27: Platelet deposition in the venous expansion chamber (and in the linker section between the collagen-coated graft and the silicon chamber) as described in Example 12.

As shown in FIG. 27 both doses of 076D-M007-H04 (0.5 mg/kg and 0.5 mg/kg followed by 2 mg/kg 24 hours later) showed efficacy as evidenced by the profound reduction in the rates of platelet deposition in the silicon chamber at various times from the initiation of thrombus formation. Data are means±SEM.

Figure 28:
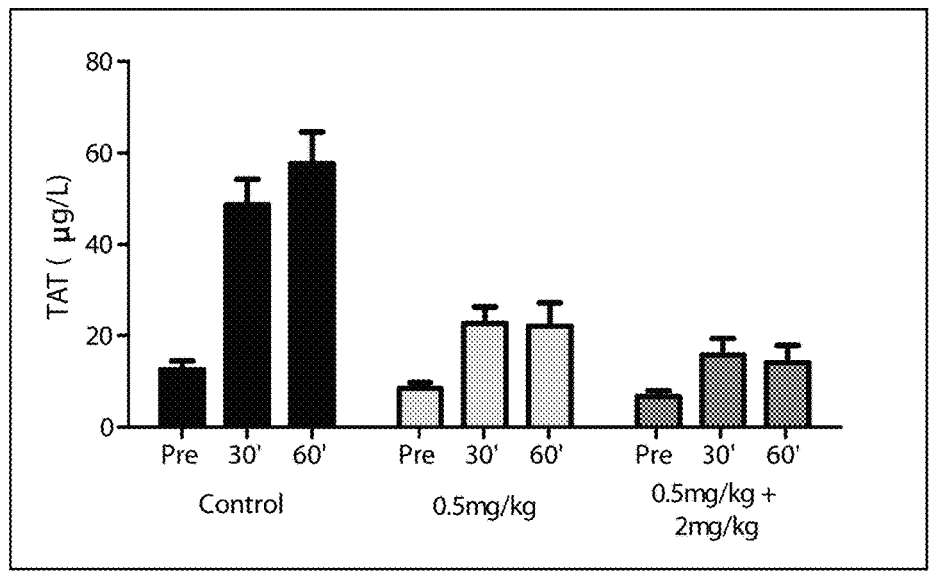
FIG. 28: TAT levels measured in baboon plasma following 076D-M007-H04 administration.

Thrombin anti-thrombin complexes. Since inhibition of FXI could reduce thrombus formation in vivo both by limiting thrombin-mediated platelet activation and fibrin formation and/or by increasing thrombolysis, levels of thrombin anti-thrombin (TAT) were measured using a commercially available ELISA kit. As shown in FIG. 28, pretreatment of baboons with 076D-M007-H04 (0.5 mg/kg and 0.5 mg/kg followed by 2 mg/kg 24 hours later) prevented the increase in TAT levels, implying a profound reduction in thrombin generation in the absence of FXIa activity.

Bleeding Times. Primary hemostasis was evaluated using the adult Surgicutt device from ITC Nexus Holding Company (now Accriva Diagnostics) that has been approved by the FDA for use in children and adults. Bleeding time (BT) was manually recorded. The wound was observed for rebleeding for 30 minutes, and the skin was evaluated for bruising, petechiae, hematomas, and suffusions the next day. One or more of these hemostasis assessments have been shown to be sensitive and predictive of the antihemostatic effects of virtually all marketed antithrombotic agents (antiplatelet drugs, anticoagulants, thrombolytics).

Figure 29:
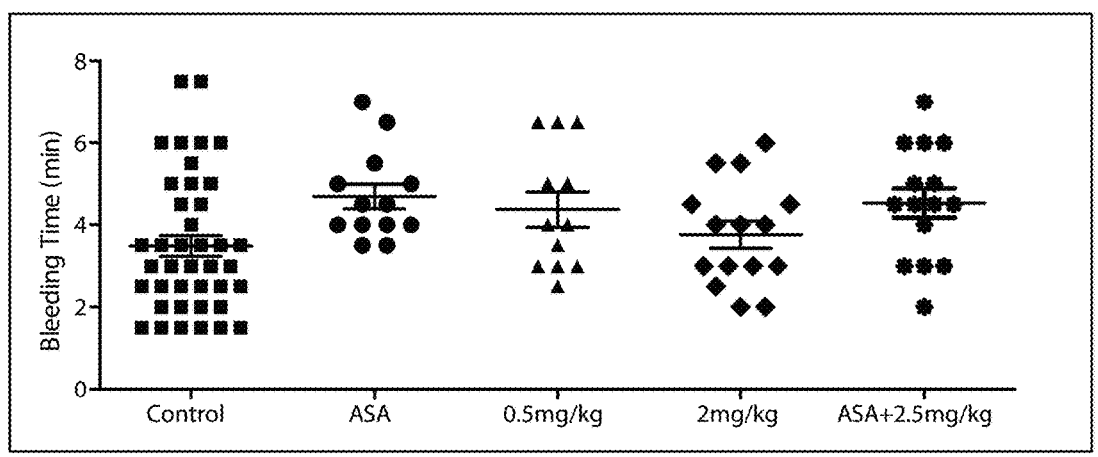
FIG. 29: Bleeding time in baboons treated with 0.5 mg/kg 076D-M007-H04 and 2 mg/kg 076D-M007-H04 (24 hours later) alone or after they were given chewable aspirin at a concentration of 32 mg/kg.

Baboons were administered 076D-M007-H04 (0.5 mg/kg and 2 mg/kg 24 hours later) alone or after they were given chewable aspirin (ASA, 32 mg/kg). As shown in FIG. 29 there was no increase in bleeding time with any of the 076D-M007-H04 treatments compared to baseline. Administration of 076D-M007-H04 to aspirin-treated animals did not seem to further increase the bleeding time compared to aspirin treatment alone.

The invention claimed is:

1. Human monoclonal antibody capable of binding to FXIa or an antigen-binding fragment thereof comprising CDRH1 as SEQ ID NO: 21, CDRH2 as SEQ ID NO: 22, and CDRH3 as SEQ ID NO: 23; CDRL1 as SEQ ID NO: 24, CDRL2 as SEQ ID NO: 25, and CDRL3 as SEQ ID NO: 26.

2. Human monoclonal antibody capable of binding to FXIa or an antigen-binding fragment thereof comprising SEQ ID NO: 19 for the variable light chain domain and SEQ ID NO: 20 for the variable heavy chain domain inhibiting platelet aggregation, and by this inhibiting thrombosis without compromising hemostasis.

3. A pharmaceutical composition comprising the antibody or the fragment thereof according to claim 1.

4. A pharmaceutical composition comprising the antibody or the fragment thereof according to claim 2.

5. A medicament comprising the antibody or the fragment thereof according to claim 1.

6. A medicament comprising the antibody or the fragment thereof according to claim 2.

7. A nucleic acid coding for the antibody or the fragment thereof according to claim 1.

8. A vector comprising the nucleic acid according to claim 7.

9. A host cell comprising the vector of claim 8.

10. A nucleic acid coding for the antibody or the fragment thereof according to claim 2.

11. A vector comprising the nucleic acid according to claim 10.

12. A host cell comprising the vector of claim 11.

* * * * *